United States Patent
Han et al.

(10) Patent No.: US 8,722,337 B2
(45) Date of Patent: May 13, 2014

(54) INTEGRATED VERSATILE KIT FOR ISOLATING COMPONENTS IN BIOLOGICAL SAMPLES

(71) Applicant: BexMart, SanFrancisco, CA (US)

(72) Inventors: Bob Han, SanFrancisco, CA (US); Eric Han, SanFrancisco, CA (US); Xiaohui Xiong, SanFrancisco, CA (US); Xiaoliang Han, SanFrancisco, CA (US)

(73) Assignee: BexMart, San Francisco, CA (US)

( * ) Notice: Subject to any disclaimer, the term of this patent is extended or adjusted under 35 U.S.C. 154(b) by 0 days.

(21) Appl. No.: 13/960,548

(22) Filed: Aug. 6, 2013

(65) Prior Publication Data

US 2013/0323831 A1    Dec. 5, 2013

Related U.S. Application Data

(62) Division of application No. 12/979,383, filed on Dec. 28, 2010, now Pat. No. 8,530,228.

(51) Int. Cl.
*G01N 1/00* (2006.01)

(52) U.S. Cl.
USPC .......... 435/6.12; 435/270; 435/272; 435/274; 436/175

(58) Field of Classification Search
USPC .................. 435/6.12, 270, 272, 274; 436/175
See application file for complete search history.

*Primary Examiner* — Kenneth R. Horlick
*Assistant Examiner* — Olayinka Oyeyemi
(74) *Attorney, Agent, or Firm* — Geeta Kadambi; Riddhi IP LLC

(57) ABSTRACT

The instant invention provides an intergrated kit with solutions and instruments to isolate various biological samples from biological samples. The kit enables an user to preserve specimens and isolate biomolecules with features and benefits of high quality, easy, fast, no toxicity, safe to user and environment, low demanding, cost-effective, reducing waste, saving nature resources and protecting environment, and leads to a low-carbon and Green economy in preparation of specimens. The integrated kit enables the user to extract biomolecules including DNA/ccfDNA, Large RNA/mRNA/ccfRNA, Small RNA/miRNA/ccfmiRNA, Protein, Lipid, Carbohydrates, and Metabolite using one seamless procedure.

15 Claims, 27 Drawing Sheets

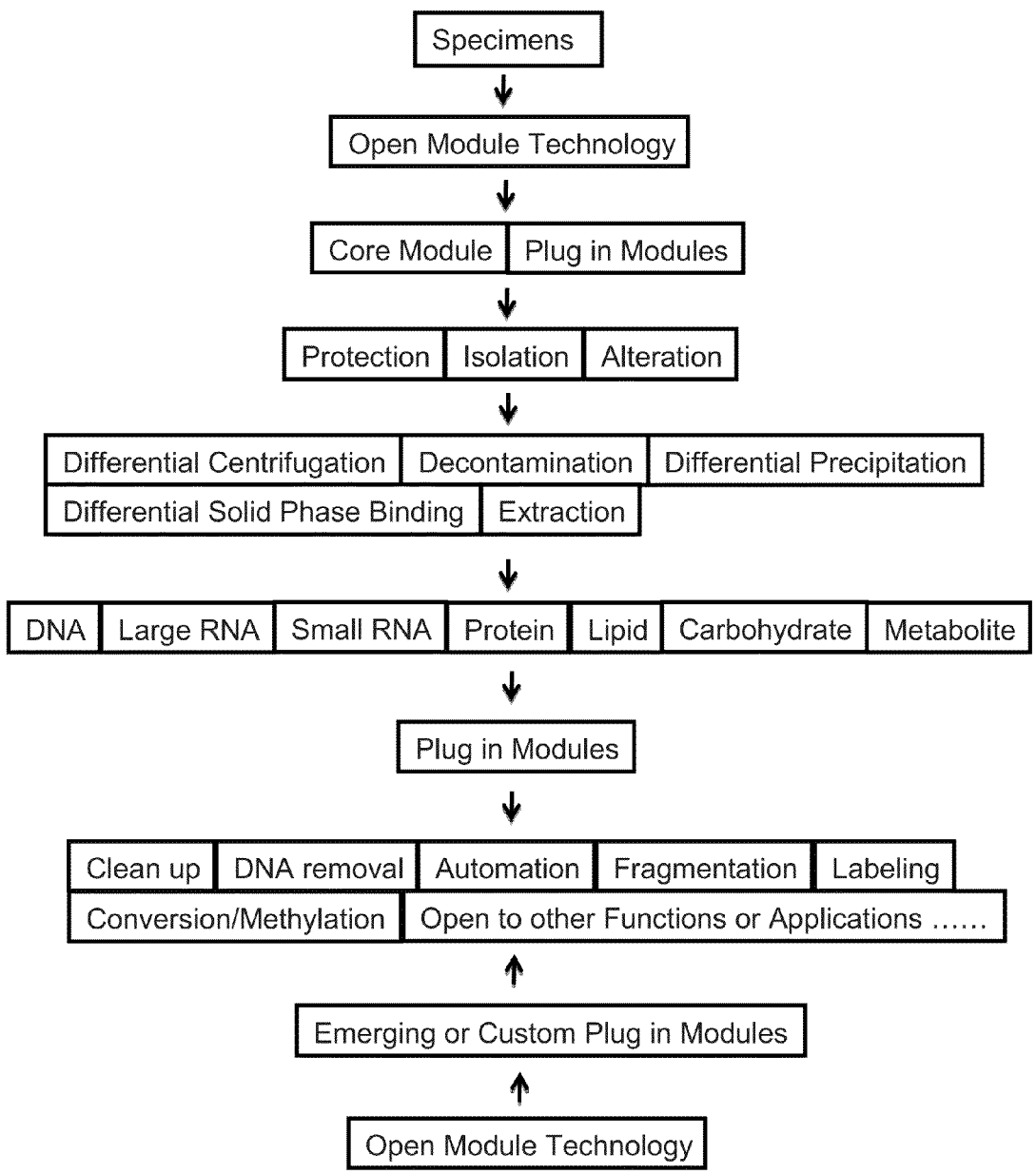
Fig 1. Overview of Integrated Versatile and Systems Preparation of Specimens

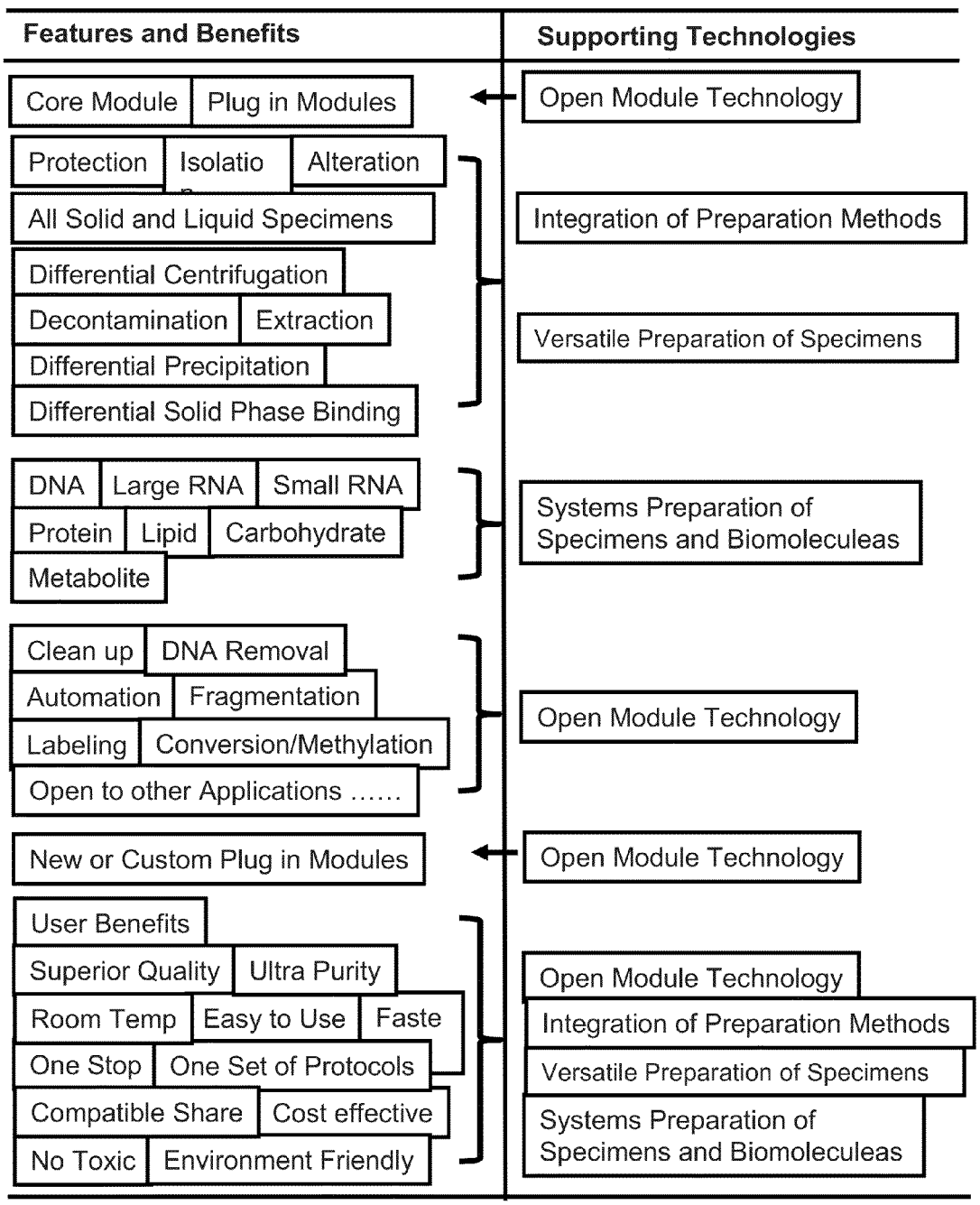
Fig 2. Key Features and Benefits of Integrated Versatile and Systems Preparation of Specimens Fig 3. Protection of Histological Structure and micromorphology of Specimens by the PLIS solutions from the core module
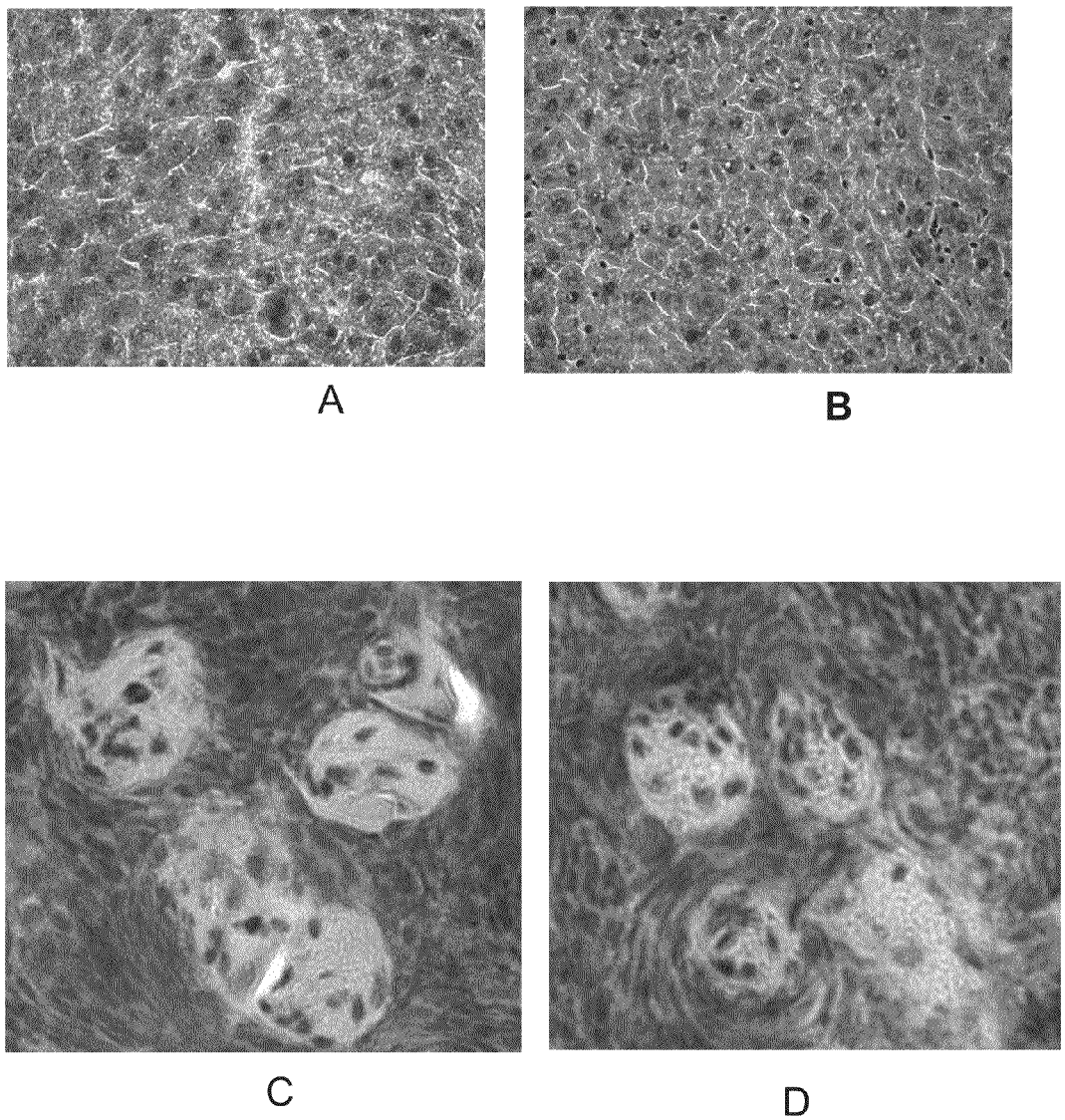

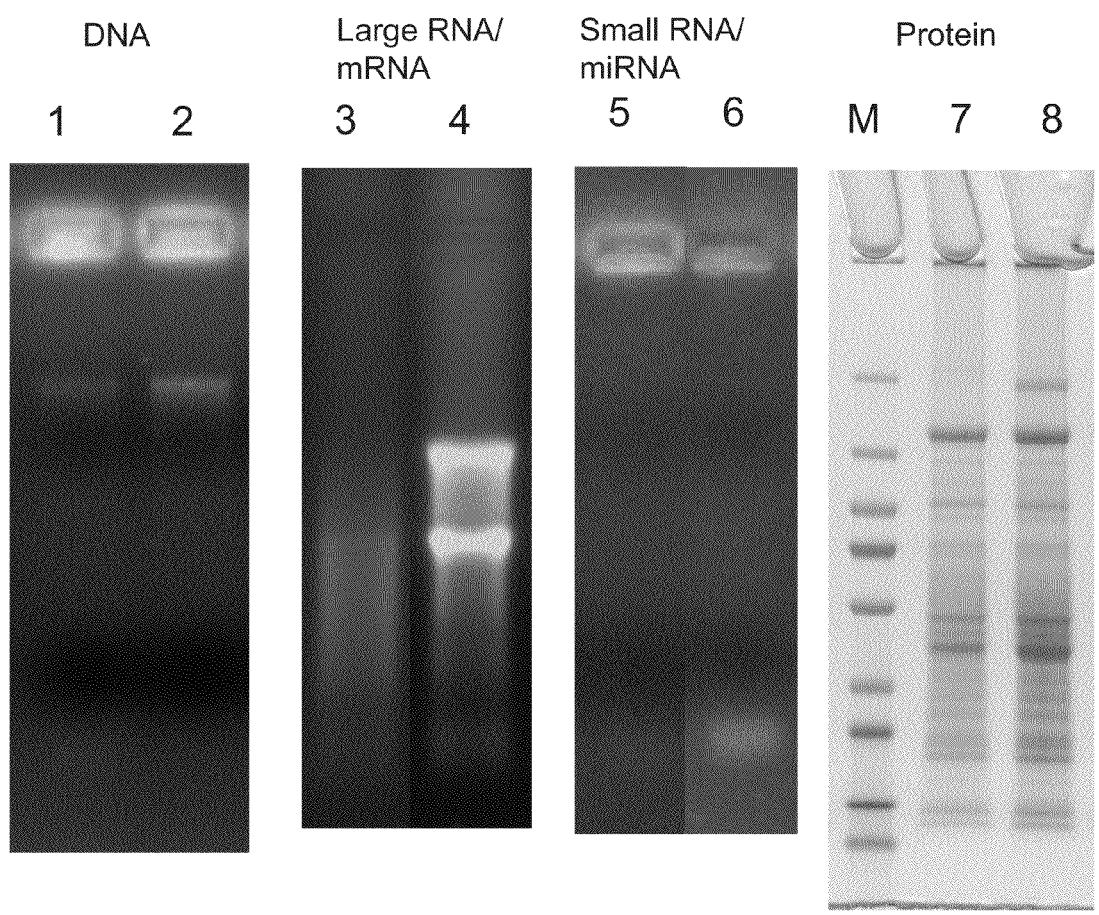
Fig 4. Protection of Biomolecules in specimens by the PLIS solution from the core module Fig 5. Protection of Biomolecules in lysate of specimens lysed by the PLIS solution from the core module
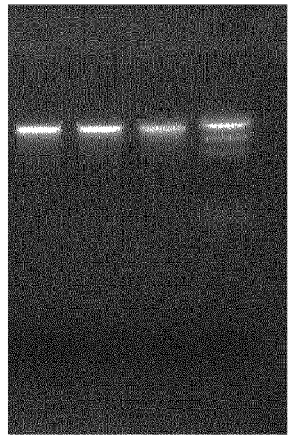
Panel A: DNA
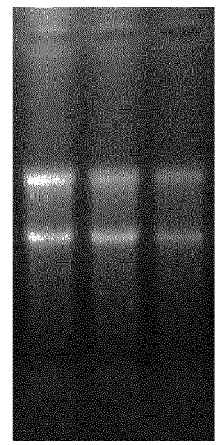
Panel B: Large RNA/mRNA
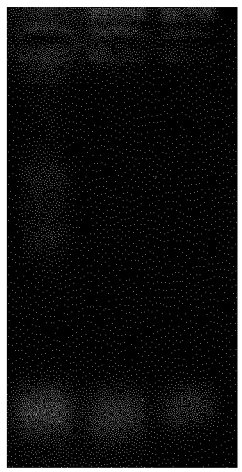
Panel C: Small RNA/miRNA
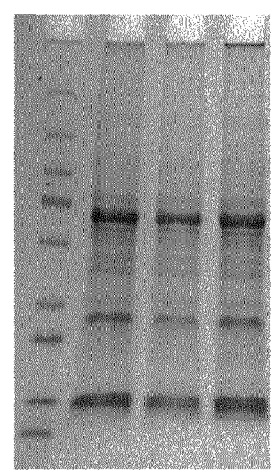
Panel D: Protein

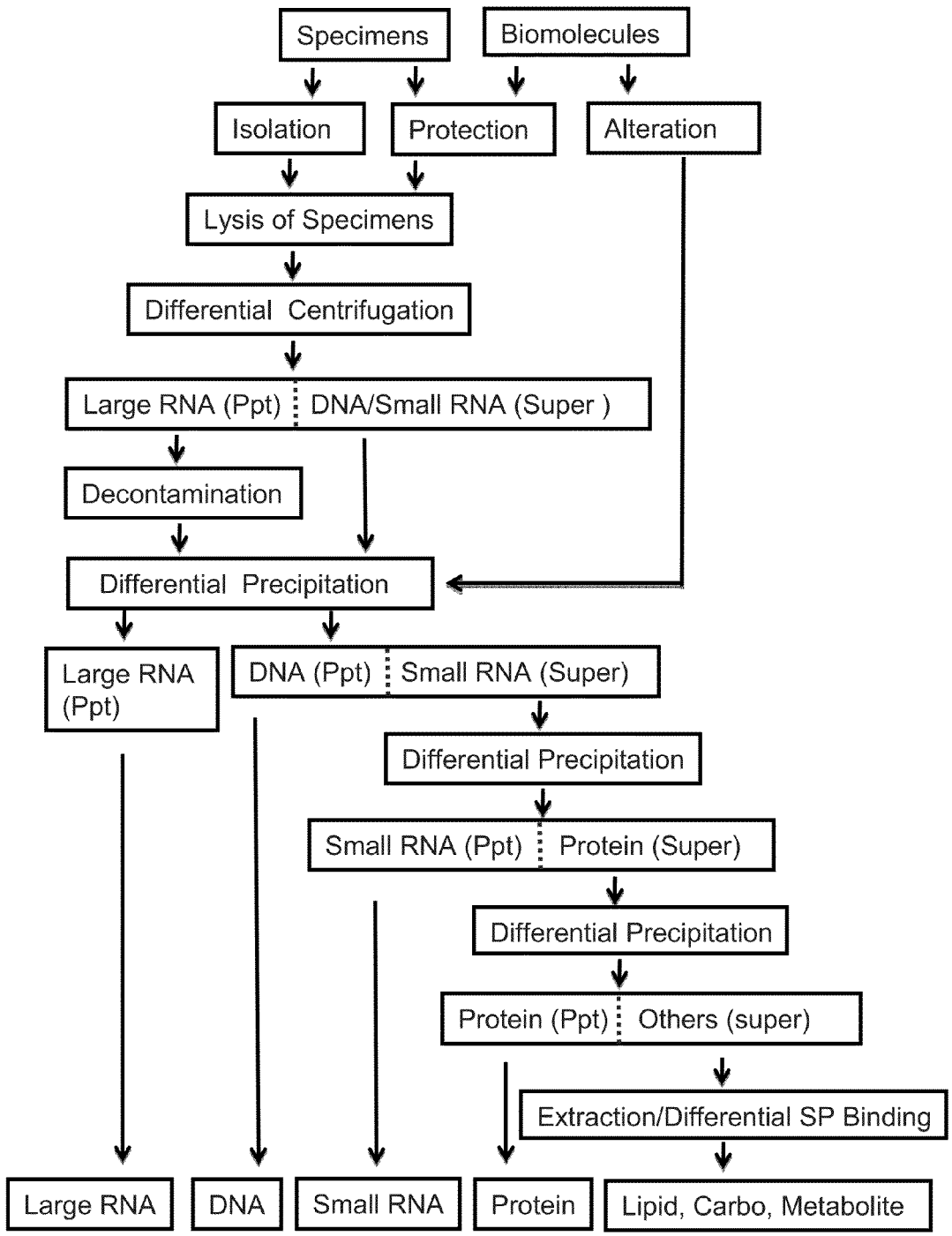
Fig 6. Integrated Versatile and Systems Preparation of Specimens: Overview of the core module with differential precipitation methods

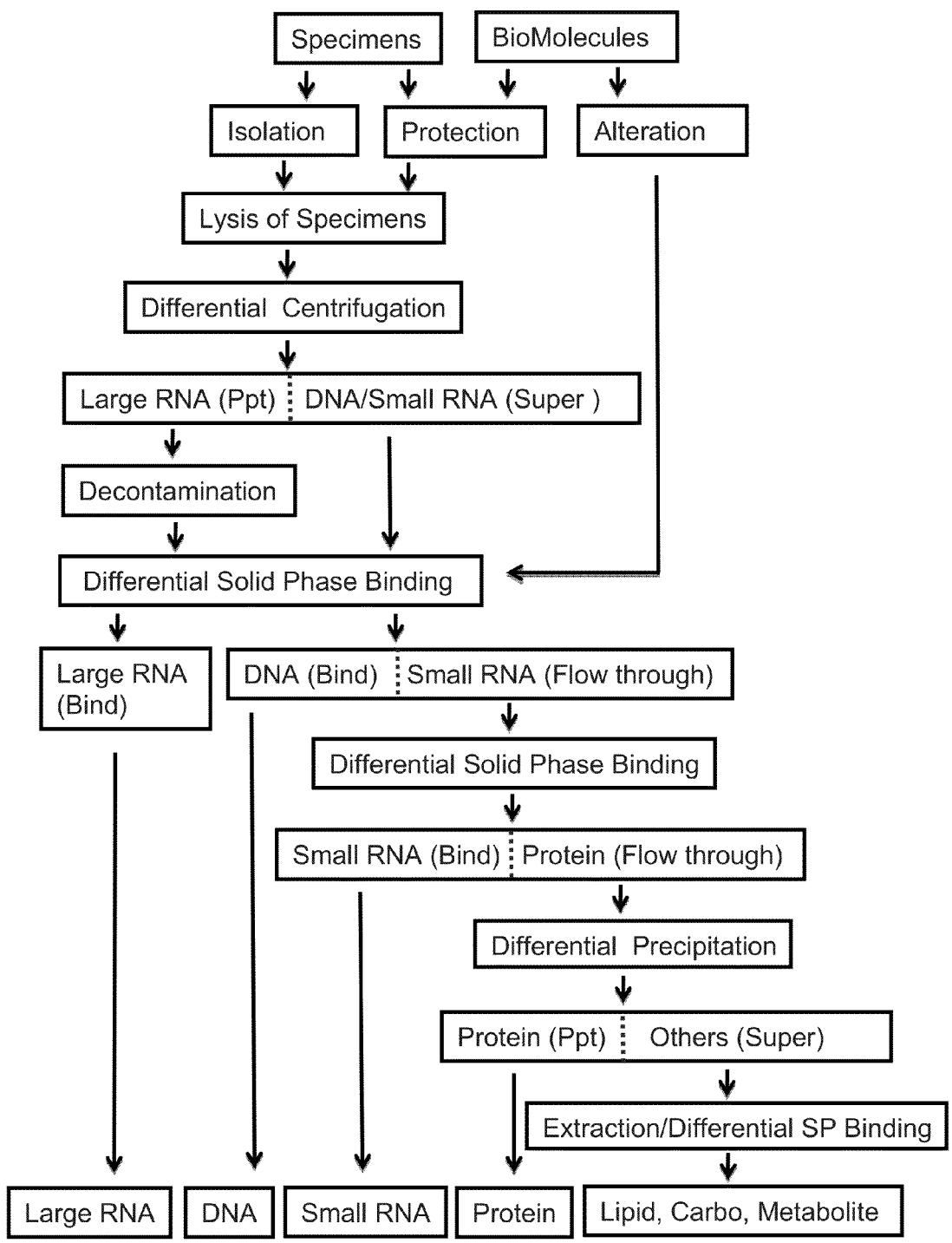
Fig 7. Integrated Versatile and Systems Preparation of Specimens: Overview of the core module plus differential solid phase binding method Fig. 8. Separation of Large RNA/mRNA from DNA with differential centrifugation and isolation of Large RNA/mRNA and DNA by differential precipitation methods (Panel A) or by differential solid phase binding methods (Panel B)
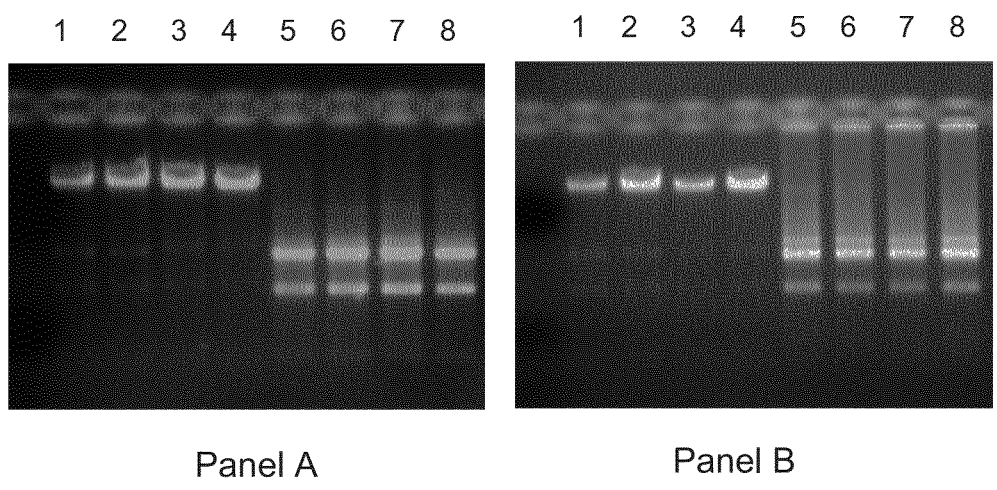
Panel A            Panel B Fig 9. Protocols for separation of DNA/ccfDNA, Large RNA/mRNA/ccfRNA, Small RNA/miRNA/ccfmiRNA, protein Lipid, carbohydrate, and metabolite from each other in different degrees by differential precipitation method

|    | PLIS | DAP | Ethanol | Biomolecules isolated |
|----|------|-----|---------|-----------------------|
| 1P | DiCen → | DeCon | 0% | Large RNA/mRNA/ccfRNA |
|    | ↓ | DiPpt | 31% | Large RNA/mRNA/ccfRNA |
|    | DiPpt | | 32% | DNA/ccfDNA |
|    | DiPpt | | 60% | Small RNA/miRNA/ccfmiRNA |
|    | DiPpt | | 90% | Protein |
|    | Ext/DiSPB | | | Lipid, carbohydrate, and metabolite |
| 2P | DiCen → | DeCon | 0% | Large RNA/mRNA/ccfRNA |
|    | ↓ | DiPpt | 31% | Large RNA/mRNA/ccfRNA |
|    | DiPpt | | 60% | DNA/ccfDNA/Small RNA/miRNA/ccfmiRNA |
|    | DiPpt | | 90% | Protein |
|    | Ext/DiSPB | | | Lipid, carbohydrate, and metabolite |
| 3P | DiPpt | | 32% | DNA/ccfDNA/Large RNA/mRNA/ccfRNA |
|    | → | DeCon | 0% | |
|    | ↓ | DiPpt | 60% | DNA/ccfDNA/Large RNA/mRNA/ccfRNA |
|    | DiPpt | | 60% | Small RNA/miRNA/ccfmiRNA |
|    | DiPpt | | 90% | Protein |
|    | Ext/DiSPB | | | Lipid, carbohydrate, and metabolite |
| 4P | DiPpt | | 60% | DNA/ccfDNA/Large RNA/mRNA/ccfRNA /Small RNA/miRNA/ccfmiRNA |
|    | → | DeCon | 0% | |
|    | ↓ | DiPpt | 60% | DNA/ccfDNA/Large RNA/mRNA/ccfRNA /Small RNA/miRNA/ccfmiRNA |
|    | DiPpt | | 90% | Protein |
|    | Ext/DiSPB | | | Lipid, carbohydrate, and metabolite |
| 5P | DiPpt | | 60% | DNA/ccfDNA/Large RNA/mRNA/ccfRNA /Small RNA/miRNA/ccfmiRNA |
|    | ↓ | | | |
|    | DiPpt | | 90% | Protein |
|    | Ext/DiSPB | | | Lipid, carbohydrate, and metabolite |

Note:
1. PLIS: PLIS solution from the core module   2. DAP: DAP solution from the core module
3. DiCen: Differential Centrifugation         4. DeCon: Decontamination
5. DiPpt: Differential Precipitation          6. DiSPB: Differential Solid Phase Binding
7. Ext: Extraction
8. 1P, 2P, 3P, 4P and 5P: Protocols with different Degrees for separation of DNA/ccfDNA, Large RNA/mRNA/ccfRNA, Small RNA/miRNA/ccfmiRNA, and protein from each other Fig 10. Protocols for separation of DNA/ccfDNA, Large RNA/mRNA/ccfRNA, Small RNA/miRNA/ccfmiRNA, protein Lipid, carbohydrate, and metabolite from each other in different degrees by differential solid phase binding method

|    | PLIS | DAP | Ethanol | Biomolecules Isolated |
|----|------|-----|---------|------------------------|
| 1B | DiCen → | DeCon | 0% | Large RNA/mRNA/ccfRNA |
|    | ↓ | DiSPB | 32% | Large RNA/mRNA/ccfRNA |
|    | DiSPB |  | 40% | DNA/ccfDNA |
|    | DiSPB |  | 60% | Small RNA/miRNA/ccfmiRNA |
|    | DiPpt |  | 90% | Protein |
|    | Ext/DiSPB |  |  | Lipid, carbohydrate, and metabolite |
| 2B | DiCen → | DeCon | 0% | Large RNA/mRNA/ccfRNA |
|    | ↓ | DiSPB | 32% | Large RNA/mRNA/ccfRNA |
|    | DiSPB |  | 60% | DNA/ccfDNA/Small RNA/miRNA/ccfmiRNA |
|    | DiPpt |  | 90% | Protein |
|    | Ext/DiSPB |  |  | Lipid, carbohydrate, and metabolite |
| 3B | 1. DiSPB |  | 40% | DNA/ccfDNA/Large RNA/mRNA/ccfRNA |
|    | or 2. DiPpt |  | 32% |  |
|    |  → | DeCon | 0% |  |
|    | ↓ | DiSPB | 60% | DNA/ccfDNA/Large RNA/mRNA/ccfRNA |
|    | DiSPB |  | 60% | Small RNA/miRNA/ccfmiRNA |
|    | DiPpt |  | 90% | Protein |
|    | Ext/DiSPB |  |  | Lipid, carbohydrate, and metabolite |
| 4B | DiPpt |  | 60% | DNA/ccfDNA/Large RNA/mRNA/ccfRNA /Small RNA/miRNA/ccfmiRNA |
|    |  → | DeCon | 0% |  |
|    | ↓ | DiSPB | 60% | DNA/ccfDNA/Large RNA/mRNA/ccfRNA /Small RNA/miRNA/ccfmiRNA |
|    | DiPpt |  | 90% | Protein |
|    | Ext/DiSPB |  |  | Lipid, carbohydrate, and metabolite |
| 5B | DiSPB |  | 60% | DNA/ccfDNA/Large RNA/mRNA/ccfRNA /Small RNA/miRNA/ccfmiRNA |
|    | ↓ |  |  |  |
|    | DiPpt |  | 90% | Protein |
|    | Ext/DiSPB |  |  | Lipid, carbohydrate, and metabolite |

Note:
1. PLIS: PLIS solution from the core module   2. DAP: DAP solution from the core module
3. DiCen: Differential Centrifugation          4. DeCon: Decontamination
5. DiPpt: Differential Precipitation           6. DiSPB: Differential Solid Phase Binding
7. Ext: Extraction
8. 1B, 2B, 3B, 4B and 5B: Protocols with different Degrees for separation of DNA/ccfDNA, Large RNA/mRNA/ccfRNA, Small RNA/miRNA/ccfmiRNA, and protein from each other

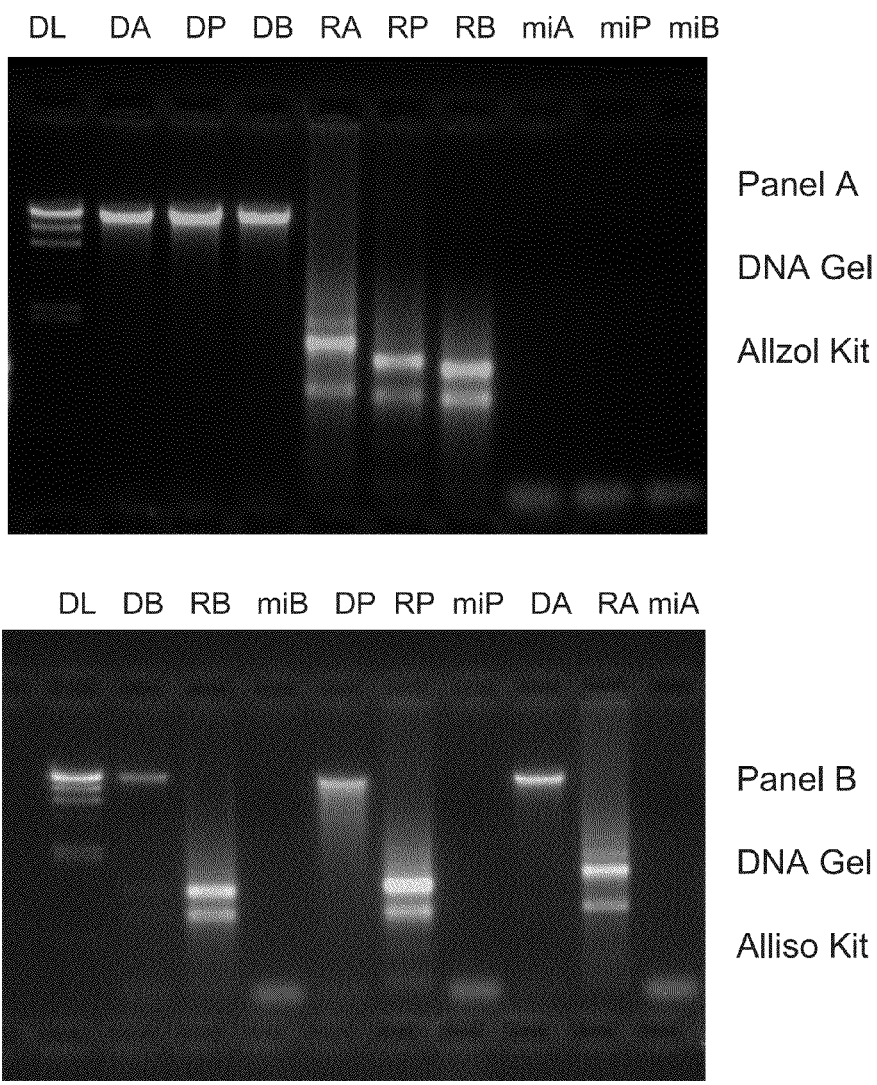
Fig 11. Isolation of DNA, Large RNA/mRNA, Small RNA/miRNA and Protein from bacteria, plant and animal tissue by Allzol Kit or by Alliso Kit (Panel A and B)

Fig 11. Isolation of DNA, Large RNA/mRNA, Small RNA/miRNA and Protein from bacteria, plant and animal tissue by Allzol Kit or by Alliso Kit (Panel C and D)
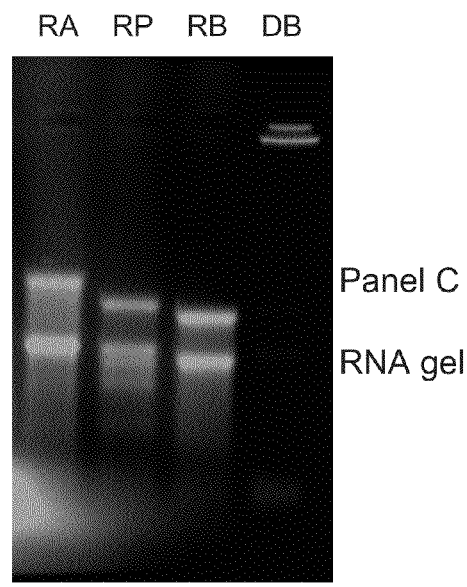
Panel C
RNA gel
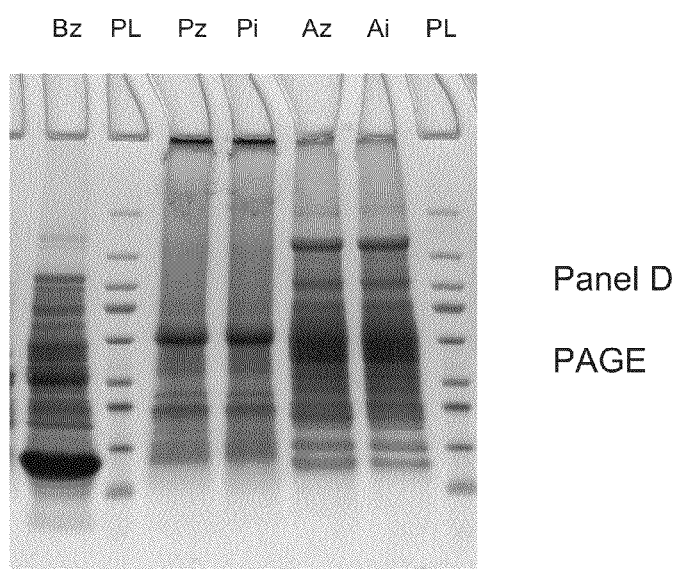
Panel D
PAGE

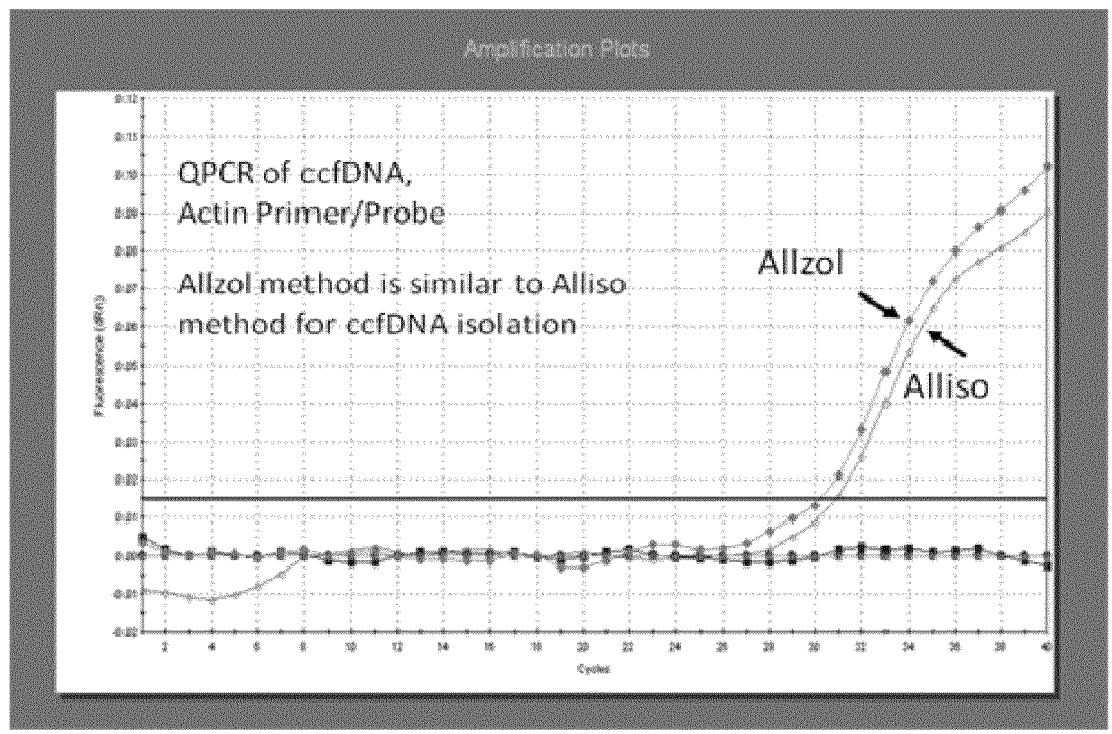
Fig 12 . QPCR of ccfDNA isolated from human serum with Actin Primer/Probe. The ccfDNA was isolated with Allzol Kit or Alliso Kit. Both Kits show similar result

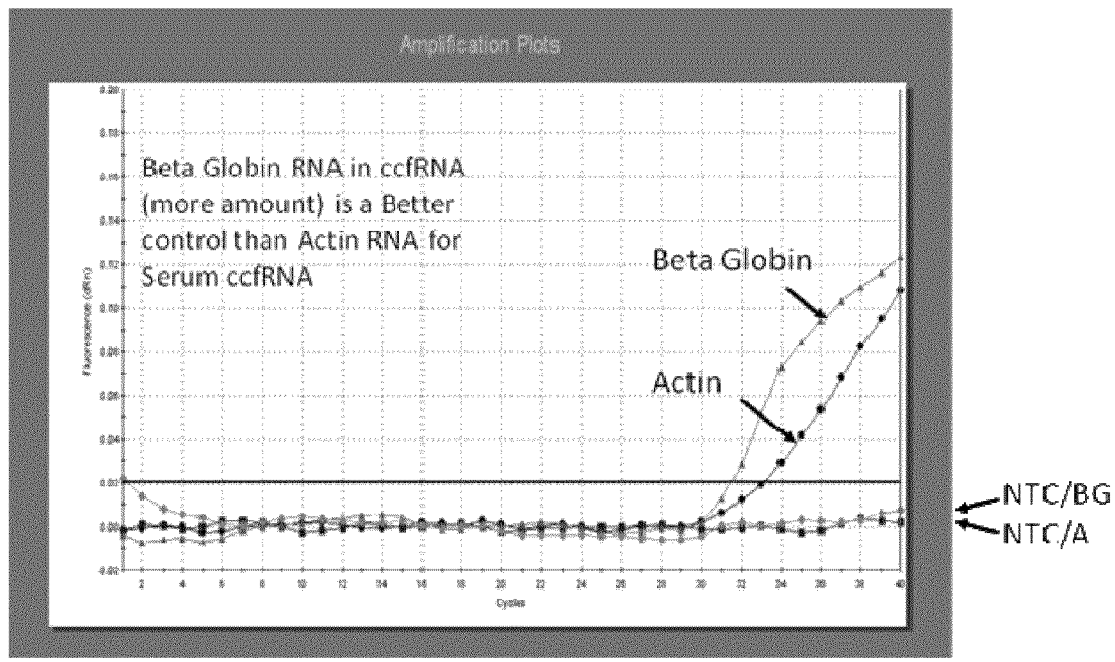
Fig 13. QRT-PCR of ccfRNA isolated from serum with Beta Globin or Actin primer/probe. The ccfRNA was isolated with Allzol Kit. Beta Globin is a better internal control

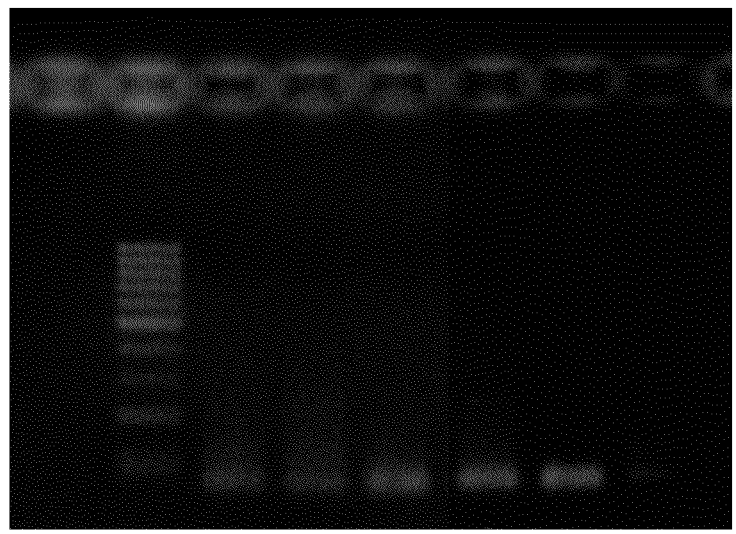
Fig 14. Agarose gel electrophoresis of QRT-PCR product of ccfmiRNA with mir24 primer/probe
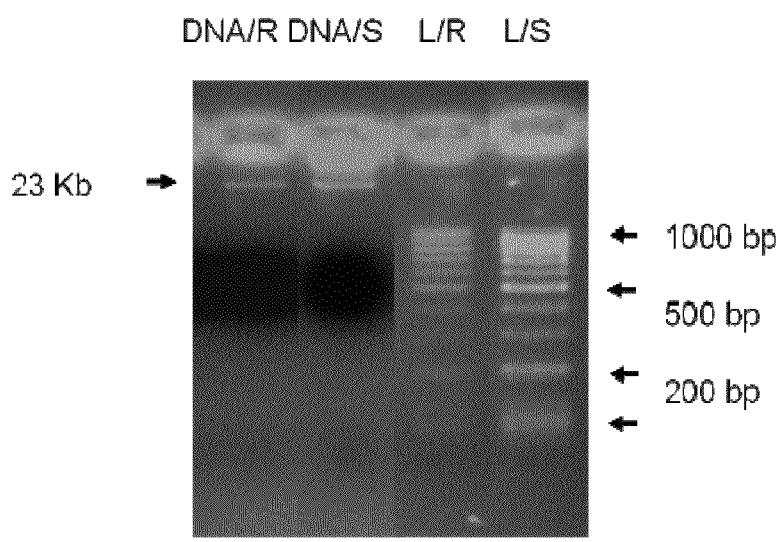
Fig 15. Agarose gel electrophoresis of recovered DNA from Agarose gel and DNA before recovery

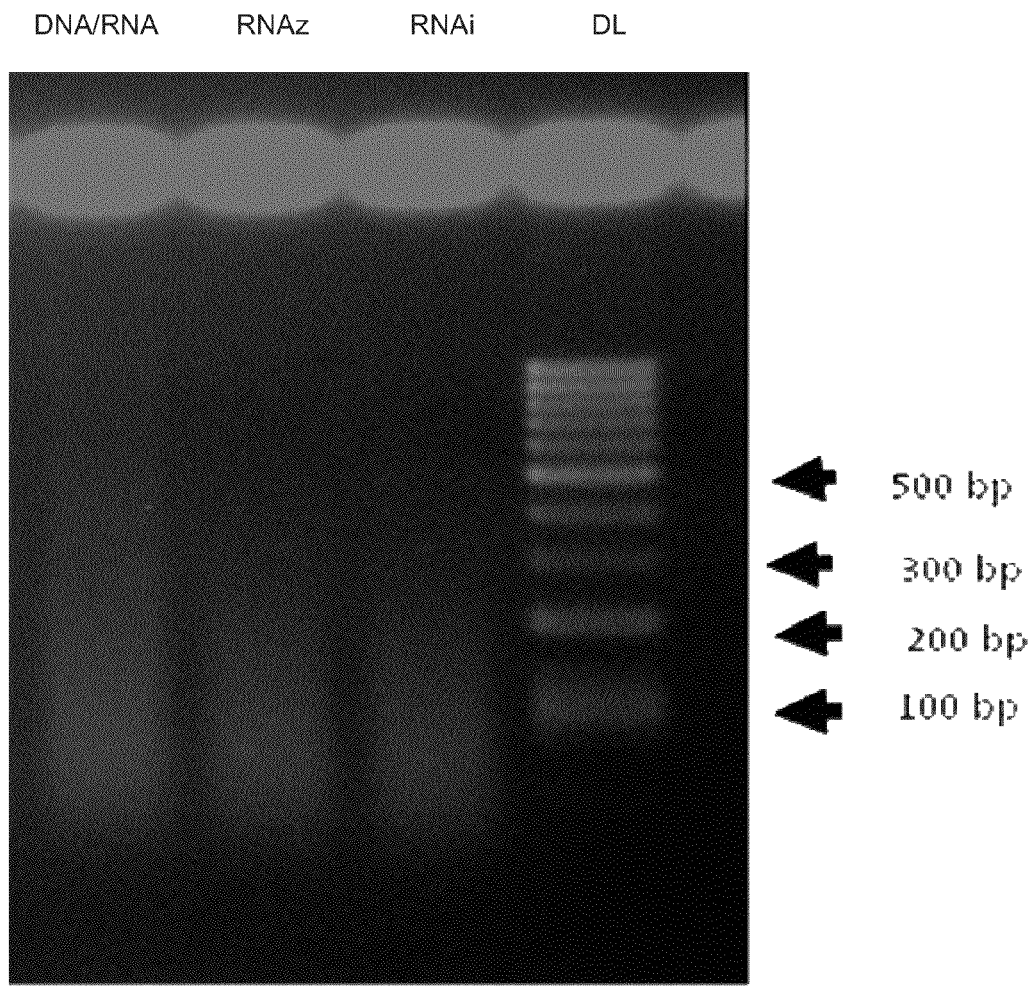
Fig 16 . Agarose gel Electrophoresis analysis of DNA/RNA and RNA/miRNA isolated from FFPE tissue sections

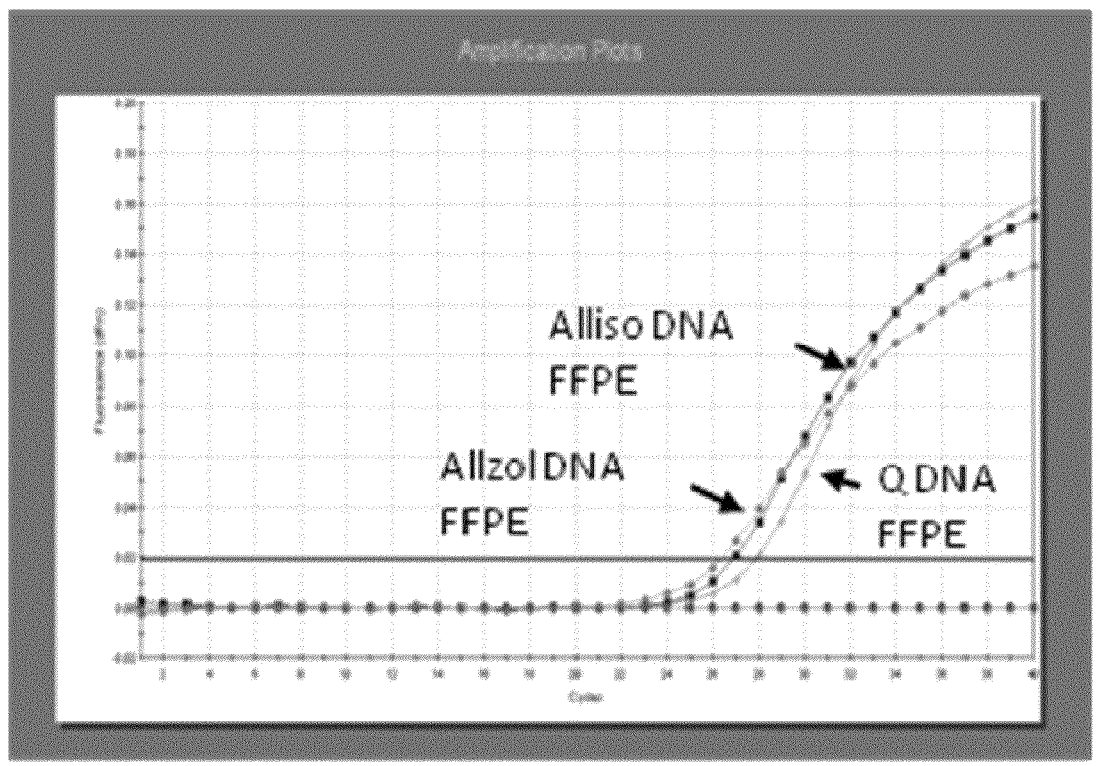
Fig 17. Quantitative PCR (QPCR) for FFPE DNA. Comparison of FFPE DNA isolated by Allzol Kit, Alliso Kit and Kit from market leader Q by QPCR with Actin primer and probe

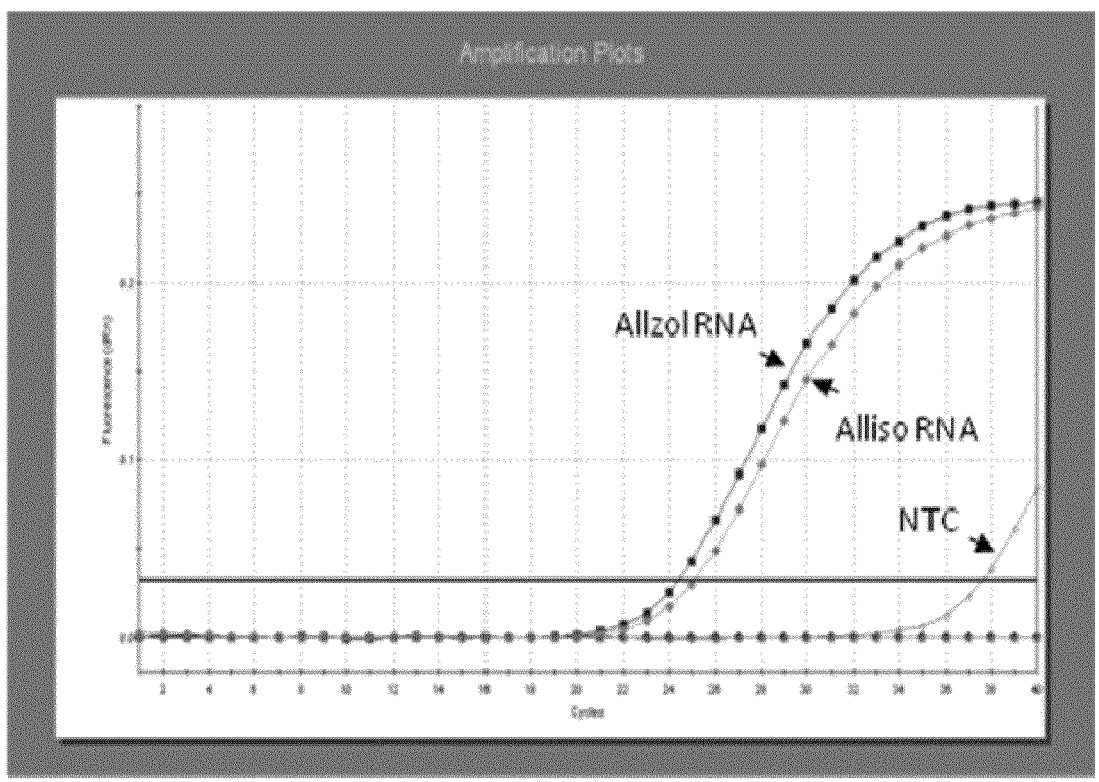
Fig 18 . Quantitative Real Time PCR (QRT-PCR) for FFPE RNA/miRNA.
Comparison of FFPE RNA isolated by Allzol Kit and Alliso kit by QRT-PCR with
Actin primer and probe

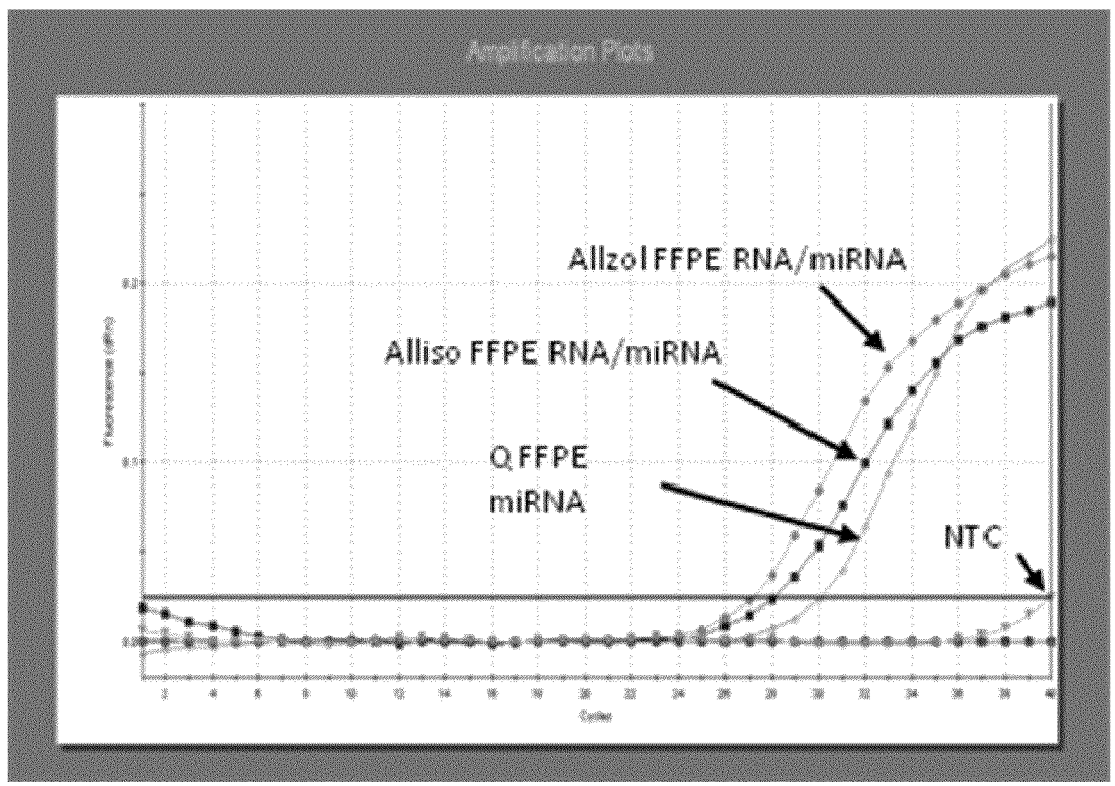
Fig 19 . Quantitative Real Time PCR (QRT-PCR) for FFPE miRNA. Comparison of FFPE RNA/miRNA isolated by Allzol Kit, Alliso Kit and kit from market leader Q by QRT-PCR with mir24 primer and probe

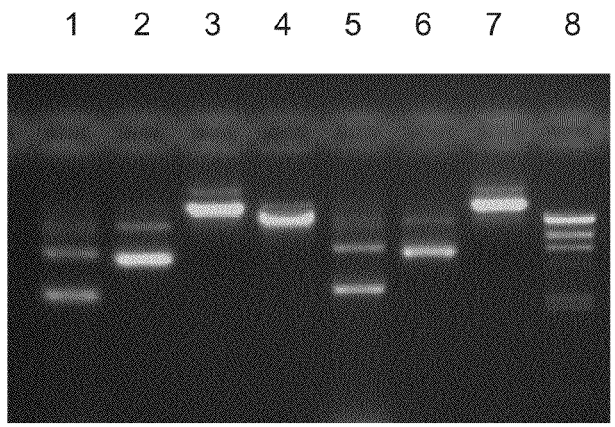
Fig 20. Agarose gel electrophoresis of plasmid DNA isolated from bacteria by Allzol Kit or Alliso Kit
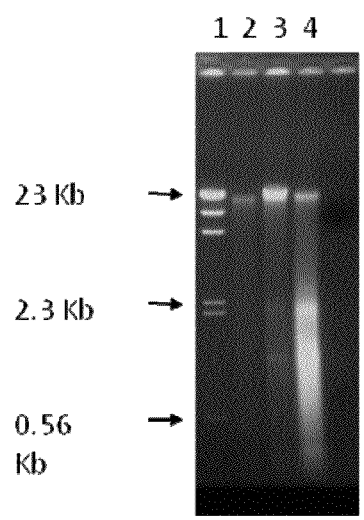
Fig. 21. Agarose gel electrophoresis of Mitochondria DNA and Nucleic DNA isolated by Allzol Kit
Lane 1: DNA Ladder Lambda Hind III
Lane 2: Mitochondria DNA
Lane 3: Nucleic DNA
Lane 4: DNA and RNA in Supernatant

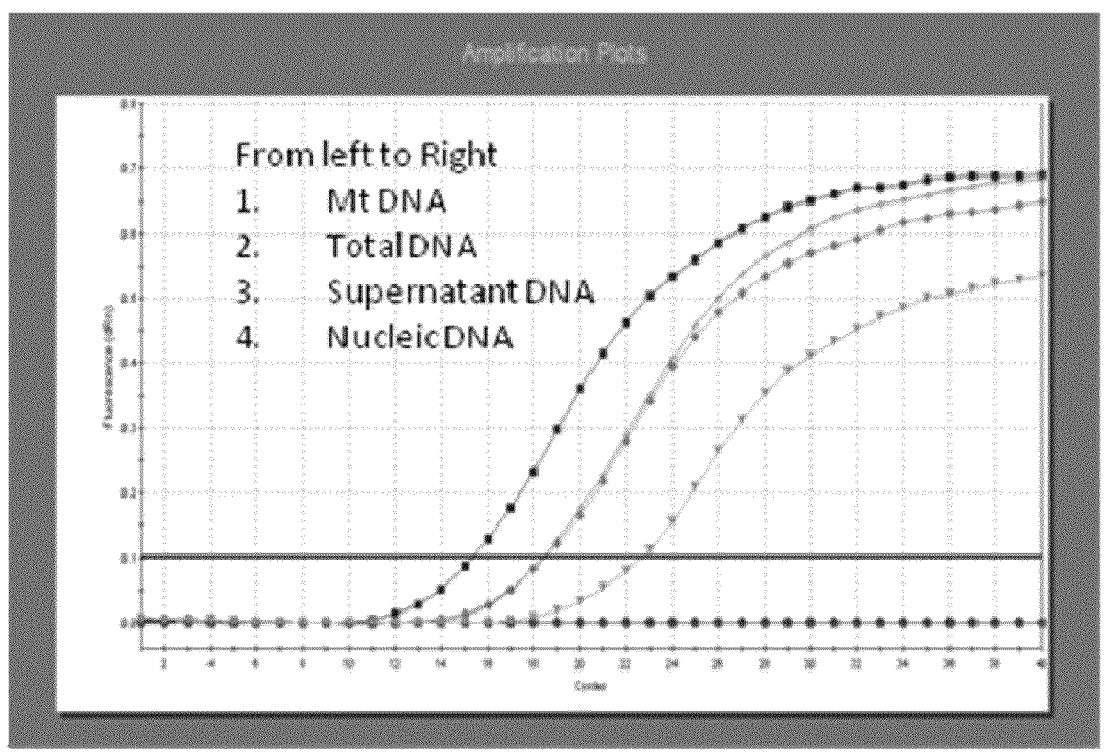
Fig 22 . QPCR of Mitochondria DNA and Nucleic DNA with Cyto B primer

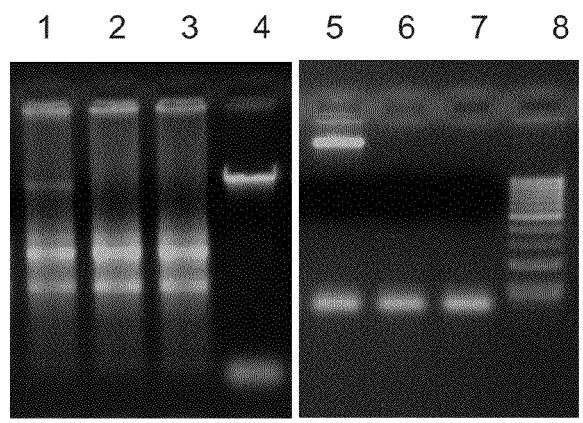
Fig 23. Agarose gel electrophoresis of RNA and miRNA with removal of DNA by Allzol or Alliso Kit

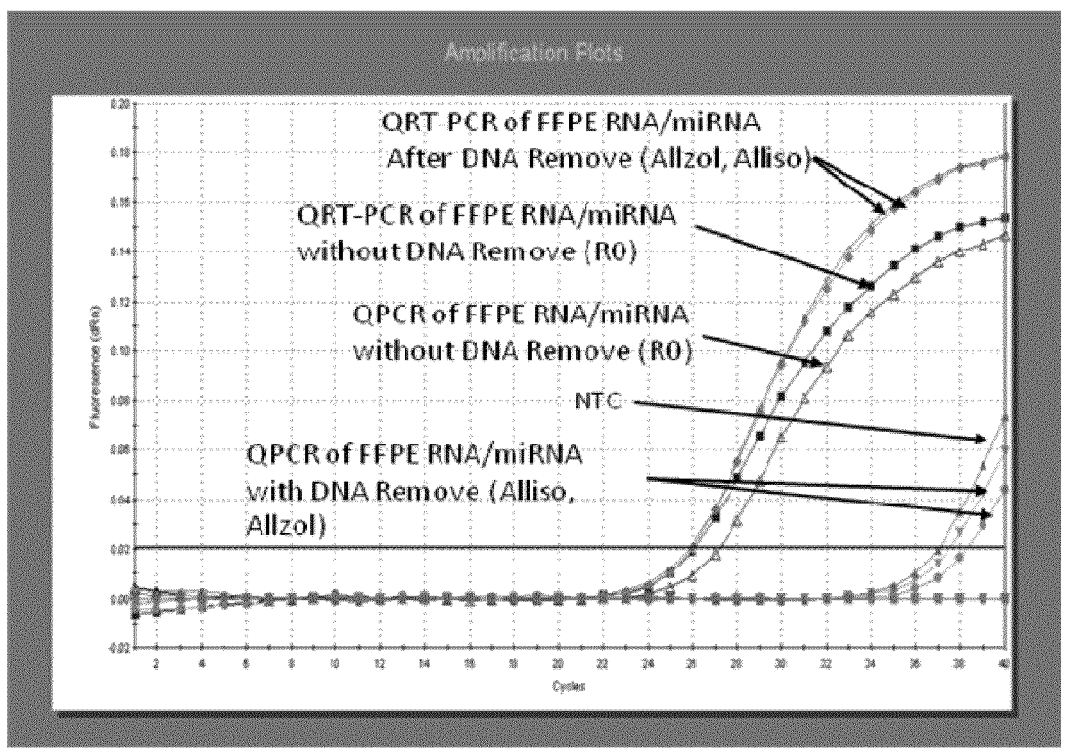
Fig 24. QPCR and QRT-PCR of FFPE DNA or FFPE RNA/miRNA with removal of DNA by Allzol or Alliso Kit

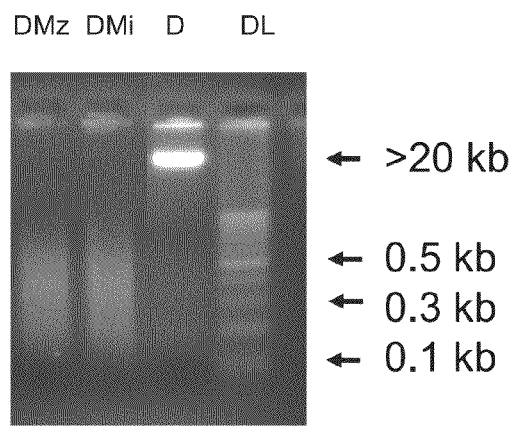
Fig 25. DNA fragmentation by DNA Mincer
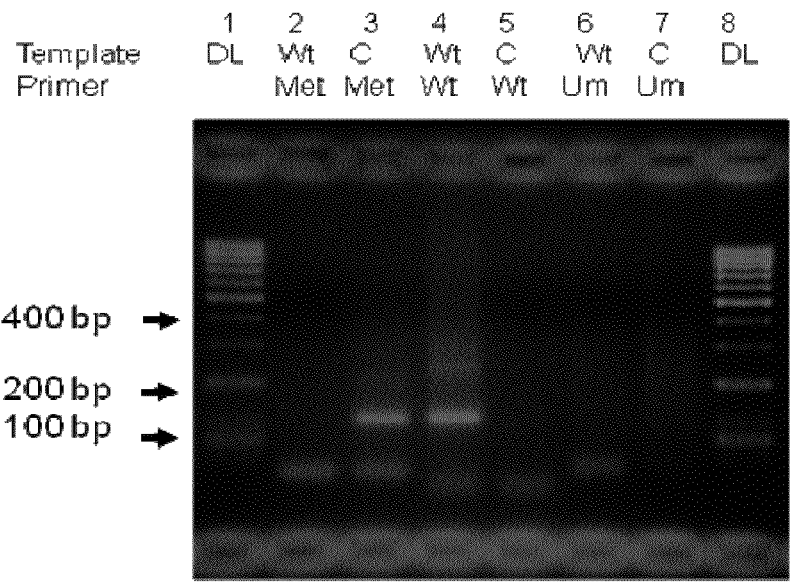
Fig 26. Agarose gel electrophoresis of PCR product from converted DNA and wild type (unconverted) DNA with Methylation primer, Unmethylation primer or wild type primer

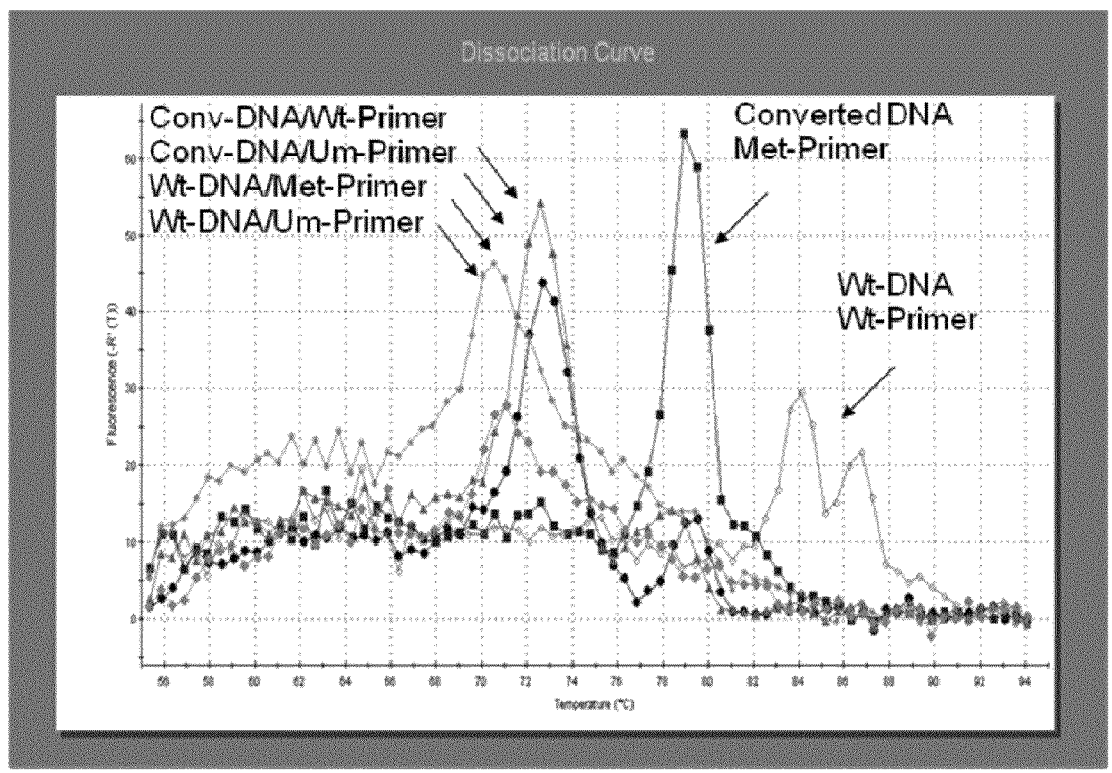
Fig 27. QPCR of Converted and wild type (unconverted) DNA with Methylation primer, Unmethylation primer or wild type primer Fig 28. High yield and quality of DNA and RNA isolated by Allzol Kit and Alliso Kit compared with the market leaders Q and I
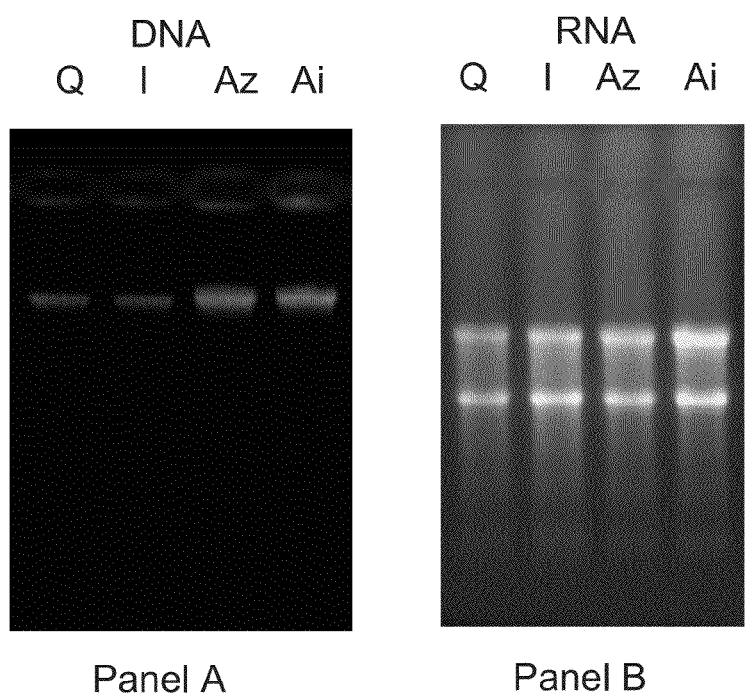

Fig 29. Better stability and quality of the RNA isolated by Allzol Kit and Alliso Kit compared with market leaders Q and I
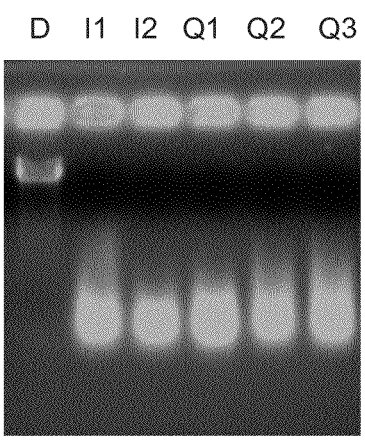
Panel A
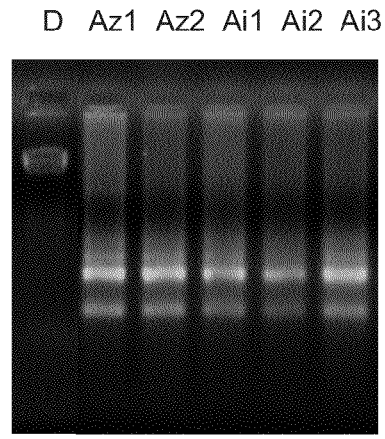
Panel B
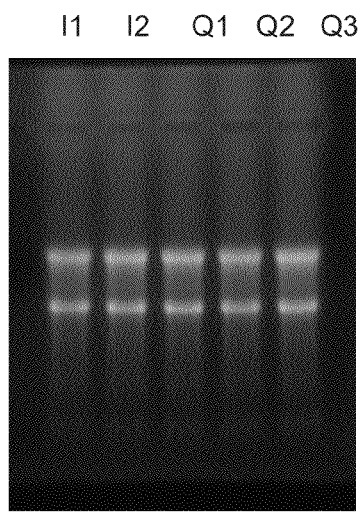
Panel C
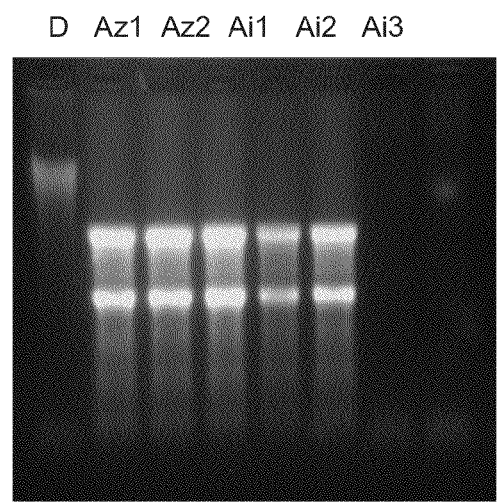
Panel D

INTEGRATED VERSATILE KIT FOR ISOLATING COMPONENTS IN BIOLOGICAL SAMPLES

CROSS REFERENCE TO RELATED APPLICATIONS

This application is a divisional application and claims priority to U.S. patent application Ser. No. 12/979,383 filed on 28 Dec. 2010, now allowed. The pending U.S. application Ser. No. 12/979,383 is hereby incorporated by reference in its entireties for all of its teachings.

FIELD OF INVENTION

This invention relates the methods and kits for preparation of specimens, which integrates synchronously the methods of protection, isolation and alteration of specimens and biomolecules into "One for All" product or kit for systems preparation of biomolecules including DNA/ccfDNA, Large RNA/mRNA/ccfRNA, Small RNA/miRNA/ccfmiRNA, Protein, Lipid, Carbohydrates, and Metabolite simultaneously or individually from a variety of specimens including solid specimens (animal tissue, cell, plant tissue, and microorganism) and liquid specimens (plasma, serum, whole blood, biofluid).

BACKGROUND OF INVENTION

Current methods and kits for preparation of specimens, especially for protection, isolation and alteration of specimens and biomolecules contains some major and key components such as the chemicals in high concentration, toxic organic reagents, and solid phase binding materials. There are many methods and kits for a great variety of specimens and biomolecules. For examples, in aspects of protection of specimens and biomolecules, using ammonium sulfate in high concentration to protect integrity of RNA (U.S. Pat. No. 6,204,375); using toxic formaldehyde to protect histological structure and micromorphology of tissue specimens. In aspects of isolation of biomolecules from specimens, using organic reagents such as phenol and chloroform to isolate RNA (U.S. Pat. No. 5,346,994); using solid phase binding materials to isolate biomolecules; using many different methods and kits to isolate biomolecules including DNA/ccfDNA, Large RNA/mRNA/ccfRNA, Small RNA/miRNA/ccfmiRNA, Protein, Lipid, Carbohydrates, and Metabolite from the same specimen; and using many different methods and kits to isolate biomolecules from a variety of specimens including solid specimens, liquid specimens, chemical or enzymatic reaction specimens, gel slice specimens containing biomolecules, and contaminated or over-diluted specimens.

But, there are some drawbacks in current methods and kits for preparation of specimens. The too many methods and kits are individually separated, limited to and focus specifically for a particular function and application. While in protection of specimens and biomolecules, ammonium sulfate in high concentration can protect integrity of RNA, but cannot protect the histological structure and micromorphology of tissue specimens; toxic formaldehyde can protects histological structure and micromorphology of tissue specimens but can also cause the degradation of biomolecule inside protected specimens. While in isolation of biomolecules from specimens, organic reagents such as phenol and chloroform are toxic to users and environment; solid phase binding materials waste economical and natural resources. While in isolation of different biomolecules from the same specimen, it demands large amount of specimen and uses many different methods and kits for different biomolecules. While in isolation of biomolecules from the different specimen, it uses many different methods and kits for a variety of specimens. The many current methods and kits for preparation of specimens are not designed for integration, interaction or sharing each other. There is almost no possibility to establish a core method and kit to cover most functions and applications in preparation of specimen and to extend the extra functions and applications to many other particular specimens and biomolecules.

Although there are many years of application and continuous researches in current methods and kits for preparation of specimens, there are still too many of current methods and kits for preparation of different specimens and biomolecules, due to the fact that each individual method and kit only use the optimized chemicals and materials particularly for the specific function and application of the method and kit itself, and no or less effort is focused on integration, interaction and sharing the components, functions and applications among the current methods and kits. Up to date, it is not available for chemicals, methods and kits that can protect the histological structure and micromorphology of tissue specimens and also protect integrity of biomolecules; it is not available for chemicals, methods and kits that can protect the protect integrity of biomolecules and also isolate biomolecules; it is not available for chemicals, methods and kits that isolate biomolecules directly from protection agents for specimens and biomolecules. It is not available for chemicals, methods and kits that can remove toxic chemicals or reagents for protection and isolation of specimens and biomolecules. Duo to incompatibility among the chemicals, methods and kits aforementioned, it is not available for a method and kit that can integrate different methods and kits that can prepare different specimens and different biomolecules; it is not available for a method and kit that can isolate biomolecules including DNA/ccfDNA, Large RNA/mRNA/ccfRNA, Small RNA/miRNA/ccfmiRNA, protein, lipid, carbohydrate, and metabolite simultaneously from the same specimen; it is not available for a method and kit that can isolate biomolecules from a variety of specimens including solid specimens, liquid specimens, chemical or enzymatic reaction specimens, gel slice specimens containing biomolecules, and contaminated or over-diluted specimens by itself; it is not available for a method and kit that can serve as a core method and kit to cover most functions and applications in preparation of specimen and to extend the extra functions and applications to many other particular specimens and biomolecules including isolation of biomolecules from formalin fixed and paraffin embedded (FFPE) tissue sections, isolation of mitochondria DNA and nucleic DNA from mitochondria and nuclei, isolation of plasmid DNA from bacteria, elimination of DNA from RNA, conversion of DNA for methylation analysis, preparation of DNA fragments, DNA labeling and RNA labeling. Therefore, current methods and kits still use toxic chemicals that hurt users and environment. More and more methods and kits with different chemicals and formats for preparation of different specimens and different biomolecules are existed and coming out continuously that bother the users' selections for choosing the methods and kits, and waste the economical and natural resources.

This invention is created for overcoming the drawbacks current methods and kits for preparation of specimens aforementioned and provides a method and kit for preparation of specimens and biomolecules. The invention provides the methods and kits for preparation of specimens and biomolecules as follows: the methods and kits for preparation of specimens and biomolecules without involving phenol and chloroform; One solution that can integratively protect, isolate and alter the specimens and biomolecules and subsequently isolate biomolecules directly from the specimens in the protection agents for specimens and biomolecules; One method and kit can versatilely isolate biomolecules from a variety of specimens including solid specimens, liquid specimens, chemical or enzymatic reaction specimens, gel slice specimens containing biomolecules, and contaminated or over-diluted specimens by itself; One method and kit can systematically isolate biomolecules including DNA/ccfDNA, Large RNA/mRNA/ccfRNA, Small RNA/miRNA/ccfmiRNA, protein, lipid, carbohydrate, and metabolite simultaneously from the same specimen; One method and kit can serve as a core method and kit to cover most functions and applications in preparation of specimen and to extend the extra functions and applications to many other particular specimens and biomolecules including isolation of biomolecules from formalin fixed and paraffin embedded (FFPE) tissue sections, isolation of mitochondria DNA and nucleic DNA from mitochondria and nuclei, isolation of plasmid DNA from bacteria, elimination of DNA from RNA, conversion of DNA for methylation analysis, preparation of DNA fragments, DNA labeling and RNA labeling.

This invention of Integrated Versatile and Systems Preparation of Specimens (Samples) relates an open module technology and system which integrates synchronously the methods of protection, isolation and alteration of specimens into one product or kit. The "One for All" product or kit comprises a core module without or with plug-in modules and a set of comprehensive protocols for systems preparation of biomolecules including DNA/ccfDNA, Large RNA/mRNA/ccfRNA, Small RNA/miRNA/ccfmiRNA, Protein, Lipid, Carbohydrates, and Metabolite simultaneously or individually from a variety of specimens including solid specimens (animal tissue, cell, plant tissue, and bacteria) and liquid specimens (plasma, serum, whole blood, biofluid).

The core module can accept and adopt new or custom Plug-in modules for expanding the functions or applications for Integrated Versatile and Systems Preparation of Specimen through open module technology. The systems biomolecules prepared from Integrated Versatile and Systems Preparation of Specimens have broad applications in systems pathology, systems diagnostics, systems medicine, systems biology and associated disciplines, as well as in conventional biomedical disciplines. The product or kit supported by the open module technology and system prepares biomolecules with high quality with the features and benefits of easy to use, fast, no toxic materials, safe to user and environment, low demanding on the materials and labors, sharing modules among users, cost-effective, saving budget, reducing waste, saving nature resources and environment and leading to a low-carbon and Green economy in preparation of specimens.

The terminology of systems preparation of biomolecules in this invention derives from Systems theory. Systems theory is a trans-disciplinary approach that abstracts and considers a system as a set of independent and interacting parts. Systems Pathology, systems diagnostics, systems medicine and systems biology are the terms used to describe a number of applications and studies in life science. They are life science based inter-disciplinary application and research fields that focus on complex interactions in life systems, claiming that they use holism perspectives instead of reductive perspectives. For examples, in reductive perspective, the accountable biomarkers for conventional diagnostics of diseases are pursued down to the details as a single nucleotide polymorphism (SNP) in genomic DNA, a change of expression pattern in one mRNA, or a reconfiguration of protein molecule; One amino acid change in a protein is used as diagnostic marker but without consideration of changes in mRNA and DNA as cause of the diseases, or changes in lipid, carbohydrate or metabolite as results of the diseases. In systems diagnostics with holism perspective, the amino acid change in a protein is considered as one part of the disease, the mRNA expression and the DNA was studied for the cause of disease, the changes in lipid, carbohydrate or metabolite are studies for the results of the disease; The cause of the disease can be in the immune system and symptoms are from neural system, digest system or urinary system.

With systems preparation of specimens, the disease was studied in inter-disciplinary field such as molecular biology, biochemistry, physiology or pathology. The complex interactions in life systems involve neural system, digest system and urinary system. With the systems diagnostics on the biomolecules of DNA, mRNA, miRNA, Protein, lipid, carbohydrate or metabolite, the approaches of systems medicine, such as therapeutics, treatment, prevention, prediction, prognostication, and participation, are used to deal with the disease. Unfortunately, the biomolecules isolated individually, irrespectively, irrelevantly, randomly, or asynchronously by conventional preparation methods are hardly fulfill the demands on systems biomolecules for systems diagnostics. Therefore, the systems preparations of systems biomolecules including DNA/ccfDNA, Large RNA/mRNA/ccfRNA, Small RNA/miRNA/ccfmiRNA, Protein, lipid, carbohydrate or metabolite simultaneously (or individually if necessary) from the specimens by this invention are very critical for systems diagnostics and systems medicine.

In this invention Integrated Preparation of Specimens integrates synchronously the three methods of preparation, protection, isolation and alteration of specimen and biomolecules in one product or Kit. Conventionally, the preparation methods of protection, isolation and alteration are carried out separately, individually, irrelevantly, irrespectively or asynchronously in different product or kit. Such a complicated mission was achieved through open module technology in this invention. The open module technology includes three major elements, the core module, the plug-in modules, and emerging and custom plug-in modules. The core module plays the leading role and major functions/applications of the Integrated Versatile and Systems Preparation of Specimens. The plug-in modules extend and broaden the functions/applications of the core module. The plug-in modules are designed and act as plug-and-play modules for the core modules. The core module is designed to accept and adopt emerging and custom plug-in modules, which allows inventor to add more plug-in modules or users to add their special plug-in modules with custom requests. The product or kit derived from the core module has multiple functions/applications of many conventional products or Kits. With products or kits derived from plug in modules the core module has a vast variety of functions/applications in almost all conventional products or Kits.

For examples, each conventional kit for specimen preparation only specifically prepares one type of biomolecule, such as DNA isolation Kit for preparation of DNA only. Different types of conventional kits for specimen preparation are required for preparation different types of biomolecules, such as RNA isolation kit, miRNA isolation kit and protein isolation kit. The protection of specimen is carried out by other kit, such as tissue preservation kit, and alteration of biomolecules will be conducted by another kit, such as DNA conversion kit for methylation analysis. Total six kits are required for above jobs of protection, isolation and alteration. In this invention one kit with core module and one plug-in module will complete these jobs. If users want to prepare circulating cell free (ccf) DNA, ccfRNA and ccfmiRNA from plasma for their project, another three kits are required if they use conventional kits, which accumulates to total nine kits for nine jobs. But with this invention, they can use the extra functions of the same kit for prepare ccfDNA, ccfRNA and ccfmiRNA from plasma. The one kit in this invention is same as nine conventional kits in this example. The Integrated Versatile and Systems Preparation of Specimens integrates the complicated missions with many different kits into state of art, One Kit for All.

SUMMARY OF THE INVENTION

There are some drawbacks in current methods and kits for preparation of specimens. The too many methods and kits are individually separated, limited to and focus specifically for a particular function and application. While in protection of specimens and biomolecules, ammonium sulfate in high concentration can protect integrity of RNA, but cannot protect the histological structure and micromorphology of tissue specimens; toxic formaldehyde can protects histological structure and micromorphology of tissue specimens but can also cause the degradation of biomolecule inside protected specimens. While in isolation of biomolecules from specimens, organic reagents such as phenol and chloroform are toxic to users and environment; solid phase binding materials waste economical and natural resources. While in isolation of different biomolecules from the same specimen, it demands large amount of specimen and uses many different methods and kits for different biomolecules. While in isolation of biomolecules from the different specimen, it uses many different methods and kits for a variety of specimens. The many current methods and kits for preparation of specimens are not designed for integration, interaction or sharing each other. There is almost no possibility to establish a core method and kit to cover most functions and applications in preparation of specimen and to extend the extra functions and applications to many other particular specimens and biomolecules.

This invention is created for overcoming the drawbacks current methods and kits for preparation of specimens aforementioned and provides a method and kit for preparation of specimens and biomolecules. The invention provides the methods and kits for preparation of specimens and biomolecules as follows: the methods and kits for preparation of specimens and biomolecules without involving phenol and chloroform; One solution that can integratively protect, isolate and alter the specimens and biomolecules and subsequently isolate biomolecules directly from the specimens in the protection agents for specimens and biomolecules; One method and kit can versatilely isolate biomolecules from a variety of specimens including solid specimens, liquid specimens, chemical or enzymatic reaction specimens, gel slice specimens containing biomolecules, and contaminated or over-diluted specimens by itself; One method and kit can systematically isolate biomolecules including DNA/ccfDNA, Large RNA/mRNA/ccfRNA, Small RNA/miRNA/ccfmiRNA, protein, lipid, carbohydrate, and metabolite simultaneously from the same specimen; One method and kit can serve as a core method and kit to cover most functions and applications in preparation of specimen and to extend the extra functions and applications to many other particular specimens and biomolecules including isolation of biomolecules from formalin fixed and paraffin embedded (FFPE) tissue sections, isolation of mitochondria DNA and nucleic DNA from mitochondria and nuclei, isolation of plasmid DNA from bacteria, elimination of DNA from RNA, conversion of DNA for methylation analysis, preparation of DNA fragments, DNA labeling and RNA labeling.

This invention relates the methods and kits for Integrated Versatile and Systems Preparation of specimens comprise core module and plug-in modules for integrated versatile and systems protection, isolation and alteration of specimens and biomolecules (DNA/ccfDNA, Large RNA/mRNA/ccfRNA, Small RNA/miRNA/ccfmiRNA, protein, lipid, carbohydrate, and metabolite). The core module and plug-in modules are derived from open module technology. The core module protects the histological structures and micromorphology of specimens and protects intactness of biomolecules in specimens or in the lysate of specimens; the core module subsequently isolates the systems biomolecules versatilely from a vast variety of specimens without or with addition of Plug-in modules; and the core module also alters the characteristics of biomolecules without or with addition of Plug-in modules. There are two solutions in the core module, 2×PLIS solution (Protection-Lysis-Inhibition-Separation) and 1.5×DAP solution (Decontamination, Alteration, Protection and Purification). Furthermore, the core module can accept and adopts emerging or custom Plug-in modules for expanding the functions, applications and varieties of systems specimens' preparation through the open module technology.

One embodiment of this invention is that the systems preparation isolates biomolecules (DNA/ccfDNA, Large RNA/mRNA/ccfRNA, Small RNA/miRNA/ccfmiRNA, protein, lipid, carbohydrate, and metabolite) simultaneously from the same or difference piece of specimens for the applications with systems approach. These biomolecules are conventionally isolated individually, irrespectively, irrelevantly, randomly, or asynchronously, and applied in different biological and medical systems in unrelated and irrespective means. The Integrated Versatile and Systems Preparation integrates the preparation methods such as protection, isolation and alteration for specimens and biomolecules into one kit with one set of comprehensive protocols using the kit. The kit consists of core module and plug-in modules.

The further embodiment is that the core module and plug-in modules are derived from open module technology. The core module consists of solutions. The plug-in modules consist of a great variety of substances, materials, chemicals, reagents, solution, columns, instruments, equipment, objects, and etc. The examples of plug-in modules are materials for solid phase binding of biomolecules, the equipment or instrument for automated processing specimens and biomolecules, the solutions for special treatments of certain particular specimens, and the solutions for alteration of biomolecules. The core module plays the leading role and has major functions or applications of the Integrated Versatile and Systems Preparation of specimens. The plug-in modules extend and broaden the functions or applications of core module. The plug-in modules are designed and act as plug-and-play modules for the core module. The open module technology created the current core module and plug-in modules for the Integrated Versatile and Systems Preparation of specimens. The open module technology identifies, selects and optimizes the substances, materials, chemicals, reagents, solution, columns, instruments, equipment, objects and others for core module or plug-in modules according to their functions, safety, cost, effectiveness, efficiency, compatibilities and openness to each other. The open module technology will create new or emerging plug-in modules continuously and the open module technology accept and adopt custom plug-in modules to expand the functions or applications of the core module and, thus, the Integrated Versatile and Systems Preparation of specimens.

Another embodiment of this invention is that the solutions of the core module and plug-in modules are composed by chemicals that protect, isolate and alter specimens and biomolecules. The chemicals include, but not limited to, Sodium lauroyl sarcosinate (Sarkosyl), Sodium dodecyl sulfate (SDS), Tween-20, Triton X-100, Tris(hydroxymethyl)aminomethane (Tris), Tris(2-carboxyethyl)phosphine hydrochloride (TCEP), cesium chloride (CsCl), Guanidine thiocynate, Guanidine hydrochloride, urea, sodium chloride (NaCl), lithium chloride (LiCl), Sodium Citrate, alcohol, sodium iodide, Ammonium acetate, Sodium acetate, Ethylenediaminetetraacetic acid disodium salt dihydrate (EDTA), Trimethylene bromochloride, Concanavalin A (Con-A) column, methyl-α-D-glucopyranoside, Dnase, Fragmentase (NEB), Sodium Bisulfite, Hydroquinone, sucrose, Hexadecyltrimethylammonium bromide (CTAB), Polyvinylpyrrolidone at average mol wt 40,000 (PVP40), lysozyme, lyticase, Zymolyase, Sodium hydroxide (NaOH), potassium acetate, DNA polymerase, reverse transcriptase, RNA polymerase, affinity column containing glass fiber, magnetic beads, Proteinase, Rnase, Magnesium chloride (MgCl2), Calcium chloride (CaCl2), and Manganese chloride (MnCl2). The equipment or instrument for automated processing specimens and biomolecules include tissue homogenizer, liquid handler, magnetic separator, vacuum, and centrifuge.

The chemicals in the solutions are at different concentrations. The Sarkosyl is at 0.1-20%, SDS is at 0.1-20%, Tween-20 is at 0.1-30%, Triton X-100 is at 0.1-30%, Tris is at 10-900 mM, TCEP is at 10-100 mM, Cesium chloride (CsCl) is at 0.5-9 M, Guanidine thiocynate is at 1-5.5 M, Guanidine hydrochloride is at 1-8 M, urea is at 2-6 M, sodium chloride (NaCl) is at 0.1-5 M, lithium chloride (LiCl) is at 0.3-18 M, Sodium Citrate is at 20-100 mM, alcohol is at 0-95%, sodium iodide is at 1-5 M, Ammonium acetate at 1-10 M, Sodium acetate is at 0.1-5 M, EDTA is at 0.1-50 mM, Trimethylene bromochloride at 100%, Concanavalin A (Con-A) column use as instructed from manufacture, methyl-α-D-glucopyranoside is at 0.1-2 M, Dnase is at 200-2000 u/ml, Fragmentase (NEB) as manufacture instruction, Sodium Bisulfite is at 30-50%, Hydroquinone is at 0.5-2%, sucrose is at 200-400 mM, CTAB is at 0.2-8%, PVP40 is at 0.2-8%, lysozyme is at 0.2-2 mg/ml, lyticase or Zymolyase as manufacture instruction, NaOH is at 0.1-5N, potassium acetate is at 0.2-5 M, DNA polymerase is at 4-400 u/ml, Reverse transcriptase is at 20-20000 u/ml, and RNA polymerase is at 100-10000 u/ml, Affinity column containing glass fiber and magnetic beads amount is depended on the amount of biomolecules to be isolated. Proteinase is at 0.5-3 mg/ml, Rnase is at 20-200 mg/ml. MgCl2 is at 10-400 mM, CaCl2 is at 20-100 mM, and MnCl2 is at 1-50 mM. One Affinity column or Concanavalin A (Con A) Sepharose™ 4B beads is for each isolation, magnetic beads amount is depended on the amount of biomolecules to be isolated.

One important embodiment of this invention is that the comprehensive protocols integrate three types of preparation of specimens (protection, isolation and alteration) and systems preparation of specimens (isolation of DNA/ccfDNA, Large RNA/mRNA/ccfRNA, Small RNA/miRNA/ccfmiRNA, Protein, Lipid, Carbohydrate, and metabolites simultaneously) into one Kit. The core module without or with Plug-in modules as one kit can protect specimen and biomolecules; isolate systems biomolecules simultaneously; and alter the biomolecules. The protocols for Integrated Versatile and Systems Preparation of Specimens can be used selectively or individually for a particular preparation of specimen. The core module without or with Plug-in modules as one kit can prepare systems biomolecules (DNA/ccfDNA, Large RNA/mRNA/ccfRNA, Small RNA/miRNA/ccfmiRNA, Protein, Lipid, Carbohydrate, and metabolites) versatilely from all different specimens including, but not limited to, solid specimens (tissue, cultured cell, plant, microorganism, and etc.) and liquid specimens (serum/plasma, blood, biofluid, and etc.). The core module without or with Plug-in modules as one kit can accept and adopt the new and custom Plug-in modules for expanding the multiple functions and applications in preparation of specimens through open module technology. The core module without or with Plug-in modules as one kit with one set of standardized protocols is compatible to different biomolecules prepared from different specimens, compatible to biomolecules in different status (in PCR reaction, in gel, contaminated samples, or diluted samples), compatible to biomolecules altered by different method (labeling, modification, conversion, fragmentation), and compatible to the means of preparation (manual or automation). Users can use one set of standardized and connected kits with one set of standardized and connected protocols to meet all needs in preparation of specimen and biomolecules, which are the ultimate goal of the Integrated Versatile and Systems Preparation of specimens from this invention.

The further embodiment is that the protocols for one Kit with the core module can carry out varieties or multiple functions and applications in isolations which include, but not limited to, 1) Isolation of DNA/ccfDNA, Large RNA/mRNA/ccfRNA, Small RNA/miRNA/ccfmiRNA, and Protein simultaneously (from tissue, cultured cell, plant, bacteria, serum/plasma, blood, and biofluid); 2) Isolation of Large RNA/mRNA/ccfRNA (from cell lysate, serum/plasma and other liquid specimens); 3) Isolation of Large RNA/mRNA/ccfRNA (from tissue, cultured cell, plant, bacteria or plasma/serum with DNA contamination or with problem of RNA degradation); 4) Isolation of DNA/ccfDNA (from tissue, cultured cell, plant, bacteria, or serum/plasma); 5) Isolation of Small RNA/miRNA/ccfmiRNA (from tissue, cultured cell, plant, bacteria, or serum/plasma); 6) Isolation of Protein (from tissue, cultured cell, plant, bacteria, or serum/plasma); 7) Isolation of ccfDNA/ccfRNA/ccfmiRNA mixture (from serum/plasma and other biofluid); 8) Isolation of ccfDNA/ccfmiRNA mixture with removal of PCR inhibitors (from serum/plasma and other biofluid); 9) Isolation of ccfmiRNA with removal of PCR inhibitors (from serum/plasma and other biofluid) individually; 10) Clean up and concentrating of DNA/ccfDNA, Large RNA/mRNA/ccfRNA or Small RNA/miRNA/ccfmiRNA (from PCR or other reactions, or diluted samples).

An additional embodiment is that the protocols for one Kit with the core module, with addition of Plug-in modules, can carry out extra functions and applications in isolations and alterations of biomolecules on top of multiple functions and applications carried out by the core module only. The extra functions and applications include, but not limited to, 1) Isolation of DNA/ccfDNA, Large RNA/mRNA/ccfRNA, Small RNA/miRNA/ccfmiRNA, Protein, Lipid, Carbohydrate, and metabolites simultaneously (from tissue, cultured cell, plant, bacteria, serum/plasma, blood, and biofluid); 2) Automation in Isolation of DNA/ccfDNA, Large RNA/mRNA/ccfRNA, Small RNA/miRNA/ccfmiRNA, and Protein with magnetic beads and automated instrument (from tissue, cultured cell, plant, bacteria, serum/plasma, blood, and biofluid); 3) Isolation of lipids (from tissue, cultured cell, plant, bacteria, whole blood, serum/plasma and other biofluid); 4) Isolation of Carbohydrate (from tissue, cultured cell, plant, bacteria, whole blood, serum/plasma and other biofluid); 5) Recovery of DNA/ccfDNA, Large RNA/mRNA/ccfRNA, and Small RNA/miRNA/ccfmiRNA (from Agarose gel slices); 6) Isolation of DNA, Large RNA/mRNA, Small RNA/miRNA, and Protein from FFPE Tissue Sections; 7) Isolation of DNA, Large RNA/mRNA, Small RNA/miRNA, Protein, Lipid, Carbohydrate, and Metabolite Simultaneously from Plant tissue rich in polysaccharide and polyphenols; 8) Isolation of DNA, Large RNA/mRNA, Small RNA/miRNA, Protein, Lipid, Carbohydrate, and Metabolite Simultaneously from Bacteria; 9) Isolation of Plasmid DNA from Bacteria; 10) Isolation of Mitochondria DNA and Nucleic DNA from Cells and Tissues; 11) Removal of DNA from RNA/miRNA; 12) DNA Fragmentation; 13) DNA Methylation Analysis; 14) DNA Labeling; 15) RNA Labeling, and etc.

One embodiment of this invention is the benefits of comprehensive functions and application of the core module. 1) It protects histological structures and micromorphology and intactness of biomolecules in the original specimens by store the original specimens in lysis solution at 4° C. and protects the intactness of biomolecules in the lysate of specimens at 4° C. 2) It lyses of tissue, cell, exosome, plant, other solid specimen or liquid specimens. 3) It inhibits Rnase, Dnase, proteinase and other enzymes that degrade the biomolecules. 4) It separates Large RNA/mRNA/ccfRNA from DNA/ccfDNA and Small RNA/miRNA/ccfmiRNA by differential centrifugation of the crude lysate of specimens without removing protein, without phenol/chloroform extraction, without binding Large RNA/mRNA/ccfRNA, DNA/ccfDNA or Small RNA/miRNA/ccfmiRNA on solid phase binding materials, or without other treatment to the lysate; It separates DNA/ccfDNA from Small RNA/miRNA/ccfmiRNA by differential precipitation of the crude lysate of specimens containing 25-35% alcohol but without removing protein, without binding Large RNA/mRNA/ccfRNA, DNA/ccfDNA or Small RNA/miRNA/ccfmiRNA on solid phase binding materials, or without other treatment to the lysate; 5) It decontaminates Large RNA/mRNA/ccfRNA from contaminants by decontamination in the 1×DAP Solution; It separates Large RNA/mRNA/ccfRNA from DNA/ccfDNA by differential precipitation of lysate of specimens in the 1×DAP Solution containing 25-35% alcohol with or without binding on solid phase binding materials. 6) It differentially precipitates Large RNA/mRNA/ccfRNA, DNA/ccfDNA, Small RNA/miRNA/ccfmiRNA and protein. PLIS solution differentially precipitates Large RNA/mRNA/ccfRNA with presentation of 0% alcohol, differentially precipitates DNA/ccfDNA with presentation of 32% alcohol, differentially precipitates Small RNA/miRNA/ccfmiRNA with presentation of 60% alcohol, and differentially precipitates protein with presentation of 90% alcohol. It differentially precipitates DNA/ccfDNA and isolate DNA/ccfDNA by centrifugation of the crude lysate of specimens containing 25-35% alcohol but without removing protein, without binding on solid phase binding materials, or without other treatment to the lysate; It differentially precipitates Large RNA/mRNA/ccfRNA and isolate Large RNA/mRNA/ccfRNA by centrifugation of the lysate of specimens in 1×DAP Solution containing 25-35% alcohol without binding on solid phase binding materials; It differentially precipitates Small RNA/miRNA/ccfmiRNA and isolate Small RNA/miRNA/ccfmiRNA by centrifugation of the crude lysate of specimens containing 50-70% alcohol but without removing protein, without binding on solid phase binding materials, or without other treatment to the lysate. 7) It isolates ccfDNA, ccfRNA, and ccfmiRNA from plasma, serum or other biofluid in 0.4× lysis solution containing 60% ethanol without precipitation of protein from plasma, serum or biofluid, or without phenol extraction of protein from plasma, serum or biofluid. 8) It prevents protein from precipitation in plasma or serum for effective isolation of ccfDNA, ccfRNA and ccfmiRNA without co-precipitation of protein when high concentration of ethanol is applied during isolation; 9) it removes inhibitors in plasma or serum from isolated ccfDNA, ccfRNA and ccfmiRNA by differential centrifugation; 10) It differentially binds DNA/ccfDNA, large RNA/mRNA/ccfRNA and Small RNA/miRNA/ccfmiRNA and Carbohydrate on solid phase binding materials including, but not limited to, Affinity column, magnetic beads, or Con-A column by differential solid phase binding, and therefore isolate DNA/ccfDNA, large RNA/mRNA/ccfRNA, Small RNA/miRNA/ccfmiRNA and Carbohydrate from specimens on automated equipment or instruments in an automated means with minimum manual involvement. 11) It purifys DNA/ccfDNA, Large RNA/mRNA/ccfRNA, and Small RNA/miRNA/ccfmiRNA by dissociation protein and other contaminant from DNA/ccfDNA, Large RNA/mRNA/ccfRNA, and Small RNA/miRNA/ccfmiRNA; 12) It alters the DNA/ccfDNA for DNA/ccfDNA methylation assay by dissociation protein and other contaminant from DNA during DNA conversion and by converting and modifying DNA/ccfDNA in 0.06×DAP Solution containing Sodium Bisulfite and Hydroquinone; it alters the DNA for Nextgen DNA sequencing by fragmentation of DNA; and it alters the DNA or RNA for hybridization by labeling DNA or RNA; 13) It enables isolation of DNA/ccfDNA, Large RNA/mRNA/ccfRNA, and Small RNA/miRNA/ccfmiRNA by means of automation on equipments or instruments.

One important embodiment of this invention is that the invention benefits users on aspects of quality results, working efficiency, safety, economic and environment, which include but not limited to: 1) obtaining prepared biomolecules with superior quality and ultra purity, e.g. RNA will not degrade even electrophoresis in non-denaturing DNA gel; 2) working at room temperature, easy to use protocols, and fast turn-around time due to intrinsic inhibition activity in the core module, elimination of phenol/chloroform extraction and other unnecessary steps; 3) One Kit for all: One Stop shopping because of multiple functions or application of preparation by the core module with Plug-in modules; 4) One Set of standardized protocols for different functions or application of all preparations; 5) compatible to different biomolecules (nucleic acid, protein, carbohydrate, lipid and metabolites) prepared from different specimens (solid and liquid specimens), compatible to biomolecules in different status (in PCR reaction, in gel, contaminated samples, or diluted samples), compatible to biomolecules altered by different method (labeling, modification, conversion, fragmentation), and compatible to the means of preparation (manual or automation); 6) expanding the functions and applications of the core module in protection, isolation and alteration from covering most specimens and biomolecules to covering almost all specimens and biomolecules with addition of Plug-in modules; enabling one set of standardized kit and protocols to meet all needs in preparation of specimen and biomolecules in the biomedical fields, which demands many different kits and different protocols from different vendors; 7) sharing the core module with other Plug-in modules due to the compatibility among the core module and Plug-in modules held by different users or produced in manufacturers, which provides convenience to use and increase the efficiency for manufactures; 8) reducing cost to users due to sharing modules and avoiding purchase many different whole kits for different applications from different vendors; and obtaining standardized, cost-effective and high efficient products with consistent quality; 9) reducing cost to manufactures due to sharing modules and avoiding manufacture many different whole kits for different applications; providing standardized, cost-effective and high efficient products with consistent quality; 10) reduce contamination to environment due to eliminating phenol and chloroform, sharing modules for avoiding manufacture many different whole kits, and optional eliminating solid phase binding materials for binding of DNA/ccfDNA, Large RNA/mRNA/ccfRNA, and Small RNA/miRNA/ccfmiRNA; 11) safe and no toxic to users, manufacture and environment due to elimination of phenol, chloroform and other toxic organic reagents conventionally used in isolation of DNA/ccfDNA, Large RNA/mRNA/ccfRNA, and Small RNA/miRNA/ccfmiRNA; 12) Leading to a low-carbon and Green economy in preparation of DNA/ccfDNA, Large RNA/mRNA/ccfRNA, Small RNA/miRNA/ccfmiRNA, protein, lipid, carbohydrate and metabolite from specimens due to the advantages of high efficiency, high effectiveness and low demanding on natural or man-made resources possessed by the method and Kit derived from this invention for Integrated Versatile and Systems Preparation of samples; and 13) providing the product or kit that prepares specimens and biomolecules with the features and benefits of high quality, easy to use, fast, no toxic materials, safe to user and environment, low demanding on the materials and labors, cost-effective, reducing waste, saving nature resources and environment, and leads to a low-carbon and Green economy in preparation of specimens.

BRIEF DESCRIPTION OF DRAWINGS AND FIGURES

FIG. 1. Overview of Integrated Versatile and Systems Preparation of Specimens.

FIG. 2. Key Features and Benefits of Integrated Versatile and Systems Preparation of Specimens.

FIG. 3. Protection of Histological Structure and micromorphology of Specimens by the PLIS solutions from the core module Panel A: Frozen Liver Tissue Section with HE Staining after store in PLIS solution at 4° C. for 10 days; Panel B: Frozen Liver Tissue Section with HE Staining after store in −80° C. freezer for 10 days without PLIS solution; Panel C: FFPE Human Lung cancer small cell Carcinoma Tissue Section with HE Staining after store in PLIS solution at 4° C. for 10 days; and Panel D: FFPE Human Lung cancer small cell Carcinoma Tissue Section with HE Staining after store in −80° C. freezer for 10 days without PLIS solution. PLIS solution from the core module protects the histological structure and micromorphology of specimens when specimens were stored in PLIS solution at 4° C. for 10 days. Stored specimens can be used for frozen or FFPE section.

FIG. 4. Protection of Biomolecules in specimens by the PLIS solution from the core module Comparison of biomolecules stability from tissue stored in the PLIS solution to tissue stored in PBS at 4° C. for 10 days. Biomolecules were isolated by Allzol Kit without affinity columns. Lane 1, 3, 5, and 7 are degraded DNA, Large RNA/mRNA, Small RNA/miRNA and protein isolated from liver tissues stored in PBS at 4° C. for 10 days. Lane 2, 4, 6, and 8 are intact DNA, Large RNA/mRNA, Small RNA/miRNA and protein isolated from liver tissues stored in the PLIS solution from the core module at 4° C. for 10 days. PLIS solution protects biomolecules in specimens from degradation when Specimens were stored in PLIS solution at 4° C. for 10 days.

FIG. 5. Protection of Biomolecules in lysate of specimens lysed by the PLIS solution from the core module. Panel A: DNA; Panel B: Large RNA/mRNA; Panel C: Small RNA/miRNA; Panel D: protein. Hela cell was lysed by the PLIS solution from the core module and Hela cell lysate was store at 4° C. for 20 days. Biomolecules were isolated by Alliso Kit with affinity columns. The DNA, Large RNA/mRNA, Small RNA/miRNA and protein were isolated at storage for 0 day, 10 days and 20 days. DNA, Large RNA/mRNA, Small RNA and protein are not degraded up to 10 and 20 days when stored in PLIS solution at 4° C.

FIG. 6. Integrated Versatile and Systems Preparation of Specimens: Overview of the core module with differential precipitation methods FIG. 7. Integrated Versatile and Systems Preparation of Specimens: Overview of the core module plus differential solid phase binding method FIG. 8. Separation of Large RNA/mRNA from DNA with differential centrifugation and isolation of Large RNA/mRNA and DNA by differential precipitation methods (Panel A) or by differential solid phase binding methods (Panel B) The Large RNA/mRNA and DNA are isolated by differential precipitation method (Panel A) or differential solid phase binding method (Panel B) after separation from each other by differential centrifugation. Lane 1, 2, 3, and 4 are DNA. Lane 5, 6, 7, and 8 are Large RNA/mRNA. The differential centrifugation method can separate Large RNA/mRNA from DNA effectively. The differential precipitation method (Panel A) has consistent and similar results as differential solid phase binding method (Panel B) in separation and isolation of DNA and Large RNA/mRNA.

FIG. 9. Protocols for separation of DNA/ccfDNA, Large RNA/mRNA/ccfRNA, Small RNA/miRNA/ccfmiRNA, protein Lipid, carbohydrate, and metabolite from each other in different degrees by differential precipitation method.

FIG. 10. Protocols for separation of DNA/ccfDNA, Large RNA/mRNA/ccfRNA, Small RNA/miRNA/ccfmiRNA, protein Lipid, carbohydrate, and metabolite from each other in different degrees by differential solid phase binding method.

FIG. 11. Isolation of DNA, Large RNA/mRNA, Small RNA/miRNA and Protein from bacteria, plant and animal tissue by Allzol Kit or by Alliso Kit. Isolation of DNA, Large RNA/mRNA, Small RNA/miRNA and Protein from bacteria, plant and animal tissue by Allzol Kit (Panel A of FIG. 11) or Alliso Kit (Panel B of FIG. 11). 1% Agarose gel electrophoresis of DNA, Large RNA/mRNA and Small RNA/miRNA. DL: DNA ladder Lambda Hind III; DB: DNA from bacteria; RB: RNA from bacteria; miB: miRNA from bacteria; DP: DNA from plant leaf; RP: RNA from plant leaf; miP: miRNA from plant leaf; DA: DNA from animal tissue; RA: RNA from animal tissue; miA: miRNA from animal tissue. Large RNA/mRNA from animal tissue, plant leaf and bacteria was not degraded even electrophoresis in DNA gels as compared with Large RNA/mRNA in RNA gel (Panel C). Panel C of FIG. 11: Large RNA/mRNA from animal (RA), plant (RP) and bacteria (RB) is not degraded as confirmed in RNA gel. Panel D of FIG. 11: PAGE analysis of protein isolated from bacteria, plant and animal tissue. The protein was isolated with Allzol or Alliso Kit. Bz: bacterial protein isolated with Allzol Kit; Pz: plant protein isolated with Allzol Kit; Az: animal protein isolated with Allzol Kit; Pi: plant protein isolated with Alliso Kit; Ai: animal protein isolated with Alliso Kit; PL: protein ladder. The proteins isolated by Allzol and Alliso kit are similar to each other.

FIG. 12. QPCR of ccfDNA isolated from human serum with Actin Primer/Probe. The ccfDNA was isolated with Allzol Kit or Alliso Kit. Both Kits show the similar result.

FIG. 13. QRT-PCR of ccfRNA isolated from serum with Beta Globin or Actin primer/probe. The ccfRNA was isolated with Allzol Kit. Beta Globin is a better internal control.

FIG. 14. Agarose gel electrophoresis of QRT-PCR product of ccfmiRNA with mir24 primer/probe. The ccfmiRNA was isolated from serum with Allzol Kit. DL: DNA 100 bp ladder; R: ccfRNA fraction; D: ccfDNA fraction; miR: ccfmiRNA fraction; DRmiR: Total ccfNA (ccfDNA/ccfRNA/ccfmiRNA); C: tissue miRNA control; NTC: None template control. Allzol Kit can isolate ccfmiRNA well and ccfmiRNA fraction has similar amount of mir24 as Total ccfNA.

FIG. 15. Agarose gel electrophoresis of recovered DNA from Agarose gel and DNA before recovery. DNA/R: recovered genomic DNA from gel slice; DNA/S: genomic DNA before recovery in agarose gel; L/R: DNA Ladder recovered from gel slice; L/S: DNA ladder before recovery in agarose gel.

FIG. 16. Agarose gel Electrophoresis analysis of DNA/RNA and RNA/miRNA isolated from FFPE tissue sections. DNA/RNA: DNA and RNA/miRNA mixture isolated from FFPE tissue section; RNAz: RNA and miRNA mixture isolated from FFPE tissue section by Allzol Kit; RNAi: RNA and miRNA mixture isolated from FFPE tissue section by Alliso Kit; DL: DNA 100 bp ladder.

FIG. 17. Quantitative PCR (QPCR) for FFPE DNA. Comparison of FFPE DNA isolated by Allzol Kit, Alliso Kit and Kit from market leader Q by QPCR with Actin primer and probe FFPE DNA (Allzol DNA FFPE) isolated by Allzol Kit is similar to the FFPE DNA (Allsio DNA FFPE) isolated by Alliso Kit. The FFPE DNA isolated by Allzol and Alliso Kit is slightly better than the FFPE DNA (Q DNA FFPE) isolated by Kit from market leader Q.

FIG. 18. Quantitative Real Time PCR (QRT-PCR) for FFPE RNA/miRNA. Comparison of FFPE RNA isolated by Allzol Kit and Alliso kit by QRT-PCR with Actin primer and probe. FFPE RNA (Allzol RNA) isolated by Allzol Kit is similar to the FFPE RNA (Alliso RNA) isolated by Alliso Kit. NTC: none template control.

FIG. 19. Quantitative Real Time PCR (QRT-PCR) for FFPE miRNA. Comparison of FFPE RNA/miRNA isolated by Allzol Kit, Alliso Kit and kit from market leader Q by QRT-PCR with mir24 primer and probe. FFPE RNA/miRNA (Allsol FFPE RNA/miRNA) isolated by Allzol Kit is similar to the FFPE RNA/miRNA (Alliso FFPE RNA/miRNA) isolated by Alliso Kit. The FFPE RNA/miRNA isolated by Allzol and Alliso Kit is three Ct better than the FFPE miRNA (Q FFPE miRNA) isolated by Kit from market leader Q.

FIG. 20. Agarose gel electrophoresis of plasmid DNA isolated from bacteria by Allzol Kit or Alliso Kit. Lane 1, 2, and 3: plasmid DNA isolated by Allzol Kit. The size of Plasmid DNA are 3.9, 6.2 and 42 kb without digestion of restriction enzyme; Lane 4: genomic DNA; Lane 5, 6, and 7: plasmid DNA isolated by Alliso Kit. The size of Plasmid DNA are 3.9, 6.2 and 42 kb without digestion of restriction enzyme; Lane 8: DNA ladder, Lambda Hind III. The plasmid DNA isolated by Allzol Kit is similar to the plasmid DNA isolated by Alliso Kit.

FIG. 21. Agarose gel electrophoresis of Mitochondria DNA and Nucleic DNA isolated by Allzol Kit. Lane 1: DNA ladder, Lambda Hind III; Lane 2: mitochondria DNA; Lane 3: Nucleic DNA; Lane 4: DNA and RNA in supernatant.

FIG. 22. QPCR of Mitochondria DNA and Nucleic DNA with Cyto B primer The Cyto B in Mitochondria DNA (Mt DNA) is about 250 times more enriched than the Nucleic DNA. From Left to Right: 1. Mitochondria DNA; 2. Total DNA; 3. Supernatant DNA; 4. Nucleic DNA.

FIG. 23. Agarose gel electrophoresis of RNA and miRNA with removal of DNA by Allzol or Alliso Kit. Lane 1: RNA contaminated with DNA; Lane 2: RNA with removal of DNA by Allzol Kit; Lane 3: RNA with removal of DNA by Alliso Kit; Lane 4: genomic DNA; Lane 5: miRNA contaminated with DNA; Lane 6: miRNA with removal of DNA by Allzol Kit; Lane 7: miRNA with removal of DNA by Alliso Kit; Lane 8: 100 bp DNA ladder. Lane 1, 2, 3, and 4 are in 1% agarose gel and Lane 5, 6, 7, and 8 are in 3% agarose gel.

FIG. 24. QPCR and QRT-PCR of FFPE DNA or FFPE RNA/miRNA with removal of DNA by Allzol or Alliso Kit. FFPE RNA/miRNA containing DNA contamination QPCR (RO) without DNA remove. After DNA remove with Alliso or Allzol method, QPCR (Alliso, Allzol) did not detect DNA. FFPE RNA/miRNA was not affected by DNA removal, QRT-PCR (Alliso, Allzo) still have the same amount of RNA as without DNA removal QRT-PCR (RO).

FIG. 25. DNA fragmentation by DNA Mincer. DMz: minced DNA isolated by Allzol Kit; DMi: minced DNA isolated by Alliso Kit; D: genomic DNA before mince; DL: DNA ladder.

FIG. 26. Agarose gel electrophoresis of PCR product from converted DNA and wild type (unconverted) DNA with Methylation primer, Unmethylation primer or wild type primer DNA can be converted and amplified by Met primer for converted DNA with methylation (lane 3); Converted DNA cannot be amplified by unmethylation primer for converted DNA without methylation (lane 7); Converted DNA cannot be amplified by wild type primer for wild type DNA (lane 5); Wild type DNA can only be amplified by wild type primer (lane 4), but cannot be amplified by Methylation primer (lane 2) or Unmethylation primer (lane 6).

FIG. 27. QPCR of Converted and wild type (unconverted) DNA with Methylation primer, Unmethylation primer or wild type primer. DNA can be converted and amplified by Met primer for converted DNA with methylation (Peak of Converted DNA/Met-Primer); Wild type DNA can only be amplified by wild type primer (Wt-DNA/Wt-Primer); Converted DNA cannot be amplified by wild type primer for wild type DNA (Conv-DNA/Wt-Primer); Converted DNA cannot be amplified by unmethylation primer for converted DNA without methylation (Conv-DNA/Um-Primer); wild type DNA cannot be amplified by Methylation primer (Wt-DNA/Met-Primer) or Unmethylation primer (Wt-DNA/Um-Primer).

FIG. 28. High yield and quality of DNA and RNA isolated by Allzol Kit and Alliso Kit compared with the market leaders Q and I. Q: Market leader Q; I: Market leader I; Az: Allzol Kit; and Ai: Alliso Kit. Allzol Kit (differential precipitation method) and Alliso Kit (differential solid phase binding method) shown higher yield of DNA (Panel A) and better quality of RNA than market leaders Q and I.

FIG. 29. Better stability and quality of the RNA isolated by Allzol Kit and Alliso Kit compared with market leaders Q and I. Panel A: RNA (from I and Q Kit) in DNA gel, RNA degradation; Panel B: RNA (from Allzol/Alliso Kit) in DNA gel, No RNA degradation; Panel C: RNA (from I and Q Kit) in RNA gel, No RNA degradation; and Panel D: RNA (from Allzol/Alliso Kit) in RNA gel, No RNA degradation. I: Market leader I; Q: Market leader Q; Az: Allzol Kit; and Ai: Alliso Kit. Allzol Kit (differential precipitation method) and Alliso Kit (differential solid phase binding method) shown better stability and quality of isolated RNA than market leaders Q and I due to functions of inhibition and decontamination of Rnase by Allzol and Alliso Kits.

DETAILED DESCRIPTION OF THE INVENTION

This invention relates to integration of three major methods that are widely used for preparation of specimens and biomolecules in bioscience, i.e. Protection of specimens and biomolecules in specimens, isolation of biomolecules including DNA/ccfDNA, Large RNA/mRNA/ccfRNA, Small RNA/miRNA/ccfmiRNA, Protein, Lipid, Carbohydrates, and Metabolite from specimens, and alteration of biomolecules. Conventionally these preparation methods are conducted separately and irrelevantly in different product, kit, reagents or solutions because they are achieved by different kinds of chemicals, and sometimes contradicted or conflicted chemicals or reagents. From process point of view in the preparation of biomolecules, although they are very closed related sequentially, Isolation of biomolecules from specimen follows the protection of specimens, while biomolecules are altered after isolation from specimens, the three preparation methods were always performed separately with clear boundary in prior arts. Conventionally, the specimens were protected in one product or kit whereas biomolecules were isolated from the protected specimens with other product or kit. Finally, the isolated biomolecules are altered with totally different products or kits. This invention integrated three different kinds of products or kits into one product or kit to perform the protection, isolation and alteration of specimens and biomolecules synchronously.

A variety of products or kits are conventionally used to isolate many different kinds of biomolecules including DNA/ccfDNA, Large RNA/mRNA/ccfRNA, Small RNA/miRNA/ccfmiRNA, Protein, Lipid, Carbohydrates, and Metabolite separately, individually, irrelevantly, irrespectively or asynchronously from different kinds of specimens. For systems approach the different biomolecules should be isolated from different pieces of same kind of tissue if relative relationship of different biomolecules is researched. This requires large amount and many pieces of same specimen, which is impossible in most specimens. This invention uses one product or kit to isolate different kinds of biomolecules from the same piece of specimens simultaneously or synchronously, which suits for the systems approach in research or diagnostic, such as systems biology, systems pathology, systems diagnostics, or systems medicine. The systems isolation in this invention was integrated as a part of three major methods for preparation of specimens, which forms the Integrated Versatile and Systems Preparation of Specimens.

To achieve the goal of Integrated Versatile and Systems Preparation of Specimens, open module technology was invented to address the incompatible issues of contradicted or conflicted chemicals or reagents used for these complicated preparation methods. The core module addresses the major issues in preparation of specimens, protection and isolation. The plug-in modules address a variety of alteration issues. The core module was designed to accept and adopt emerging or custom plug-in modules for expending the functions of the Integrated Versatile and Systems Preparation of Specimens. As shown in FIG. 1, this invention forms a complete system for preparation of most specimens and biomolecules with options for accepting and adopting emerging or custom specimens or biomolecules. The key feature, benefits and supporting technologies are illustrated in FIG. 2.

Three key technologies support the Integrated Versatile and Systems Preparation of Specimens are summarized in Table 1. They are integrated preparation, versatile and systems preparation and open module technologies. The functions of integrated preparation including protection, isolation, and alteration are summarized in Table 2. A single core module kit can protect specimens and biomolecules, isolate biomolecules from protected specimens, and alter the isolated biomolecules. The systems biomolecules isolated by systems isolation from solid and liquid specimens are summarized in Table 3. The systems biomolecules include DNA, Large RNA/mRNA, Small RNA/miRNA, Protein, Lipid, Carbohydrates, and Metabolite from solid specimens and include ccfDNA, ccfRNA, ccfmiRNA, Protein, Lipid, Carbohydrates, and Metabolite from liquid specimens. The open module technologies that create the vast varieties of functions performed by combinations of the core module and Plug-in modules are summarized in Table 4. A great variety of biomolecules can be isolated from most specimens and altered with different combinations of the core module and Plug-in modules. The table can be expanded with more emerging or custom Plug-in modules.

In summary, Integrated Versatile and Systems Preparation of Specimens comprises core module and plug-in modules, derived from open module technology, for integrated systems protection, isolation and alteration of specimens and biomolecules including DNA/ccfDNA, Large RNA/mRNA/ccfRNA, Small RNA/miRNA/ccfmiRNA, protein, lipid, carbohydrate, and metabolite.

TABLE 1

Key Technologies and Output in Integrated Versatile and Systems Preparation of Specimens Integrated Preparation Integrate three preparation methods including protection, isolation and alteration of specimen and biomolecules as shown in Table 2 in core module kit and extended by plug-in module kits derived from the open module technology.
Versatile and Systems Preparation Prepare DNA/ccfDNA, Large RNA/mRNA/ccfRNA, Small RNA/miRNA/ccfmiRNA, Protein, Lipid, Carbohydrates, and Metabolite simultaneously or individually from a vast variety of specimens by core module/plug-in module kits for systems diagnostics, systems medicine and systems biology. The specimens and systems biomolecules are included in Table 3.
Open Module Technology Open Module Technology is the supporting technology for the Integrated Versatile and Systems Preparation of Specimens. Through extensive selection and optimization, Open Module Technology identified many compatible solutions and methods, which constitute the Core module and Plug-in modules. Core module integrates the preparation methods of protection, isolation and alteration of specimen for major functions and applications. Plug in modules extend the Core module to the broad and new functions and applications as shown in Table 4.
Output Preparation, including protection, isolation and alteration, of the specimens and Biomolecules including DNA/ccfDNA, Large RNA/mRNA/ccfRNA, Small RNA/miRNA/ccfmiRNA, Protein, Lipid, Carbohydrates, and Metabolite simultaneously or individually from a vast variety of specimens by modular kits derived from the invented open module technology. The isolated biomolecules are applicable for system diagnostics, system medicine, system biology, and associated disciplines; and for research and clinical applications. The methods and kits prepare specimens and biomolecules with high quality and with the features and benefits of easy to use, fast, no toxic materials, safe to user and environment, low demanding on the materials and labors, cost-effective, reducing waste, saving nature resources and environment, and leads to a low-carbon and Green economy in preparation of specimens.

TABLE 2

Integrated Versatile and Systems Preparation of Specimens - Integrated Preparation

| Specimens and Biomolecules | Protection | Isolation | Alteration |
| --- | --- | --- | --- |
| Tissue Morphology | • | | |
| DNA in tissue | • | • | |
| Large RNA/mRNA in tissue | • | • | |
| Small RNA/miRNA in tissue | • | • | |
| Protein in tissue | • | • | |
| Lipid in tissue | • | • | |
| Carbohydrates in tissue | • | • | |

TABLE 2-continued

Integrated Versatile and Systems Preparation of Specimens - Integrated Preparation

| Specimens and Biomolecules | Protection | Isolation | Alteration |
|---|---|---|---|
| Metabolite in tissue | • | • | |
| DNA/ccfDNA in lysate | • | • | |
| Large RNA/mRNA/ccfRNA in lysate | • | • | |
| Small RNA/miRNA/ccfmiRNA in lysate | • | • | |
| Protein in lysate | • | • | |
| Lipid in lysate | • | • | |
| Carbohydrates in lysate | • | • | |
| Metabolite in lysate | • | • | |
| Clean up DNA/RNA in reactions | | • | |
| Gel slice Extraction of DNA/RNA | | • | |
| Automation with Magnetic Beads | | • | |
| FFPE Tissue Section | | • | |
| Mitochondria DNA and Nucleic DNA | | • | |
| Plasmid DNA | | • | |
| DNA removal from RNA | | • | |
| DNA Fragmentation | | • | • |
| DNA Conversion/Methylation | | • | • |
| DNA labeling | | • | • |
| RNA Labeling | | • | • |

TABLE 3

Integrated Versatile and Systems Preparation of Specimens - Versatile and Systems Preparation

| Biomolecules To be isolated | Specimen (whole cell) Isolation from | Specimen (Cell free) Isolation from |
|---|---|---|
| DNA | Isolate biomolecules from Cell/Tissue/Plant/Bacteria/Whole Blood specimens simultaneously | |
| Large RNA/mRNA | | |
| Small RNA/miRNA | | |
| Protein | | Isolate biomolecules from Serum/Plasma/Biofluid specimens simultaneously |
| Lipid | | |
| Carbohydrates | | |
| Metabolite | | |
| ccfDNA | | |
| ccfRNA | | |
| ccfmiRNA | | |
| DNA/RNA/miRNA | FFPE Tissue Section | |
| Mitochondria DNA and Nucleic DNA | Cell/Tissue/Plant//Whole Blood | |
| Plasmid DNA | Bacteria | |
| DNA removal from | Cell/Tissue/Plant/Bacteria/Whole Blood | Serum/Plasma/Biofluid |
| DNA Fragmentation | Cell/Tissue/Plant/Bacteria/Whole Blood | |
| DNA Conversion/Methylation | Cell/Tissue/Plant/Bacteria/Whole Blood | Serum/Plasma/Biofluid |
| DNA labeling | Cell/Tissue/Plant/Bacteria/Whole Blood | Serum/Plasma/Biofluid |
| RNA Labeling | Cell/Tissue/Plant/Bacteria/Whole Blood | Serum/Plasma/Biofluid |
| DNA/RNA/miRNA Clean up Reaction | Cell/Tissue/Plant/Bacteria/Whole Blood | Serum/Plasma/Biofluid |
| DNA/RNA/miRNA Gel slice Extraction | Cell/Tissue/Plant/Bacteria/Whole Blood | Serum/Plasma/Biofluid |
| DNA/RNA/miRNA Automation Preparation | Cell/Tissue/Plant/Bacteria/Whole Blood | Serum/Plasma/Biofluid |

TABLE 4

Integrated Versatile and System Preparation of Specimens - Open Module Technology

| Biomolecules To be isolated | Specimen Isolate from | Methods Allzol CM/PMS/PMO | Core Module | Plug-in Module | Alliso/Allauto Method CM/PMS/PMO |
|---|---|---|---|---|---|
| DNA | CTPBW | CM | • | •+ | CM + PMS |
| Large RNA/mRNA | CTPBW | CM | • | •+ | CM + PMS |
| Small RNA/miRNA | CTPBW | CM | • | •+ | CM + PMS |
| ccfDNA | SPB | CM | • | •+ | CM + PMS |
| ccfRNA | SPB | CM | • | •+ | CM + PMS |
| ccfmiRNA | SPB | CM | • | •+ | CM + PMS |
| Protein | CTPBW/SPB | CM | • | •+ | CM + PMS |
| DNA/RNA/miRNA | Clean up from Reaction mix | CM | • | •+ | CM + PMS |
| DNA/RNA/miRNA | Extraction from Gel slice | CM + PMS | •+ | •+ | CM + PMS |
| DNA/RNA/miRNA | Automation for CTPBW/SPB | CM + PMS | •+ | •+ | CM + PMS |
| Lipid | CTPBW/SPB | CM + PM | •x | •x+ | CM + PMO + PM |
| Carbohydrates | CTPBW/SPB | CM + PM | •x | •x+ | CM + PMO + PM |

TABLE 4-continued

Integrated Versatile and System Preparation of Specimens - Open Module Technology

| | | Methods Allzol | | Alliso/Allauto Method | |
|---|---|---|---|---|---|
| Biomolecules To be isolated | Specimen Isolate from | CM/PMS/PMO | Core Module | Plug-in Module | CM/PMS/PMO |
| Metabolite | CTPBW/SPB | CM + PM | •x | •x+ | CM + PMO + PM |
| DNA/RNA/miRNA | FFPE Tissue Section | CM + PMO | •x | •x+ | CM + PMO + PMS |
| Mitochondria DNA and Nucleic DNA | CTP W | CM + PMO | •x | •x+ | CM + PMO + PMS |
| Plasmid DNA | B | CM + PM | •x | •x+ | CM + PMO + PM |
| DNA removal from RNA | CTPBW/SPB | CM + PM | •x | •x+ | CM + PMO + PM |
| DNA Fragmentation | CTPBW | CM + PM | •x | •x+ | CM + PMO + PM |
| DNA Conversion/Methylation | CTPBW/SPB | CM + PM | •x | •x+ | CM + PMO + PM |
| DNA labeling | CTPBW/SPB | CM + PM | •x | •x+ | CM + PMO + PM |
| RNA Labeling | CTPBW/SPB | CM + PM | •x | •x+ | CM + PMO + PM |

Note:
CTPBW: Cell/Tissue/Plant/Bacteria/Whole Blood; SPB: Serum/Plasma/Biofluid
• Core Module (CM)
+ Add Plug-in module: Solid phase binding material (PMS)
x Add Plug-in module: Other specialized solutions, reagents, or materials (PMO)

The core module protects the histological structures and micromorphology of specimens and intactness of biomolecules, and subsequently isolates the systems biomolecules without or with addition of plug-in modules; the core module also alters the characteristics of biomolecules without or with addition of plug-in modules. Furthermore, the core module can accept and adopts new or custom plug-in modules for expanding the categories and varieties of systems specimen preparation through open module technology. A great variety of biomolecules can be isolated from most specimens and altered with different combinations of the core module and plug-in modules.

Broad Coverage of Biomolecules in the Invention

This invention has the broad coverage of biomolecules to be isolated as shown in Table 5. DNA/ccfDNA, Large RNA/mRNA/ccfRNA, Small RNA/miRNA/ccfmiRNA, protein, Lipid, Carbohydrate, and Metabolite are general name representing the corresponding groups of biomolecules applied in this invention. Each group contains similar material but with different characteristics and origins. For examples, in DNA/ccfDNA group genomic DNA is the common name for genome DNA; Circulating cell free DNA (ccfDNA) refers to all DNA in plasma or serum but not isolated from blood cell; Circulating cell free genomic DNA (ccfgDNA) refers to genomic DNA in plasma or serum but not isolated from blood cell; Nucleic DNA (nDNA) refers to DNA from nuclei, which is the genome DNA; Mitochondria DNA (mitDNA) refers to DNA from mitochondria, which is different from Nucleic DNA; Chloroplast DNA (cpDNA) is the DNA from Chloroplast in plant tissue, which is equivalent to Mitochondria DNA (mitDNA) in animal tissue; Plasmid DNA (pDNA) is the DNA from bacteria, which is independent from bacterial genomic DNA; Virus DNA is the DNA from virus, which can present inside cells of tissue or present in plasma or serum like ccfDNA; complementary DNA is the DNA reverse transcribed from RNA; and converted DNA is chemical modified DNA for methylation analysis. The Large RNA/mRNA/ccfRNA, Small RNA/miRNA/ccfmiRNA, protein, Lipid, Carbohydrate, and Metabolite also have their corresponding subspecies too, which are not explained in detail herein.

The Table 5 lists the detail names for each group of biomolecules that this invention can prepare. The title for each group was determined according to the biomedical importance.

TABLE 5

| Biomolecules to be isolated | |
|---|---|
| DNA/ccfDNA | Large RNA/mRNA/ccfRNA |
| Genomic DNA (gDNA) | Messenger ribonucleic acid (mRNA) |
| Circulating cell free DNA (ccfDNA) | Circulating cell free RNA (ccfRNA) |
| Circulating cell free genomic DNA (ccfgDNA) | Circulating cell free mRNA (ccfmRNA) |
| Nucleic DNA (nDNA) | Heterogeneous nuclear RNA (hnRNA) |
| Mitochondria DNA (mitDNA) | Ribosomal ribonucleic acid (rRNA) |
| Chloroplast DNA (cpDNA) | Transfer-messenger RNA (abbreviated tmRNA) |
| Plasmid DNA (pDNA) | |
| Virus DNA (vDNA) | Antisense RNA (aRNA) |
| Complementary DNA (cDNA) | Virus RNA (vRNA) |
| Converted DNA (cvDNA) | |
| Small RNA/miRNA/ccfmiRNA (less than 100 bp) | Protein |
| MicroRNA (miRNA) | Total protein |
| Transfer RNA (tRNA) | Cytoplasmic protein |
| Circulating cell free small RNA (ccfsRNA) | Nucleic protein |
| Circulating cell free microRNA (ccfmiRNA) | Membrane protein |
| Small interfering RNA (siRNA) | Cytoskeleton protein |
| Piwi-interacting RNA (piRNA) | |

TABLE 5-continued

Biomolecules to be isolated

Small nuclear ribonucleic acid (snRNA)
Small nucleolar RNAs (snoRNAs)
Trans-acting siRNA (ta-siRNA or tasiRNA)
Guide RNAs (aka gRNA)
Small temporal RNA (abbreviated stRNA)
Small hairpin RNA or short hairpin RNA (shRNA)

| Lipid | Carbohydrate |
|---|---|

| Metabolite | Others |
|---|---|

DNA/ccfDNA represents DNA in solid specimens such as tissue, and circulating cell free DNA (ccfDNA) in plasma or serum. In Large RNA/mRNA/ccfRNA group, mRNA has the major biomedical relevance and presented in the fraction of Large RNA. ccfRNA is the RNA in plasma or serum and some of ccfRNA can be in high molecular weight due to the protection of exosome in the plasma or serum. Although miRNA only takes a small portion of Small RNA/miRNA/ccfmiRNA group, but major biomedical relevance of miRNA makes it stand out in the name of group. ccfmiRNA is the miRNA in plasma or serum. There is no prior art claimed that one product or kit can isolate biomolecules with such broad coverage individually or simultaneously.

Broad Coverage of Specimens in the Invention

There are two common terms to describe or definite a piece or a volume of object taken from an organism in biomedical field, the specimen or sample. Two terms are interchangeable in many places and the difference in their meanings is not clear cut. Although the term of the specimen is selected in the invention due to its precision and broadness to the object, the term of the sample is still applicable in the places where specimen is used in this invention. The specimen is a single entity representing an object studied per se. A sample is not only representing an object studied per se, it should also be statistically representative collection of elements of a population. The specimen has broad concept and include sample. A specimen may not be a sample with a statistic characteristic, while sample is a specimen that statistically represents collection of elements of a population. When a specimen represents an object studied per se only, it is a specimen. When a specimen represents an object studied per se as well as statistically represents collection of elements of a population, it is a sample. In biomedical field, specimen usually refers to a piece of tissue taken for analysis during e.g. biopsy, while sample usually refers to certain volume of blood, urine, and etc. collected for analysis.

This invention has the broad coverage of specimens this invention can prepare. The specimens from which Biomolecules to be isolated in this invention including solid specimens, liquid specimens and other specimens are listed in Table 6. The solid specimens includes, but not limited to, Tissues, Frozen tissue sections, FFPE tissue sections, Biopsy samples, Cell pellet, Attached cells, Buccal cells, Bacteria, Parasite, Stool, Soil, Transport media, Blood spots, Blood

TABLE 6

Specimens from which Biomolecules to be isolated

| Solid Specimens | Liquid Specimens | Other BioFluid |
|---|---|---|
| Tissues | Plasma | Cerebrospinal fluid |
| Frozen tissue | Serum | Gastric juice |

TABLE 6-continued

Specimens from which Biomolecules to be isolated

| Solid Specimens | Liquid Specimens | Other BioFluid |
|---|---|---|
| sections | Whole blood | Pleural effusion |
| FFPE tissue sections | Buffy coat | Ascite |
| Biopsy samples | Bone marrow | Synovial fluid |
| Cell pellet | Cell suspension | Tears |
| Attached cells | Saliva | Semen |
| Buccal cells | Urine | Sweat |
| Microorganisms | Biofluids | Sputum |
| Bacteria | Beverage | Cervical and vaginal |
| Yeast | Water | secretions |
| Virus | RNA contaminated with | Feces, stool, |
| Parasite | DNA | excrement |
| Stool | PCR reaction | Mucus |
| Soil | Enzymatic reaction | |
| Transport media | Sequencing reaction | |
| Blood spots | Labeling reaction | |
| Blood cards | Chemical modified | |
| Swabs | samples | |
| Plants | Contaminated samples | |
| Gel fraction | Diluted samples | |
| Food | | | cards, Swabs, Plants, Gel fraction, and food. The liquid specimens includes, but not limited to, Plasma, Serum, Whole blood, Buffy coat, Bone marrow, Cell suspension, Saliva, Urine, Biofluids, Beverage, Water, RNA contaminated with DNA, PCR reaction, Enzymatic reaction, Sequencing reaction, Labeling reaction, Chemical modified samples, Contaminated samples, and Diluted samples. The other biofluid related to clinical specimens includes Cerebrospinal fluid, Gastric juice, Pleural effusion, Ascites, Synovial fluid, Tears, Semen, Sweat, Sputum, Cervical and vaginal secretions, Feces, stool, excrement, and Mucus.

Protection of Specimens and Biomolecules

Integration of preparation methods including protection, isolation and alteration is the most important technology breakthrough in this invention. The Biomolecules in specimens tend to degradation due to the degrading activities of endogenous Dnase, Rnase, proteinase, lipase, carbohydrase, and other enzymes. Inhibition of these enzymes in specimens or in lysate of specimens is critical for isolation intact biomolecules. The histological structure and micromorphology of specimens is also important in providing normal or pathological information for the specimens, which has been well established in medical practices as pathology. Protection of morphology of specimens and protection intactness of biomolecules in specimens are critical for using specimens and biomolecules in biomedical research and diagnostics. Conventionally different products or kits with different reagents are used in protection or isolation of specimens and biomolecules because the reagents used for protection and for isolation are contradicted or conflict to each other. This is why commercial available protection products and isolation products are separated categories. Conventionally, the specimens were protected in one product and biomolecules were isolated from the protected specimens in other product. In this invention, the protection reagents and isolation reagents are integrated into one single product which protect specimens first and isolate biomolecules from the protected specimens subsequently in the same reagents.

Protection of Histological Structure and Micromorphology of Specimens:

The mouse liver tissue specimen and human lung cancer tissue specimens are stored in the 1×PLIS (Protection-Lysis-Inhibition-Separation) solution from the core module. Volume of 1×PLIS solution is 10 times of volume of tissue specimens. Tissue specimens were slide into 5 mm in thickness. Half of tissue specimens in 1×PLIS solution are stored at 4° C. for 10 days. Half of same tissue specimens are stored at −80° C. without 1×PLIS solution as control. Tissue specimens were taken out from 1×PLIS solution and soaked in PBS for 1 hour with two changes of PBS. Mouse liver tissue specimens are used for frozen tissue section. Human lung cancer tissue specimens are used for FFPE (Formalin Fixed Paraffin Embedded) tissue section. Preparation of frozen tissue section and PPFE tissue section is carried out by routine methods.

As shown in Panel A of FIG. 3, the histological structures and micromophology of frozen tissue section from mouse tissue protected in 1×PLIS solution at 4° C. for 10 days did not have noticeable change and is similar to the control tissue section from mouse tissue stored at −80° C. for 10 days in Panel B. The histological structures and micromophology of FFPE tissue section from human lung cancer tissue protected in 1×PLIS solution at 4° C. for 10 days did not have noticeable change in Panel C, which are similar to the control FFPE tissue section from human lung cancer tissue stored at −80° C. for 10 days in Panel D. Store tissue specimens in 1×PLIS solution at 4° C. for 10 days did not cause noticeable change in histological Structure and Micromorphology of Specimens. 1×PLIS solution protects or maintains the histological Structure and Micromorphology of Specimens.

Protection of Biomolecules from Degradation in Specimens and in Lysate of Specimens:

The mouse liver tissue specimens are stored in the 1×PLIS solution from the core module. Volume of 1×PLIS solution is 10 times of volume of tissue specimens. Tissue specimens were slide into 5 mm in thickness. Half of tissue specimens in 1×PLIS solution are stored at 4° C. for 10 days. Half of same tissue specimens are stored in PBS as control. Tissue specimen stored in 1×PLIS solution was homogenized directly in the same 1×PLIS solution for storage. Tissue specimens stored in PBS was taken out and put in to 1×PLIS solution at 10 times of volume of tissue specimens for homogenization. Homogenization of tissue specimens was carried out at room temperature. The lysate was left at room temperature for five minutes. The DNA, Large RNA/mRNA, Small RNA/miRNA, protein, lipid, carbohydrate, and metabolite were isolated without Affinity column. See Example 5 for detail protocols for simultaneous isolation of DNA, Large RNA/mRNA, Small RNA/miRNA, protein, lipid, carbohydrate, and metabolite from the same piece of specimen. As seen in FIG. 4, DNA, Large RNA/mRNA, Small RNA/miRNA and protein isolated from tissue specimen stored in 1×PLIS solution for 10 days are intact and not degraded (Lane 2, 4, 6, and 8). DNA, Large RNA/mRNA, Small RNA/miRNA and protein isolated from tissue specimen stored in PBS for 10 days are degraded (Lane 1, 3, 5, and 7), in which Large RNA/mRNA and Small RNA/miRNA degraded most severe, and protein degraded mildly by losing a large band. The 1×PLIS solution protects the biomolecules from degradation in specimens when store the tissue specimen in 1×PLIS solution up to 10 days.

The cell lysate in 1×PLIS are stored in 4° C. up to 20 days. See Example 6 for detail protocols for simultaneous isolation of DNA, Large RNA/mRNA, Small RNA/miRNA, protein, lipid, carbohydrate, and metabolite from the same piece of specimen with affinity columns. As seen in FIG. 5, DNA, Large RNA/mRNA, and Small RNA/miRNA are not degraded up to 10 days and 20 days. The yields of Large RNA/mRNA and Small RNA/miRNA are slightly decreased although they are not degraded at 20 days. The protein is not degraded up to 20 days and yield of protein is not changed. The 1×PLIS solution in lysate of specimens protects the biomolecules from degradation up to 10 days.

There is no prior art claimed that lysis solution can protect the histological structure and micromorphology of specimens, protect biomolecules in specimens or in the lysate of specimens for such long period.

Versatile Preparation of a Vast Variety of Specimens

2×PLIS solution in this invention can prepare both solid specimens and liquid specimens. 1×PLIS diluted from 2×PLIS solution can prepare solid specimens including tissues, cells, plant, and microorganisms as listed in Table 6. 2×PLIS solution can be used directly for preparation of the same volume of liquid specimens including plasma, serum, and biofluid as listed in Table 6. 1.5×DAP solution can prepare gel slice specimens containing biomolecules. With Release Solution and 20× Release Enhancer as Plug-in modules, 2×PLIS solution and 1.5×DAP solution can prepare FFPE tissue sections; with 5×MN as Plug-in modules, 2×PLIS solution and 1.5×DAP solution can prepare mitochondria specimens and nucleic specimens; with 2×PP Remover as Plug-in modules, 2×PLIS solution can prepare plant specimens rich in Polysaccharide and polyphenol; with enzyme as Plug-in modules, 2×PLIS solution can prepare microorganism specimens; with DNase as Plug-in modules, 2×PLIS solution and 1.5×DAP solution can prepare RNA specimens contaminated with DNA; and with solid phase binding materials, automation instruments and others as Plug-in modules, 2×PLIS solution and 1.5×DAP solution can automated prepare specimens aforementioned.

Systems Isolation of Systems Biomolecules from the Same Piece of Specimen Simultaneously:

The systems isolation method in this invention can isolate systems biomolecules including DNA/ccfDNA, Large RNA/mRNA/ccfRNA, Small RNA/miRNA/ccfmiRNA, Protein, Lipid, Carbohydrate, and metabolites simultaneously from tissue, cultured cell, plant, bacteria, serum/plasma, blood, and biofluid. DNA/ccfDNA, Large RNA/mRNA/ccfRNA, Small RNA/miRNA/ccfmiRNA, protein, Lipid, Carbohydrate, and metabolites are mixed in specimen or in lysate of specimen. Separations of them from each other before isolation and purification are the critical steps. This invention separates Large RNA/mRNA/ccfRNA from DNA/ccfDNA, Small RNA/miRNA/ccfmiRNA, protein, Lipid, Carbohydrate, and metabolites by a differential centrifugation for 5 minutes without phenol/chloroform extraction and without solid phase binding materials; this invention separates DNA/ccfDNA from Small RNA/miRNA/ccfmiRNA, protein, Lipid, Carbohydrate, and metabolites by differential precipitation for 2 minutes, or by differential solid phase binding for 1 minute, without phenol/chloroform extraction; this invention separates Small RNA/miRNA/ccfmiRNA from protein, Lipid, Carbohydrate, and metabolites by a differential precipitation for 5 minutes, or by differential solid phase binding for 1 minute, without phenol/chloroform extraction; this invention separates protein from Lipid, Carbohydrate, and metabolites by a differential precipitation for 5 minutes without phenol/chloroform extraction and with or without solid phase binding materials for nucleic acid; this invention separates lipid from other biomolecules by Trimethylene bromochloride extraction; and this invention separates carbohydrate from other biomolecules by differential solid phase binding. After separation from each other, DNA/ccfDNA, Large RNA/mRNA/ccfRNA, Small RNA/miRNA/ccfmiRNA, protein, Lipid, Carbohydrate, and metabolites can be isolated and purified individually or simultaneously from the same specimen. The separations are so efficiency and effective that purify, yield and function of isolated DNA/ccfDNA, Large RNA/mRNA/ccfRNA, Small RNA/miRNA/ccfmiRNA, and protein are better than or comparable with the best methods available to public.

The detail protocols see Example 5 and Example 6. In Example 5 the systems isolation methods are differential centrifugation and differential precipitation methods without using affinity column for isolation DNA, Large RNA/mRNA and Small RNA/miRNA. In Example 6 the systems isolation methods are differential centrifugation and differential solid phase binding methods using affinity column for isolation DNA, Large RNA/mRNA and Small RNA/miRNA. Both methods have achieved similar results and performance. DNA, Large RNA/mRNA, Small RNA/miRNA and protein in FIG. 4 were isolated with differential centrifugation and differential precipitation methods without using affinity column for isolation DNA, Large RNA/mRNA and Small RNA/miRNA. DNA, Large RNA/mRNA, Small RNA/miRNA and protein in FIG. 5 were isolated with differential centrifugation and differential solid phase binding methods using affinity column for isolation DNA, Large RNA/mRNA and Small RNA/miRNA. The data for lipid, carbohydrate and metabolite were included in future patent application due to the lengthy and complicated specification in this application.

Table 5 shows the representative Biomolecules that the invention can isolated and Table 6 shows the representative specimens that the invention isolates from. There is no prior art claimed that it can separate, isolate and purify DNA/ccfDNA, Large RNA/mRNA/ccfRNA, Small RNA/miRNA/ccfmiRNA, protein, lipid, carbohydrate, and metabolite individually or simultaneously from the same specimen without phenol/chloroform extraction and without solid phase binding materials for nucleic acid.

Alteration of Biomolecules

Some biomolecules need to be altered for further qualitative or quantitative measurements or applications. The alterations of biomolecules include the alteration in molecular size, alteration in chemical groups on the biomolecules or alteration in composition of biomolecules. Many alterations of biomolecules are based on chemical and enzymatic reactions. The chemistry in the core module of this invention can protect the biomolecules in the chemical alteration, such as in DNA conversion by harsh chemicals for methylation analysis, or decontaminate unwanted chemicals and enzymes after alteration of biomolecules. Although the core module of this invention can perform a limited number of alterations, the most alterations of Biomolecules usually require extra steps beyond the core module of this invention can do. The invention has created an affiliated system with Plug-in modules or solutions as components for extending to specific applications, such as DNA fragmentation, DNA labeling and RNA labeling. These Plug-in modules or solutions are designed as Plug-and-Play to the core module of this invention. Similar to a microphone or web camera for a computer, the microphone can be plugged to computer and play without extra operating system.

The compatibility between the quality or characteristics of isolated biomolecules and the requirements for alteration of the biomolecules was a troublesome issue in conventional methods and products. The existing conventional methods or products for isolation of biomolecules are designed as solo product for merely isolation of biomolecules. The downstream applications of isolated biomolecules were not or impossible fully considered in the design of final the quality or characteristics of isolated biomolecules. Therefore, the isolated biomolecules by product from vendor A may not be compatible to the requirement of product for alteration of biomolecules provided by vendor B. Each product for alteration of biomolecules has to be figured out how to be compatible with the protection or decontamination of biomolecules isolated by the products from different vendors. This invention has solved this incompatible issue or problem and there is no prior art claimed that it can isolate biomolecules and alter biomolecules in the relationship of the core module with Plug-in modules or solutions.

Integration of Protection Method, Systems Isolation Method, and Alteration Method Eventually, the aforementioned three incompatible methods of preparation, i.e. protection, isolation and alteration are integrated synchronously into one comprehensive method by this invention. In this comprehensive method, the protection method protects histological structure or micromorphology of specimens and protects the intactness of biomolecules in specimens or in lysate of specimens. The systems isolation method isolates DNA/ccfDNA, Large RNA/mRNA/ccfRNA, Small RNA/miRNA/ccfmiRNA, protein, lipid, carbohydrate, and metabolite simultaneously or individually from the same piece of specimen. The alteration method alters the characteristics of biomolecules, such as conversion of DNA for methylation analysis, DNA fragmentation, DNA labeling or RNA labeling. Conventionally, the protection, Isolation and alteration of specimens and biomolecules are distinct processes with different solutions, reagents or chemicals, which are not compatible to each other in prior arts. They are presented to users as individual, different and non-related methods or products, which render to inconvenience, complicated procedure, higher cost, and waste of resources. The integrated preparation methods of protection, systems isolation and alteration for specimens and biomolecules in this invention will greatly enhance the effectiveness and efficiency in preparation of specimens and biomolecules, and provide the systems biomolecules for systems diagnostics, systems medicine, systems biology, and other systems approaches in many disciplines.

Conventionally the chemicals or reagents used in protection are contradicted or conflict to the chemicals or reagents used in isolation and alteration methods. For example, biomolecules in specimens can be protected or preserved in high concentration of ammonium sulfate in RNAlater U.S. Pat. No. 6,204,375. But the biomolecules cannot be isolated with preservation solution due to precipitation of protein by extremely high concentration of ammonium sulfate. The chemicals or reagents used in product for isolation of DNA, RNA, and protein, such as Tri reagents in U.S. Pat. No. 5,346,994, can neither protect the histological structure or micromorphology of specimens nor alter the biomolecules, which also have to use toxic phenol and chloroform in the process. In addition, the isolation of DNA and protein in U.S. Pat. No. 994 is very troublesome with lower yield and compromised quality. The commercial available product for alteration of DNA, such as EZ DNA methylation Kit from Zymo research is not able to protect specimens or biomolecules, and cannot isolate biomolecules from specimens. In this invention, many chemicals, reagents, solutions, procedures and protocols have been tested extensively to identify the compatible solutions and methods that can protect, isolate and alter the specimens and biomolecules simultaneously and can integrate the three methods together synchronously. Eventually, certain compatible solutions and methods were created by optimizing the comprehensive parameters including compositions, contents, concentrations, ratios, sequence of use, formulations, temperature, pH, storage, transportation, special application, compatibility, protection, systems isolation, alteration, lysis, inhibition, separation, decontamination, precipitation, binding, prevention of side effect, removal of inhibitor, purification, automation, broad coverage of biomolecules, broad coverage of specimens, quality of output, working condition, easy to use, simple and fast procedure, effective and efficiency, cost effectiveness, safety to users and environments, low carbon consumption in social and economic consideration, and other numerous conditions and issues on a vast selection of chemicals, reagents, substances, materials, and method. The most compatible solutions and methods with broad key functions, such as protection, isolation and alteration are selected as the core module for product and method with integration of the preparation methods including protection, isolation and alteration of specimens and biomolecules, which was the core module later in open module technology. The core module from this invention is one of the example solutions and methods for compatible application in protection, isolation and alteration of specimen and biomolecules with most fulfillments of aforementioned comprehensive parameters.

There are two solutions in the core module, 2×PLIS solution (Abbreviation of Protection-Lysis-Inhibition-Separation) and 1.5×DAP solution (Abbreviation of Decontamination, Alteration, Protection and Purification). Some key features to reflect the compatibility and integration in the core module are briefed as follows. The 2×PLIS is compatible to most solid specimens and liquid specimens. Use 2×PLIS solution for liquid specimen at 1:1 ratio to lyse the solid particles in liquid specimens. Use 1×PLIS (pre-diluted 2×PLIS with H2O) to lyse the solid specimen. 1×PLIS solution can protect histological structure of specimen and protect the biomolecules in specimen or lysate of specimen. The broad systems biomolecules can be isolated subsequently and directly from the protected specimen in PLIS solution. The PLIS solution completely lyses the solid specimens and liquid specimens containing solid particles such as cells and exosomes. The PLIS solution also inhibits effectively activities of endogenous Dnase, Rnase, Proteinase, lipase, carbohydrase and other degrading enzyme. The large RNA/mRNA/ccfRNA can be separated from DNA/ccfDNA, small RNA/miRNA/ccfmiRNA, protein, lipid, carbohydrate and metabolite by differential centrifugation in 1×PLIS solution. The DNA/ccfDNA, Small RNA/miRNA/ccfmiRNA, protein, lipid, carbohydrate and metabolite can be separated from each other later with minimum efforts. The degradation of the large RNA/mRNA/ccfRNA was prevented by decontamination and protection function in 1.5×DAP solution. The DNA/ccfDNA, Small RNA/miRNA/ccfmiRNA, and protein are differentially precipitated in 1×PLIS solution or differentially bound to solid phase for purification. The ccfDNA, ccfRNA and ccfmiRNA can be automated isolated from plasma or serum manually or by automation instrument to meet clinical requirement. In alteration application, the DAP solution separates the impurities, such as proteins for example, from DNA and facilitate the alteration of DNA in completed DNA conversion for methylation analysis. The DAP solution protects the DNA in DNA conversion and enhance the performance for DNA methylation assay. The DAP solution also inactivate and decontaminate the modifying reagents from altered DNA or RNA. The purity and intactness of biomolecules isolated by the core module are better or comparable to conventional methods, but it was operated and prepared at room temperature with easy to use, simple and fast procedure. The effectiveness and efficiency of preparation by the core module are higher than conventional methods and products, and are featured with low cost of materials and labors. Thanks to removal of toxic materials, phenol and chloroform from conventional isolation solutions, the solutions in the core module is safer to user and environments than conventional methods and products. As the solid phase binding materials are not required in the core module the low carbon consumption is achieved in application of the core module for preparation of specimens. Therefore, the core module from this invention prepared the specimens with compatible functions and applications in protection, isolation and alteration of specimens and biomolecules with most fulfillments of aforementioned comprehensive parameters.

This invention has created and initiated the Integrated Versatile and Systems Preparation of Specimens as illustrated in FIG. 6 supported by the core module with differential precipitation methods, which include key methods in protection of specimen and biomolecules, differential centrifugation, decontamination, and differential precipitation for isolation of biomolecules, and alteration of biomolecules. As request from research community for the function of solid phase binding method for isolation of nucleic acid, this invention has integrated the differential solid phase binding materials into the Integrated Versatile and Systems Preparation of Specimens as illustrated in FIG. 7 supported by the core module plus differential solid phase binding methods, which include key methods in protection of specimen and biomolecules, differential centrifugation, decontamination, and differential Solid Phase Binding for isolation of biomolecules, and alteration of biomolecules. Inspired by the integration of the solid phase binding materials into the Integrated Versatile and Systems Preparation of Specimens, the concept of opening the Integrated Versatile and Systems Preparation of Specimens to other functions, emerging functions and custom functions are further invented to free the limitations of the core module and to expand the functions and applications of the core module. The open module technology is therefore invented to integrate more existing and extra functions and to accept and adopt emerging and custom functions into the Integrated Versatile and Systems Preparation of Specimens.

Open Module Technology: Core Module and Plug-in Modules

The open module technology was created based on the extensive selection and optimization of compatible solutions and methods from a vast selection of chemicals, reagents, substances, materials, and methods according to the comprehensive parameters including compositions, contents, concentrations, ratios, sequence of use, formulations, temperature, pH, storage, transportation, special application, compatibility, protection, systems isolation, alteration, lysis, inhibition, separation, decontamination, precipitation, binding, prevention of side effect, removal of inhibitor, purification, automation, broad coverage of biomolecules, broad coverage of specimens, quality of output, working condition, easy to use, simple and fast procedure, effective and efficiency, cost effectiveness, safety to users and environments, low carbon consumption in social and economic consideration, and other numerous conditions and issues aforementioned. After the extensive selection and optimization, many compatible solutions and methods have been identified. The open module technology then arranges, organizes, consolidates, and integrated these compatible solutions and methods in logical, rational and practical ways as follows. The most compatible solutions and methods with broad key functions, such as protection, isolation and alteration are selected as the core module. The core module contains two solutions, PLIS solution (Protection-Lysis-Inhibition-Separation) and DAP solution (Decontamination, Alteration, Protection and Purification) as aforementioned. Other compatible solutions and methods with some specific functions are used as Plug-in modules to free the limitation of the core module and to expand the functions of the core module. The core module has integrated protection method, systems isolation method, and alteration method for major functions in preparation of specimens. The Plug-in modules are designed to free the limitation of the core module and to expand the functions of the core module.

The detailed functions of the core module have been described in the section of "Integration of protection method, systems isolation method, and alteration method", which were supported by the most compatible solutions and methods with broad key functions. However, the core module still has some limitations for some special specimens, special biomolecules and special functions in preparation of specimens. For example, the core module, by itself, cannot isolate the DNA, RNA, and miRNA from FFPE tissue section. With addition of proteinase and digestion solutions, the core module can isolate the DNA, RNA, and miRNA from FFPE tissue section. The compatibility of the proteinase and digestion solutions to the core module has been explored and validated by open module technology. The proteinase and digestion solutions become a Plug-in module for the core module. For the users having the core module already, only adding one or two components to the existing core module with minimum expense, they can free the limitation of the core module and add the function of isolating the DNA, RNA, and miRNA from FFPE tissue section to their existing core module. But in commercially available and conventional products or kits, adding proteinase and digestion solutions to existing product or kit from a vendor may not work most likely or works poorly because no compatibility study has been conducted in such combination by vendor. It will waste a lot of time and resource for users to find out the compatible solutions and methods. The users have to buy another whole kit for isolation of DNA, RNA or miRNA from FFPE tissue section. The users have to collect many different kinds of products or kits from different vendors to carry out more tasks if users want to work on other functions of specimen preparation. The users end up with more whole kits with extra and non-related solutions in hand and eventually throw them away because most users just used a portion of kit for testing and proving the concepts in research. This is a big waste of budget for the users and a huge waste of resources for biomedicine field as a whole. Fortunately, the core module and Plug-in modules from open module technology in this invention can solve this wasting problem with better performance and higher quality of biomolecules isolated from specimens.

The open module technology has identified and created many plug-in modules compatible to the core modules through the extensive selection and optimization of compatible solutions and methods from a vast selection of chemicals, reagents, substances, materials, and methods, and through arrangement, organization, consolidation, and integration of these compatible solutions and methods in logical, rational and practical ways. The other examples of plug-in modules include, but not limited to, 1) solid phase binding materials for nucleic acid binding and purification as aforementioned; 2) DNA degrading enzymes for DNA fragmentation; 3) conversion reagents and conversion enhancer in DNA conversion for DNA methylation assay; 4) Mitochondria solution for isolation of mitochondria DNA and nucleic DNA; 5) Polysaccharide and polyphenol remover for isolation of biomolecules from plant tissues rich in Polysaccharide and polyphenol; 6) lysozyme or lyticase for systems isolation of biomolecules from bacteria or yeast; 7) S1, S2, and S3 for isolation of plasmid DNA from bacteria; 8) DNA degrading enzymes for DNA removal; 9) DNA labeling mix for DNA labeling; 10) RNA labeling mix for RNA labeling; 11) Trimethylene bromochloride for lipid extraction and Con-A column for solid phase binding carbohydrate, which are for adding the functions of isolation of lipid, carbohydrate and metabolite to core module; and 12) proteinase and digestion solutions isolating the DNA, RNA, and miRNA from FFPE tissue section as aforementioned. Beside the solutions served as Plug-in module, the solid phase binding materials such as column with glass fiber filter or magnetic beads are served as other Plug-in modules to extend the core invention module to a specific application for solid phase isolation of biomolecules with high purity, and extend to the application of automation with assistant of another plug-in module, such as automated sample preparation instrument. The equipment or instrument for automated processing specimens and biomolecules include tissue homogenizer, liquid handler, magnetic separator, vacuum, and centrifuge. The types of plug-in modules are unlimited as long as they are compatible to the core module and other plug-in modules.

The examples of plug-in modules herein are identified and created by open module technology during the creation of this invention. The Table 4 summarizes the functional overview of the core module and plug-in modules and relationships among the core module and plug-in modules. The core module itself can perform some key functions, while plug-in modules free the limitations of the core module and expand extensively the functions of the core module. It is worthwhile to point out that not only one plug-in module can work with the core module on one specific function, but two or more plug-in modules can work with the core module on one specific function with well compatibility and coordination. Besides the core module and plug-in modules listed in Table 4, there are more emerging plug-in modules are under development by open module technology through the extensive selection and optimization of compatible solutions and methods from a vast selection of chemicals, reagents, substances, materials, and methods, and through arrangement, organization, consolidation, and integration of these compatible solutions and methods in logical, rational and practical ways. The custom plug-in modules for special functions requested by users are also under development by open module technology. The list of plug-in modules are growing longer and longer. Of cause, the core module is also under continuously re-evaluation and improvement by open module technology. The new version of the core module or new core modules will come out for meeting a vast variety of needs in preparation of specimen.

The open module technology comprises two key processes, 1) the extensive selection and optimization of compatible solutions and methods from a vast selection of chemicals, reagents, substances, materials, and methods; and 2) the arrangement, organization, consolidation, and integration of these compatible solutions and methods in logical, rational and practical ways. The chemicals, reagents, substances, materials, and methods are major materialized players in this invention as detailed in following sections, and optimization, arrangement, organization, consolidation, and integration are the talents of the human brain. In current status of the invention, the core module plays the major roles in protection, isolation, and alteration of specimens and biomolecules, the plug-in modules as individual module or combined modules extend the core invention to a specific function or application as the name of plug-in modules indicated. The core module and plug-in modules are designed as an open system and it can take more Plug-in modules for more functions or applications. The emerging Plug-in modules include, but not limited to, collection modules for collecting specimens and biomolecules, preservation modules for preserving specimens and biomolecules, storage modules for storing specimens and biomolecules, process modules for processing specimens and biomolecules, banking modules for specimens and biomolecules banking, transportation modules for transporting specimens and biomolecules, distribution modules for distributing specimens and biomolecules, alteration modules for altering specimens and biomolecules, modification modules for modifying specimens and biomolecules, application modules for application of specimens and biomolecules, analysis modules for analysis of specimens and biomolecules, detection modules for detection of specimens and biomolecules, and other modules for specimens and biomolecules. Users also can design their own plug-in modules to work with the core module or other plug-in modules according to a variety of protocols in EXAMPLES section.

Reagents, Chemicals, Solutions, and Materials for Open Module Technology

A variety of solutions, reagents, chemicals, and enzymes at different combinations compose the core module that contains lysis solution and decontamination solution, and plug-in modules with a vast variety of solutions. For explanation purposes, here are some selected examples from many candidates for these solutions. The lysis solution comprises Sodium lauroyl sarcosinate (Sarkosyl), Sodium dodecyl sulfate (SDS), Tween-20, Triton X-100, Tris(hydroxymethyl) aminomethane (Tris), Tris(2-carboxyethyl)phosphine hydrochloride (TCEP), cesium chloride (CsCl), Guanidine thiocynate, Guanidine hydrochloride, urea, sodium chloride (NaCl), lithium chloride (LiCl), Sodium Citrate, and alcohol for protection, lysis, inhibition, separation, isolation and purification in preparation of biomolecules. The decontamination solution contains sodium iodide, Ammonium acetate, Sodium acetate, Sodium Citrate, sodium chloride (NaCl), and Ethylenediaminetetraacetic acid disodium salt dihydrate (EDTA) for removal of contaminants, alteration, protection and purification of biomolecules in preparation of biomolecules.

The Plug-in modules or solutions as each individual modules consist of a vast variety of chemicals, reagents, enzyme, solution, substances or materials such as: 1) the solid phase binding material for nucleic acid binding and purification including, but not limited to, affinity column containing glass fiber or magnetic beads; 2) the solution containing DNA degrading enzymes, such as Dnase or Fragmentase (NEB) for DNA fragmentation; 3) the solutions containing conversion reagents Sodium Bisulfite and Hydroquinone and conversion enhancer in DNA conversion for DNA methylation assay; 4) Mitochondria solutions containing sucrose for isolation mitochondria DNA and nucleic DNA; 5) solutions containing Hexadecyltrimethylammonium bromide (CTAB) and Polyvinylpyrrolidone, average mol wt 40,000 (PVP40) for removal of polysaccharide and polyphenol in isolation of biomolecules from plant tissues rich in Polysaccharide and polyphenol; 6) Solution containing lysozyme, lyticase or Zymolyase for lysis of bacteria or yeast in systems isolation of biomolecules, DNA, large RNA/mRNA, Small RNA/miRNA, protein, lipid, carbohydrate and metabolite from bacteria or yeast; 7) the solutions S1, S2, and S3 containing EDTA, Sodium hydroxide (NaOH) and potassium acetate for isolation of plasmid DNA from bacteria; 8) the solution containing DNA degrading enzymes, such as Dnase for DNA removal from RNA; 9) the solution containing DNA polymerase or reverse transcriptase in DNA labeling mix for DNA labeling; 10) the solution containing RNA polymerase in RNA labeling mix for RNA labeling; 11) Trimethylene bromochloride for lipid extraction and Concanavalin A (Con-A) column and methyl-α-D-glucopyranoside for solid phase binding of carbohydrate, which are for adding the functions of isolation of lipid, carbohydrate and metabolite to core module; 12) the solutions containing protein degrading enzymes, proteinase and nucleic acid degrading enzyme such as Dnase or RNase for isolating the DNA, RNA, and miRNA from FFPE tissue section; and 13) the solutions containing Magnesium chloride ($MgCl_2$), Calcium chloride ($CaCl_2$), and Manganese chloride ($MnCl_2$) as buffer solutions. The equipment or instrument for automated processing specimens and biomolecules include tissue homogenizer, liquid handler, magnetic separator, vacuum, and centrifuge.

Amount and Concentration of Reagents, Chemicals and Other Materials in Solutions or Usages:

The preferred concentration of the chemicals, reagents and enzymes used in the lysis solution, decontamination solution and Plug in solutions are varied in broad ranges. The Sarkosyl is at 0.1-20%, SDS is at 0.1-20%, Tween-20 is at 0.1-30%, Triton X-100 is at 0.1-30%, Tris is at 10-900 mM, TCEP is at 10-100 mM, Cesium chloride (CsCl) is at 0.5-9 M, Guanidine thiocynate is at 1-5.5 M, Guanidine hydrochloride is at 1-8 M, urea is at 2-6 M, sodium chloride (NaCl) is at 0.1-5 M, lithium chloride (LiCl) is at 0.3-18 M, Sodium Citrate is at 20-100 mM, alcohol is at 0-95%, sodium iodide is at 1-5 M, Ammonium acetate at 1-10 M, Sodium acetate is at 0.1-5 M, EDTA is at 0.1-50 mM, Trimethylene bromochloride at 100%, Concanavalin A (Con-A) column use as instructed from manufacture, methyl-α-D-glucopyranoside is at 0.1-2 M, Dnase is at 200-2000 u/ml, Fragmentase (NEB) as manufacture instruction, Sodium Bisulfite is at 30-50%, Hydroquinone is at 0.5-2%, sucrose is at 200-400 mM, CTAB is at 0.2-8%, PVP40 is at 0.2-8%, lysozyme is at 0.2-2 mg/ml, lyticase or Zymolyase as manufacture instruction, NaOH is at 0.1-5N, potassium acetate is at 0.2-5 M, DNA polymerase is at 4-400 u/ml, Reverse transcriptase is at 20-20000 u/ml, and RNA polymerase is at 100-10000 u/ml, Affinity column containing glass fiber and magnetic beads amount is depended on the amount of biomolecules to be isolated. Proteinase is at 0.5-3 mg/ml, Rnase is at 20-200 mg/ml. $MgCl_2$ is at 10-400 mM, $CaCl_2$ is at 20-100 mM, and $MnCl_2$ is at 1-50 mM. One Affinity column or Concanavalin A (Con A) Sepharose™ 4B beads is for each isolation, magnetic beads amount is depended on the amount of biomolecules to be isolated.

The concentrations of some chemicals and reagents are further preferred. The Sarkosyl is at 0.1%, 0.2%, 0.3%, 0.4%, 0.5%, 1%, 5%, 10%, 15%, 18% and 20%. SDS is at 0.1%, 0.2%, 0.3%, 0.4%, 0.5%, 1%, 5%, 10%, 15%, 18% and 20%. Tween-20 is at 0.1%, 0.2%, 0.3%, 0.4%, 0.5%, 1%, 5%, 10%, 15%, 18%, 20%, 22%, 24%, 26%, 28% and 30%. Triton X-100 is at 0.1%, 0.2%, 0.3%, 0.4%, 0.5%, 1%, 5%, 10%, 15%, 18%, 20%, 22%, 24%, 26%, 28% and 30%. TCEP is at 10 mM, 20 mM, 30 mM, 40 mM, 50 mM, 60 mM, 70 mM, 80 mM, 90 mM and 100 mM. Cesium chloride (CsCl) is at 0.5M, 0.75M, 1M, 1.25M, 1.5M, 1.75M, 2M, 2.5M, 3M, 4M, 5M, 6M, 7M, 8M and 9 M, Guanidine thiocynate is at 1M, 1.25M, 1.5M, 1.75M, 2M, 2.5M, 3M, 4M, 5M, and 5.5M, Guanidine hydrochloride is at 1M, 1.25M, 1.5M, 1.75M, 2M, 2.5M, 3M, 4M, 5M, 6M, 7M, and 8M. Urea is at 2M, 2.5M, 3M, 4M, 5M, and 6M. Sodium chloride (NaCl) is at 0.1M, 0.2M, 0.3M, 0.4M, 0.5M, 0.75M, 1M, 1.25M, 1.5M, 1.75M, 2M, 2.5M, 3M, 4M, and 5M. Lithium chloride (LiCl) is at 0.3M, 0.4M, 0.5M, 0.75M, 1M, 1.25M, 1.5M, 1.75M, 2M, 2.5M, 3M, 4M, 5M, 6M, 7M, 8M, 9 M, 10M, 11M, 12M, 13M, 14M, 15M, 16M, 17M and 18 M, Sodium Citrate is at 20 mM, 30 mM, 40 mM, 50 mM, 60 mM, 70 mM, 80 mM, 90 mM, and 100 mM. Alcohol is at 0%, 5%, 8%, 10%, 11%, 12%, 13%, 14%, 15%, 16%, 17%, 18%, 19%, 20%, 21%, 22%, 23%, 24%, 35%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 72%, 74%, 76%, 78%, 80%, 82%, 84$, 86%, 88%, 90%, 92%, 94$, and 95%. Sodium iodide is at 1M, 1.25M, 1.5M, 1.75M, 2M, 2.5M, 3M, 4M, and 5M. Ammonium acetate at 1M, 1.25M, 1.5M, 1.75M, 2M, 2.5M, 3M, 4M, 5M, 6M, 7M, 8M, 9 M, and 10M. Sodium acetate is at 0.1M, 0.2M, 0.3M, 0.4M, 0.5M, 0.75M, 1M, 1.25M, 1.5M, 1.75M, 2M, 2.5M, 3M, 4M, and 5M. EDTA is at 0.1 mM, 0.5 mM, 1 mM, 2 mM, 4 mM, 6 mM, 8 mM, 10 mM, 15 mM, 20 mM, 25 mM, 30 mM, 35 mM, 40 mM, 45 mM and 50 mM.

Combination and Optimization of Reagents and Chemicals in the Solutions

The combination and optimization of the reagents and chemicals in the solution are the heart and hard tasks in open module technology. The ideal products from this invention can protect, isolate and alter the specimens and biomolecules simultaneously and can integrate the three methods together synchronously. Since there is not prior art to refer, the combination and optimization of reagents and chemicals for such complicated functions and parameters in preparation of specimens are by trial and error method.

With a variety of combination of reagents and chemicals at different concentrations, four solutions as examples that contain sarkosyl, SDS, Tween-20, Triton X-100, Tris, TCEP, cesium chloride, lithium chloride, urea, Guanidine hydrochloride, Guanidine thiocynate, and ethanol can lyse the specimens and separate the Large RNA/mRNA from DNA by a simple differential centrifugation, and protect specimen and biomolecules before or after lysis. The lysis solution 1) contains sarkosyl at 0.2%, SDS at 0.2%, Tween-20 at 0.5%, Triton X-100 at 0.5%, Tris at 100 mM, TCEP at 50 mM, cesium chloride (CsCl) at 4 M, lithium chloride (LiCl) at 1 M, and urea at 2 M, pH 4.0. The lysis solution 2) contains sarkosyl at 0.2%, SDS at 0.2%, Tween-20 at 0.5%, Triton X-100 at 0.5%, Tris at 100 mM, TCEP at 50 mM, cesium chloride (CsCl) at 1 M, lithium chloride (LiCl) at 6 M, and Guanidine hydrochloride at 1 M, pH 6.0. The lysis solutions 3) contains sarkosyl at 0.2%, SDS at 0.2%, Tween-20 at 0.5%, Triton X-100 at 0.5%, Tris at 100 mM, TCEP at 50 mM, cesium chloride (CsCl) at 2 M, lithium chloride (LiCl) at 3 M, and ethanol at 14%, pH 8.0. The lysis solutions 4) contains sarkosyl at 0.2%, SDS at 0.2%, Tween-20 at 0.5%, Triton X-100 at 0.5%, Tris at 100 mM, TCEP at 50 mM, cesium chloride (CsCl) at 1 M, Guanidine thiocyanate at 3 M, and ethanol at 31%, pH 10.0. The decontamination solution contains sodium iodide at 4 M, Ammonium acetate at 2 M, Sodium acetate at 0.3 M, Sodium Citrate at 50 mM, sodium chloride at 0.2 M (NaCl), EDTA at 10 mM, and TCEP at 50 mM, pH 6.0.

The concentrations of reagents and chemicals in the solutions are variable depended on the combination of the reagents and chemicals in the solution and ratio to each other. A reagent or chemical alone can be used at high concentration in one solution combined with one sets of reagents or chemicals, but it can be used at low concentration in another solution when combined with different sets of reagents or chemicals. Some reagents in the solution can be used at very high concentration alone or along with a few other reagents, or can be used at low concentration with more other reagents. The reagents that can be used at wide range concentration include, but not limited to, sarkosyl at 0.1-20%, SDS at 0.1-20%, Tween-20 at 0.1-30%, Triton X-100 at 0.1-30%, Tris at 10-900 mM, TCEP at 10-100 mM, alcohol at 0-95%, sodium iodide at 1-5 M, Ammonium acetate at 1-10 M, Cesium chloride (CsCl) at 0.5-9 M, Guanidine thiocynate at 1-5.5 M, Guanidine hydrochloride at 1-8 M, urea at 2-6 M, sodium chloride (NaCl) at 0.1-5 M, lithium chloride (LiCl) at 0.3-18 M, and etc. Use these reagents alone at higher or highest concentration in the solution is functional, but with other companioned reagents in the solutions, the concentration of the reagents can be lower in the solution and the function of solution could be more comprehensive. There are hardly any general rules or formula in combination and optimization which can predict the outcomes of a solution. But the principles of open module technology are defined, compatibility, performance, comprehensive, integration, expansion, effectiveness, efficiency, user-friendly, cost effective, and environment-friendly.

The open module technology has identified the differential centrifugation method, the differential precipitation method, and Differential Solid Phase Binding method to use the solution for achieving the goal of separation of Large RNA/mRNA/ccfRNA from DNA/ccfDNA. The Large RNA/mRNA and DNA are isolated by differential precipitation method after separation from each other by differential centrifugation shown in Panel A of FIG. 8. The Large RNA/mRNA and DNA are isolated by Differential Solid Phase Binding method with affinity column after separation from each other by differential centrifugation shown in Panel B of FIG. 8. The representative data in FIG. 8 also shows consistent and similar results of achieving the goal of separation of Large RNA/mRNA/ccfRNA from DNA/ccfDNA with different methods.

So far the invention of the open module technology is created based on trial and error method. The solutions in the core module and plug-in module from this invention are carefully formulated according to extensive testing in trial and error. The concept and principle of integrated system preparation of specimen has been approved with solid scientific data as shown in Figures, Tables and Example section. The components in the core module and plug-in modules in following section could be improved and changed with extensive trial and error in the future by inventor or by other skilled people. The outcome of the invention will be better and better through extensive trial and error. Eventually, it becomes trial and success. The outcome of new invention can be better predicted according to the general rules or formula deduced from extensive trial and error and from trial and success based on the creations and principles of this invention.

Solutions and Components in Core Module and Plug-in Modules

One applicable format of the invention comprises the core module and protocols that protect, isolate and alter the specimens. The alternative applicable format of the invention comprises the core module, plug-in modules, and protocols that protect, isolate and alter specimens. The core module consists of the solutions. The plug-in modules consist of a great variety of substances, materials, chemicals, reagents, solutions, columns, instruments equipment, objects, and etc. The examples of plug-in modules are materials for solid phase binding of biomolecules, the equipment or instrument for automated processing specimens and biomolecules, the solutions for special treatments of certain particular specimens, and the solutions for alteration of biomolecules. The solutions served as plug-in modules herein are referred as plug-in solutions.

The solutions used in the format of the core module include one PUS solution at two times concentration (2×) as lysis solution for protection, lysis, inhibition, and separation of specimen and biomolecules. The solutions used in the core module include another solution at 1.5 times concentration (1.5×) as DAP Solution for decontamination, alteration, protection and purification of biomolecules. The 2×PUS solution and the 1.5×DAP solution compose Allzol Kit as core modules and enable the functions and applications of protection, isolation and alteration for most specimens and biomolecules without phenol, chloroform and materials for solid phase binding of biomolecules.

The solutions used in the format of the core module and plug-in modules include one PUS solution at two times concentration (2×) as lysis solution for protection, lysis, inhibition, and separation of specimen and biomolecules; include another solution at 1.5 times concentration (1.5×) as DAP Solution for decontamination, alteration, protection and purification of biomolecules; and include plug-in modules for solid phase binding of biomolecules. Wherein plug-in modules for solid phase binding of biomolecules include, but not limited to, affinity column or magnetic beads for solid phase binding of biomolecules. The 2× lysis solution, the 1.5×DAP solution, and plug-in modules for solid phase binding of biomolecules compose Alliso kit or Allauto Kit respectively and enable the application of protection, isolation and alteration for most biospecimens and biomolecules without phenol and chloroform.

The solutions used in the format of the core module and plug-in modules include additional solutions and components in other format as the plug-in modules for adding more functions or applications to the Allzol Kit and the Alliso Kit or Allauto Kit. The additional solutions as the plug-in modules can play the Plug-and-Play function for the Allzol Kit and the Alliso Kit or Allauto Kit. The additional solutions as the plug-in modules are named herein as Plug-in solutions which include, but not limited to, 1) plug-in solutions working with solid phase binding material for nucleic acid binding and purification; 2) plug-in solutions with DNA degrading enzymes for DNA fragmentation; 3) plug-in solutions with conversion reagents and conversion enhancer in DNA conversion for DNA methylation assay; 4) plug-in solution with Mitochondria solution for isolation of mitochondria DNA and nucleic DNA; 5) plug-in solution with Polysaccharide and polyphenol remover for isolation of biomolecules from plant tissues rich in Polysaccharide and polyphenol; 6) plug-in solutions with lysozyme or lyticase for systems isolation of biomolecules from bacteria or yeast; 7) plug-in solutions with S1, S2, and S3 for isolation of plasmid DNA from bacteria; 8) plug-in solution with DNA degrading enzymes for DNA removal; 9) plug-in solutions with DNA labeling mix for DNA labeling; 10) plug-in solutions with RNA labeling mix for RNA labeling; 11) plug-in solutions with Trimethylene bromochloride for lipid extraction and with solutions working with Con-A column for solid phase binding carbohydrate, which are for adding the functions of isolation of lipid, carbohydrate and metabolite to core module; and 12) plug-in solutions with proteinase and digestion solutions for isolation of the DNA, RNA, and miRNA from FFPE tissue section. The components in other format as the plug-in modules can include materials for automation, such as Affinity column, or magnetic beads, which composed Allauto Kit on top of Allzol Kit, and automated equipment, instruments, tissue homogenizer, liquid handler, magnetic separator, and vacuum; and include other materials, such as incubator, centrifuge, chromatographic instrument, electrophoresis apparatus, fraction collectors, and dryer. Plug-in solutions and the components in other format as the plug-in modules extend and broaden the functions or applications for Allzol Kit and Alliso Kit or Allauto Kit in protection, isolation and alteration of from most specimens and biomolecules to all specimens and biomolecules.

Protocols for Core Module and Plug-in Modules in Separation of DNA/ccfDNA, Large RNA/mRNA/ccfRNA, Small RNA/miRNA/ccfmiRNA, Protein Lipid, Carbohydrate, and Metabolite from Each Other at Different Degrees Biomolecules are separated and isolated after lysis of specimens with PLIS solution from the core module. The separation and systems isolation of biomolecules are carried out by the methods of differential centrifugation, decontamination, differential precipitation and differential solid phase binding. The methods are selectively organized and combined with different conditions, such as different concentration of ethanol in differential precipitation, to create many different protocols and to end up with different and isolated biomolecules with a spectrum of purity and degree of separation. This is the power of open module technology, the combination of the core module and plug-in module, affinity columns for binding of nucleic acid, and Integrated Versatile and Systems Preparation of specimen in this invention herein. The DNA/ccfDNA, Large RNA/mRNA/ccfRNA, Small RNA/miRNA/ccfmiRNA, protein, lipid, carbohydrate and metabolite can be separated and systems isolated individually or simultaneously in five different protocols according to the degree or depth in separation of DNA/ccfDNA, Large RNA/mRNA/ccfRNA, Small RNA/miRNA/ccfmiRNA, and protein from each other. The five different protocols have different arrangement of the adjustment and combination in implements of differential centrifugation, decontamination, differential precipitation, differential solid phase binding and extraction as shown in FIG. 9 and FIG. 10, which result in a variety of isolated biomolecules in separated or mixed status. The "P" after the protocol number indicates differential precipitation method. The "B" after the protocol number indicates the protocols using differential solid phase binding methods. According to these protocols, users can select protocol 1P or 1B for obtaining all DNA/ccfDNA, Large RNA/mRNA/ccfRNA, Small RNA/miRNA/ccfmiRNA, protein, lipid, carbohydrate and metabolite with full separation from each other; select protocol 2P of 2B for getting fully separated Large RNA/mRNA/ccfRNA, protein, lipid, carbohydrate and metabolite, and mixed DNA/ccfDNA and Small RNA/miRNA/ccfmiRNA; select protocol 3P or 3B for getting fully separated Small RNA/miRNA/ccfmiRNA, protein, lipid, carbohydrate and metabolite, and mixed DNA/ccfDNA and Large RNA/mRNA/ccfRNA; and select protocol 4P or 4B and 5P or 5B for getting fully separated protein, lipid, carbohydrate and metabolite, and mixed DNA/ccfDNA, Large RNA/mRNA/ccfRNA, and Small RNA/miRNA/ccfmiRNA.

The Products and Kits Derived from the Invention

A variety of products and kits has been developed from this invention, including, but not limited to, Allzol Kit, Alliso Kit, Allauto Kit derived from the core module, herein referred as the core kits, and a variety of plug-in kits derived from plug-in modules with specific functions on special requests in preparation of specimens.

Allzol kit consists of the core module with PLIS solution and DAP solution only. The Allzol kit alone has the integrated functions of protection, systems isolation, and alteration. PLIS solution protects the histological structure and micro-morphology of specimen, and protects the intactness of biomolecules in specimen and in the lysate of specimen. PLIS and DAP solution isolate the systems biomolecules including DNA/ccfDNA, Large RNA/mRNA/ccfRNA, Small RNA/miRNA/ccfmiRNA, and protein from solid specimens or liquid specimens by differential centrifugation, decontamination, and differential precipitation. DAP solution decontaminates and purifies biomolecules, removes inhibitors and protects biomolecules in alteration. With plug-in kits, the Allzol kit can expand its functions to isolation of lipid, carbohydrate, metabolite from specimens, to systems isolation of biomolecules from special specimens, and to more alterations of biomolecules.

Alliso kit consists of the core module with PLIS solution and DAP solution, and one of plug-in modules, the affinity column as solid phase binding material for nucleic acid. The Alliso kit alone has the integrated functions of protection, systems isolation, and alteration. PLIS solution protects the histological structure and micro-morphology of specimen, and protects the intactness of biomolecules in specimen and in the lysate of specimen. PLIS, DAP solution, and affinity column isolate the systems biomolecules including DNA/ccfDNA, Large RNA/mRNA/ccfRNA, Small RNA/miRNA/ccfmiRNA, and protein from solid specimens or liquid specimens by differential centrifugation, decontamination, differential solid phase binding, and differential precipitation. DAP solution decontaminates and purifies biomolecules, removes inhibitors and protects biomolecules in alteration. With plug-in kits, the Alliso kit can expand its functions to isolation of lipid, carbohydrate, metabolite from specimens, to systems isolation of biomolecules from special specimens, and to more alterations of biomolecules.

Allauto kit consists of the core module with PLIS solution and DAP solution, and one of plug-in modules, the magnetic beads as solid phase binding material for nucleic acid. The Allauto kit alone has the integrated functions of protection, systems isolation, and alteration. PLIS solution protects the histological structure and micro-morphology of specimen, and protects the intactness of biomolecules in specimen and in the lysate of specimen. PLIS, DAP solution, and magnetic beads isolate the systems biomolecules including DNA/ccfDNA, Large RNA/mRNA/ccfRNA, Small RNA/miRNA/ccfmiRNA, and protein from solid specimens or liquid specimens by differential centrifugation, decontamination, differential solid phase binding, and differential precipitation. DAP solution decontaminates and purifies biomolecules, removes inhibitors and protects biomolecules in alteration. With plug-in kits and automated instruments, the Allauto kit can expand its functions to isolation of lipid, carbohydrate, metabolite from specimens, to systems isolation of biomolecules from special specimens, to more alterations of biomolecules, and to automation in system isolation of DNA/ccfDNA, Large RNA/mRNA/ccfRNA, Small RNA/miRNA/ccfmiRNA, and other biomolecules.

The plug-in kits derived from a vast variety of plug-in modules include many different products and Kits. The current representative kits created by the open module technology of this invention include 1) plug-in kit with solid phase binding material for nucleic acid binding and purification; 2) plug-in kit with DNA degrading enzymes for DNA fragmentation; 3) plug-in kit with conversion reagents and conversion enhancer in DNA conversion for DNA methylation assay; 4) plug-in kit with Mitochondria solution for isolation of mitochondria DNA and nucleic DNA; 5) plug-in kit with Polysaccharide and polyphenol remover for isolation of biomolecules from plant tissues rich in Polysaccharide and polyphenol; 6) plug-in kit with lysozyme or lyticase for systems isolation of biomolecules from bacteria or yeast; 7) plug-in kit with S1, S2, and S3 for isolation of plasmid DNA from bacteria; 8) plug-in kit with DNA degrading enzymes for DNA removal; 9) plug-in kit with DNA labeling mix for DNA labeling; 10) plug-in kit with RNA labeling mix for RNA labeling; 11) plug-in kit with Trimethylene bromochloride for lipid extraction and with Con-A column for solid phase binding carbohydrate, which are for adding the functions of isolation of lipid, carbohydrate and metabolite to core module; and 12) plug-in kit with proteinase and digestion solutions for isolation of the DNA, RNA, and miRNA from FFPE tissue section. The plug-in kits can include materials for automation, such as Affinity column, or magnetic beads, which composed Allauto Kit on top of Allzol Kit, and automated equipment, instruments, tissue homogenizer, liquid handler, magnetic separator, and vacuum; and include other materials, such as incubator, centrifuge, chromatographic instrument, electrophoresis apparatus, fraction collectors, and dryer. Plug-in Kits extend and broaden the functions or applications for Allzol Kit and Alliso Kit or Allauto Kit in protection, isolation and alteration of from most specimens and biomolecules to all specimens and biomolecules.

The Protocols for the Products and Kits

Through open module technology, vast varieties of protocols have been developed for the products and Kits from this invention. There are three major groups of protocols, protection protocols, versatile and systems isolation protocols and alteration protocols. The protection protocols include the steps: 1) to protect histological structures and micromorphology of specimens in lysis solution at 4° C. for at least 10 days; 2) to protect intactness of biomolecules in the original specimens by store the original specimens in lysis solution at 4° C. for at least 10 days; 3) to protect the intactness of biomolecules in the lysate of specimens with lysis solution at 4° C. for at least 10 days.

The versatile and systems isolation protocols have broad coverage on different aspects in isolation of biomolecules from different specimens, such as lysis of specimens, inhibition of degrading enzymes, separation of biomolecules, removal of the contaminants, and binding biomolecules to solid phase binding materials. The lysis protocol includes the step of lysis of tissue, cell, plant or other solid specimens in pre-diluted 1× lysis solution, and lysis of plasma, serum, biofluid or other liquid specimens in 2× lysis solution. The inhibition protocols include the step to inhibit Rnase, Dnase and proteinase by incubate the lysate at room temperature for 0 to 600 min or incubate at 4° C. for at least 10 days while the biomolecules are still intact.

The separation protocols include the step to separate Large RNA/mRNA/ccfRNA from DNA/ccfDNA and Small RNA/miRNA/ccfmiRNA by differential centrifugation of the crude lysate of specimens without removing protein, without phenol/chloroform extraction, without binding Large RNA/mRNA/ccfRNA, DNA/ccfDNA or Small RNA/miRNA/ccfmiRNA on solid phase binding materials, or without other treatment to the lysate. The separation protocols also include the step to separate DNA/ccfDNA from Small RNA/miRNA/ccfmiRNA by differential precipitation with centrifugation of the crude lysate of specimens containing 25-35% alcohol or 32% alcohol but without removing protein, without binding DNA/ccfDNA or Small RNA/miRNA/ccfmiRNA on solid phase binding materials, or without other treatment to the lysate. In addition, the protocols include the step to separate DNA/ccfDNA from Small RNA/miRNA/ccfmiRNA by differential solid phase binding with centrifugation of the crude lysate of specimens containing 30-45% or 40% alcohol binding on solid phase binding materials but without removing protein or other treatment to the lysate.

The remove and separation protocols include the steps to remove the contaminants from Large RNA/mRNA/ccfRNA by decontamination with centrifugation in 1×DAP solution and to separate Large RNA/mRNA/ccfRNA from DNA/ccfDNA by differential precipitation or differential solid phase binding with centrifugation of lysate of specimens in the 1×DAP Solution containing 25-35% alcohol or 31% alcohol without or with binding on solid phase binding materials respectively. The protocols include the steps to remove Large RNA/mRNA/ccfRNA from DNA/ccfDNA by differential centrifugation, subsequently to separate DNA/ccfDNA from other biomolecules by differential precipitation, and to isolate DNA/ccfDNA by centrifugation of the crude lysate of specimens containing 25-35% alcohol or 32% alcohol but without removing protein, without binding on solid phase binding materials, or without other treatment to the lysate. In addition, the protocols include the step to remove Large RNA/mRNA/ccfRNA from DNA/ccfDNA by differential centrifugation, to bind DNA/ccfDNA on solid phase binding materials and isolate DNA/ccfDNA by differential solid phase binding with centrifugation of the crude lysate of specimens containing 30-45% or 40% alcohol binding on solid phase binding materials but without removing protein or without other treatment to the lysate.

The separation protocols include the steps to separate Large RNA/mRNA/ccfRNA from other biomolecules by differential centrifugation, to remove contaminants from Large RNA/mRNA/ccfRNA by decontamination in DAP solution with centrifugation, to separate Large RNA/mRNA/ccfRNA from DNA/ccfDNA by differential precipitation, and to isolate Large RNA/mRNA/ccfRNA by centrifugation of the lysate of specimens in 1×DAP Solution containing 25-35% alcohol or 31% alcohol without binding on solid phase binding materials. In addition, The protocols includes the steps to separate Large RNA/mRNA/ccfRNA from other biomolecules by differential centrifugation, to remove contaminants from Large RNA/mRNA/ccfRNA by decontamination in DAP solution with centrifugation, to bind Large RNA/mRNA/ccfRNA on solid phase binding materials by differential solid phase binding, and to isolate Large RNA/mRNA/ccfRNA by centrifugation of the lysate of specimens in 1×DAP Solution containing 25-35% alcohol or 32% alcohol binding on solid phase binding materials.

The separation protocols include the steps to separate Small RNA/miRNA/ccfmiRNA from other biomolecules by differential precipitation, and to isolate Small RNA/miRNA/ccfmiRNA by centrifugation of the crude lysate of specimens containing 50-70% alcohol or 60% alcohol but without removing protein, without binding on solid phase binding materials, or without other treatment to the lysate. In addition, the protocols includes the steps to separate Small RNA/miRNA/ccfmiRNA from other biomolecules and to bind Small RNA/miRNA/ccfmiRNA on solid phase binding materials by differential solid phase binding, and to isolate Small RNA/miRNA/ccfmiRNA by centrifugation of the crude lysate of specimens containing 50-70% alcohol or 60% alcohol binding on solid phase binding materials but without removing protein or without other treatment to the lysate.

The remove and separation protocols include the step to isolate ccfDNA, ccfRNA, and ccfmiRNA from plasma, serum or other biofluid in 0.4× lysis solution containing 50-70% alcohol or 60% alcohol by differential precipitation or differential solid phase binding but without precipitation of protein from plasma, serum or biofluid, or without phenol extraction of protein from plasma, serum or biofluid. The protocols prevent protein from precipitation in plasma or serum for effective isolation of ccfDNA, ccfRNA and ccfmiRNA without co-precipitation of protein when high concentration of ethanol is applied during isolation. The protocols remove inhibitors in plasma or serum from isolated ccfDNA, ccfRNA and ccfmiRNA by differential centrifugation.

The binding protocols include the step to bind DNA/ccfDNA, Large RNA/mRNA/ccfRNA, Small RNA/miRNA/ccfmiRNA, and carbohydrate by differential solid phase binding on solid phase binding materials including, but not limited to, Affinity column, magnetic beads, and Con-A column, and therefore isolate DNA/ccfDNA, Large RNA/mRNA/ccfRNA, Small RNA/miRNA/ccfmiRNA, and carbohydrate from specimens on automated equipment or instruments in an automated means with minimum manual involvement. In addition, the protocols includes the steps to isolate protein by differential precipitation with centrifugation of the crude lysate of specimens containing 80-95% of alcohol or 90% alcohol; the steps to isolate lipid by extraction with Trimethylene bromochloride; the steps to isolate carbohydrate by differential solid phase binding; and the steps to isolate and purify metabolite by desalting.

The alteration protocols include the step to alter the DNA for DNA methylation assay by converting and modifying DNA in 0.06×DAP Solution containing Sodium Bisulfite and Hydroquinone; the step to alter the DNA for DNA sequencing by fragmentation of DNA; or the step to alter the DNA or RNA for hybridization by labeling DNA or RNA.

The protocols herein are examples of the vast varieties of protocols for the products and kit from this invention. Additional protocols are presented previously or presenting in example section of this specification. More new protocols will be generated through continuously development of open module technology and by accepting and adopting the protocols from users of products or Kits of this invention.

Automated Preparation of Specimens and Biomolecules with Core Module, Plug-in Modules and Automated Instrument The Allauto Kit, Alliso Kit, Allzol Kit, and other Plug-in Kit derived from the core module and Plug-in modules in this invention can be applied for automated preparation of specimens and biomolecules. For examples, install the Allauto Kit, Alliso Kit, Allzol Kit, and other Plug-in Kit in one automated instrument together and employ the softwares and hardwares from automated instruments to control and coordinate the leading role and supporting roles of the Allauto Kit, Alliso Kit, Allzol Kit, and other Plug-in Kit. Therefore, the functions and applications of integrated protection, isolation and alteration of specimens and biomolecules, the functions and applications of versatile preparation of specimens, and the functions and applications of systems isolation of biomolecules are all integrated in one automated instrument. The automated instrument is equipped with adaptors for the components from the Allauto Kit, Alliso Kit, Allzol Kit, and other Plug-in Kit, and built in with softwares and hardwares for preparation of specimens and biomolecules. After installation of the Allauto Kit, Alliso Kit, Allzol Kit, and other Plug-in Kit in one automated instrument together, according to a simple instruction and program from operators, the automated instrument can automated and integratively protect, isolate and alter specimens and biomolecules; automated and versatilely prepare a vast variety of solid specimens, liquid specimens and other special specimens; and automated and systematically isolate systems biomolecules.

This invention is compatible and capable to isolate biomolecules in automated process with core module and Plug-in modules such as magnetic beads, and automation instruments. In validation of capability in automation function and application by this invention, commercial vender's magnetic beads and automated instrument (the MagNA Pure Compact System from Roche) are adopted as Plug-in modules for the core module. Use MagNA Pure reagent Kit as control. 1 ml of plasma from pregnant woman was combined with lysis solution from this invention and incubated for 1 min after mix thoroughly. Add 3 ml ethanol in plasma lysate and mix thoroughly with appropriate amount of magnetic beads according to the vendor instructions. Separate the magnetic beads and wash the beads twice with 1 ml of 75% ethanol. The ccfDNA/ccfRNA/ccfmiRNA mixture was eluted with 50 ul water. Use MagNA Pure reagent Kit as control. Total genetic marker and fetal specific genetic marker were measured in isolated biomolecules from plasma by digital PCR. Total Genomic equivalent copies are 1400-1500 GE/per ml. Fetal Genomic equivalent copies are 100-150 GE/ml. The ratio of Fetal Genomic equivalent copies to Total Genomic equivalent copies is 7-10%. The result is better or comparable to vendor's own lysis solution as shown in Example 11. The automation in isolation of biomolecules meets the need and requirement of many clinical applications, such as molecular diagnostics, systems diagnostics, systems pathology, and etc.

The Functions or Applications of the Products and Kit Derived from the Invention The Allzol Kit, Alliso Kit, and Allauto kit with other plug-in kits integrate three types of preparation of specimens (protection, isolation and alteration) and systems preparation of specimens (isolation of DNA/ccfDNA, mRNA/Large RNA/ccfRNA, miRNA/Small RNA/ccfmiRNA, Protein, Lipid, Carbohydrate, and metabolites simultaneously) into one Kit with different extensions of functions and applications of specimen preparation. The Allzol kit, Alliso Kit, and Allauto kit from the core module without or with plug-in modules as one kit can protect specimen and biomolecules; isolate systems biomolecules simultaneously; and alter the biomolecules. The comprehensive protocols of Allzol kit, Alliso Kit, and Allauto kit for Integrated Versatile and Systems Preparation of Specimens can also be used selectively or individually for a particular preparation of specimen. The Allzol kit, Alliso Kit, and Allauto kit from the core module without or with plug-in modules as one kit can prepare systems biomolecules (DNA/ccfDNA, Large RNA/mRNA/ccfRNA, Small RNA/miRNA/ccfmiRNA, Protein, Lipid, Carbohydrate, and metabolites) from all different specimens including, but not limited to, solid specimens (tissue, cultured cell, plant, bacteria, and etc.) and liquid specimens (serum/plasma, blood, biofluid, and etc.). The Allzol kit, Alliso Kit, and Allauto kit from the core module without or with plug-in modules as one kit can accept and adopt the emerging and custom plug-in modules for expanding the varieties or multiple functions and applications in preparation of specimens through open module technology.

The Allzol kit derived from the core module can perform multiple or a variety of functions and applications in preparation of specimens and biomolecules, which include, but not limited to, 1) Isolation of DNA/ccfDNA, Large RNA/mRNA/ccfRNA, Small RNA/miRNA/ccfmiRNA, and Protein simultaneously (from tissue, cultured cell, plant, bacteria, serum/plasma, blood, and biofluid); 2) Isolation of Large RNA/mRNA/ccfRNA (from cell lysate, serum/plasma and other liquid specimens) individually; 3) Isolation of Large RNA/mRNA/ccfRNA (from tissue, cultured cell, plant, bacteria or plasma/serum with DNA contamination or with problem of RNA degradation) individually; 4) Isolation of DNA/ccfDNA (from tissue, cultured cell, plant, bacteria, or serum/plasma) individually; 5) Isolation of Small RNA/miRNA/ccfmiRNA (from tissue, cultured cell, plant, bacteria, or serum/plasma) individually; 6) Isolation of Protein (from tissue, cultured cell, plant, bacteria, or serum/plasma) individually; 7) Isolation of ccfDNA/ccfRNA/ccfmiRNA mixture (from serum/plasma and other biofluid); 8) Isolation of ccfDNA/ccfmiRNA mixture with removal of PCR inhibitors (from serum/plasma and other biofluid); 9) Isolation of ccfmiRNA with removal of PCR inhibitors (from serum/plasma and other biofluid) individually; 10) Clean up and concentrating of DNA/ccfDNA, Large RNA/mRNA/ccfRNA or Small RNA/miRNA/ccfmiRNA (from PCR or other reactions, or diluted samples).

Alliso Kit or Allauto Kit is the Allzol Kit with addition of Plug-in Kit, solid phase binding materials of affinity column or magnetic beads respectively, which have expanded the functions of Allzol Kit. With addition of other plug-in kits, Allzol Kit, Alliso Kit and Allauto Kit can perform extra functions or applications in isolations and alterations of biomolecules on top of multiple functions or applications aforementioned. The extra functions include, but not limited to, 1) Isolation of DNA/ccfDNA, Large RNA/mRNA/ccfRNA, Small RNA/miRNA/ccfmiRNA, Protein, Lipid, Carbohydrate, and metabolites simultaneously (from tissue, cultured cell, plant, bacteria, serum/plasma, blood, and biofluid); 2) Automation in Isolation of DNA/ccfDNA, Large RNA/mRNA/ccfRNA, Small RNA/miRNA/ccfmiRNA, and Protein with magnetic beads and automated instrument (from tissue, cultured cell, plant, bacteria, serum/plasma, blood, and biofluid); 3) Isolation of lipids (from tissue, cultured cell, plant, bacteria, whole blood, serum/plasma and other biofluid); 4) Isolation of Carbohydrate (from tissue, cultured cell, plant, bacteria, whole blood, serum/plasma and other biofluid); 5) Recovery of DNA/ccfDNA, Large RNA/mRNA/ccfRNA, and Small RNA/miRNA/ccfmiRNA (from Agarose gel slices); 6) Isolation of DNA, Large RNA/mRNA, Small RNA/miRNA, and Protein from FFPE Tissue Sections; 7) Isolation of DNA, Large RNA/mRNA, Small RNA/miRNA, Protein, Lipid, Carbohydrate, and Metabolite Simultaneously from Plant tissue rich in polysaccharide and polyphenols; 8) Isolation of DNA, Large RNA/mRNA, Small RNA/miRNA, Protein, Lipid, Carbohydrate, and Metabolite Simultaneously from Bacteria; 9) Isolation of Plasmid DNA from Bacteria; 10) Isolation of Mitochondria DNA and Nucleic DNA from Cells and Tissues; 11) Removal of DNA from RNA/miRNA; 12) DNA Fragmentation; 13) DNA Methylation Analysis; 14) DNA Labeling; 15) RNA Labeling, and etc.

Technical Advantages and Benefits of the Invention

Users can start with Allzol Kit or Alliso Kit in functions or applications of protection, isolation and alteration for most specimens and biomolecules. With plug-in Kits and the other plug-in modules, the functions or applications of protection, isolation and alteration in Allzol Kit or Alliso Kit can be extend to all specimens and all biomolecules, which cover almost all the preparation of specimens and biomolecules in the biomedical fields. Users only need one core module/Allzol Kit, some specific plug-in solutions and the other plug-in modules with one set of standardized protocols to achieve the results of multiple conventional kits from different vendors with different protocols. The users can save herein because the cost for specific plug-in solutions and the other plug-in modules is much lower than a complete kit from vendors providing conventional kits or products. Different users can share their core module/Allzol Kit, share specific plug-in solutions and share the other plug-in modules with other users, from which users can save too. Manufacturers will have same benefits as users. Manufacturers only need to make one core module/Allzol Kit, some plug-in solutions and the other plug-in modules to cover all the functions or applications for preparation of specimens and biomolecules with much higher efficiency than manufacture of multiple conventional Kits. After all, social and economical resources were saved; users have consistent products with flexible sharing resources; and manufacturers produce consistent products with higher efficiency and less consumptions. The method and Kits are the simple, easy to use, efficient, effective, low cost, no toxic, safe, environment friendly, broad coverage, integrated and systems means for users to prepare specimens and biomolecules.

The emerging plug-in kits and custom plug-in kits are continuously developed, adapted and adopted to the core kits derived from the core modules through the open module technology. There will be more and more plug-in kits for the core kits. The emerging Plug-in kits include, but not limited to, collection plug-in kit for collecting specimens and biomolecules, preservation plug-in kit for preserving specimens and biomolecules, storage plug-in kit for storing specimens and biomolecules, process plug-in kit for processing specimens and biomolecules, banking plug-in kit for specimens and biomolecules banking, transportation plug-in kit for transporting specimens and biomolecules, distribution plug-in kit for distributing specimens and biomolecules, alteration plug-in kit for altering specimens and biomolecules, modification plug-in kit for modifying specimens and biomolecules, special applications plug-in kit for special applications of specimens and biomolecules, analysis plug-in kit for analysis of specimens and biomolecules, detection plug-in kit for detection of specimens and biomolecules, and other plug-in kit for specimens and biomolecules. However, the core kits are also under improvement, reinvention and creation. There will be new versions of the existing core kits or new creation of the core kits too through the open module technology.

The products and Kits derived from this invention can be applied to clinical usage, research usage, and other usages. Clinical applications include, but not limited to, 1) isolation of ccf DNA, ccfRNA, ccfmiRNA from plasma, serum, and biofluid, 2) isolation of DNA, large RNA/mRNA, Small RNA/miRNA from whole blood or bone marrow, 3) isolation of Virus DNA and virus RNA from plasma, serum and biofluid, 4) isolation of DNA, Large RNA/mRNA, Small RNA/miRNA from FFPE section, 5) isolation of DNA, large RNA/mRNA, Small RNA/miRNA from biopsy samples, 6) isolation of DNA, large RNA/mRNA, Small RNA/miRNA from buccal cell, and/or swabs samples, 7) isolation of DNA/ccfDNA, large RNA/mRNA/ccfRNA, Small RNA/miRNA/ccfmiRNA from urine or stool samples, 8) isolation of DNA/ccfDNA, large RNA/mRNA/ccfRNA, Small RNA/miRNA/ccfmiRNA from biofluid samples, 9) isolation of DNA, large RNA/mRNA, Small RNA/miRNA from microorganisms, bacteria, yeast, virus, or parasite samples, 10) isolation of DNA, large RNA/mRNA, Small RNA/miRNA from blood spots and blood cards, and 11) alteration of DNA for diagnostics in Epigenomics and DNA methylation. The methods and Kits aforementioned for clinical applications can also be applied for research usage and other usages including, but not limited to, systems biology, systems medicine, systems pathology and systems diagnostics. The research usage and other usage include aforementioned the functions and applications of the core module and Plug-in modules in preparation of specimens and biomolecules.

The product and kit derived from the core module without or with plug-in modules as one kit with one set of standardized protocols is compatible to different biomolecules prepared from different specimens, compatible to biomolecules in different status (in PCR reaction, in gel, contaminated samples, or diluted samples), compatible to biomolecules altered by different method (labeling, modification, conversion, fragmentation), and compatible to the means of preparation (manual or automation). Users can use one set of standardized and connected kits with one set of standardized and connected protocols to meet all needs in preparation of specimen and biomolecules, which are the ultimate goal of the Integrated Versatile and Systems Preparation of specimens from this invention.

This invention has the integrated technical advantages of 1) It protects histological structures and micromorphology and intactness of biomolecules in the original specimens by store the original specimens in lysis solution at 4° C. and protects the intactness of biomolecules in the lysate of specimens at 4° C. 2) It lyses of tissue, cell, exo some, plant, other solid specimen or liquid specimens. 3) It inhibits Rnase, Dnase, proteinase and other enzymes that degrade the biomolecules. 4) It separates Large RNA/mRNA/ccfRNA from DNA/ccfDNA and Small RNA/miRNA/ccfmiRNA by differential centrifugation of the crude lysate of specimens without removing protein, without phenol/chloroform extraction, without binding Large RNA/mRNA/ccfRNA, DNA/ccfDNA or Small RNA/miRNA/ccfmiRNA on solid phase binding materials, or without other treatment to the lysate; It separates DNA/ccfDNA from Small RNA/miRNA/ccfmiRNA by differential precipitation of the crude lysate of specimens containing 25-35% alcohol but without removing protein, without binding Large RNA/mRNA/ccfRNA, DNA/ccfDNA or Small RNA/miRNA/ccfmiRNA on solid phase binding materials, or without other treatment to the lysate; 5) It decontaminates Large RNA/mRNA/ccfRNA from contaminants by decontamination in the 1×DAP Solution; It separates Large RNA/mRNA/ccfRNA from DNA/ccfDNA by differential precipitation of lysate of specimens in the 1×DAP Solution containing 25-35% alcohol with or without binding on solid phase binding materials. 6) It differentially precipitates Large RNA/mRNA/ccfRNA, DNA/ccfDNA, Small RNA/miRNA/ccfmiRNA and protein. PLIS solution differentially precipitates Large RNA/mRNA/ccfRNA with presentation of 0% alcohol, differentially precipitates DNA/ccfDNA with presentation of 32% alcohol, differentially precipitates Small RNA/miRNA/ccfmiRNA with presentation of 60% alcohol, and differentially precipitates protein with presentation of 90% alcohol. It differentially precipitates DNA/ccfDNA and isolate DNA/ccfDNA by centrifugation of the crude lysate of specimens containing 25-35% alcohol but without removing protein, without binding on solid phase binding materials, or without other treatment to the lysate; It differentially precipitates Large RNA/mRNA/ccfRNA and isolate Large RNA/mRNA/ccfRNA by centrifugation of the lysate of specimens in 1×DAP Solution containing 25-35% alcohol without binding on solid phase binding materials; It differentially precipitates Small RNA/miRNA/ccfmiRNA and isolate Small RNA/miRNA/ccfmiRNA by centrifugation of the crude lysate of specimens containing 50-70% alcohol but without removing protein, without binding on solid phase binding materials, or without other treatment to the lysate. 7) It isolates ccfDNA, ccfRNA, and ccfmiRNA from plasma, serum or other biofluid in 0.4× lysis solution containing 60% ethanol without precipitation of protein from plasma, serum or biofluid, or without phenol extraction of protein from plasma, serum or biofluid. 8) It prevents protein from precipitation in plasma or serum for effective isolation of ccfDNA, ccfRNA and ccfmiRNA without co-precipitation of protein when high concentration of ethanol is applied during isolation; 9) it removes inhibitors in plasma or serum from isolated ccfDNA, ccfRNA and ccfmiRNA by differential centrifugation; 10) It binds DNA/ccfDNA, large RNA/mRNA/ccfRNA and Small RNA/miRNA/ccfmiRNA and Carbohydrate on solid phase binding materials including, but not limited to, Affinity column, magnetic beads, or Con-A column by differential solid phase binding, and therefore isolate DNA/ccfDNA, large RNA/mRNA/ccfRNA, Small RNA/miRNA/ccfmiRNA and Carbohydrate from specimens on automated equipment or instruments in an automated means with minimum manual involvement. 11) It purifys DNA/ccfDNA, Large RNA/mRNA/ccfRNA, and Small RNA/miRNA/ccfmiRNA by dissociation protein and other contaminant from DNA/ccfDNA, Large RNA/mRNA/ccfRNA, and Small RNA/miRNA/ccfmiRNA; 12) It alters the DNA/ccfDNA for DNA/ccfDNA methylation assay by dissociation protein and other contaminant from DNA during DNA conversion and by converting and modifying DNA/ccfDNA in 0.06×DAP Solution containing Sodium Bisulfite and Hydroquinone; it alters the DNA for Nextgen DNA sequencing by fragmentation of DNA; and it alters the DNA or RNA for hybridization by labeling DNA or RNA; 13) It enables isolation of DNA/ccfDNA, Large RNA/mRNA/ccfRNA, and Small RNA/miRNA/ccfmiRNA by means of automation on equipments or instruments.

The products and Kits derived from this invention benefit users on aspects of quality in isolated biomolecules, working efficiency, safety, economic and environment. 1) Obtaining prepared biomolecules with superior quality and ultra purity, e.g. RNA will not degrade even electrophoresis in DNA gel. 2) Working at room temperature, easy to use protocols, and fast turnaround time due to intrinsic inhibition activity in the core module, elimination of phenol/chloroform extraction and other unnecessary steps. 3) One Kit for all: One Stop shopping because of multiple functions or application of preparation by the core module with plug-in modules. 4) One Set of standardized protocols for functions or application of all preparation. 5) Sharing the core module with other plug-in modules due to the compatibility among the core module and plug-in modules held by different users. 6) Reduce cost to users due to the fact that sharing modules and possible eliminating solid phase binding materials for binding of DNA/ccfDNA, Large RNA/mRNA/ccfRNA, and Small RNA/miRNA/ccfmiRNA are optional. 7) Reduce cost to manufactures due to the fact that sharing modules and possible eliminating solid phase binding materials for binding of DNA/ccfDNA, Large RNA/mRNA/ccfRNA, and Small RNA/miRNA/ccfmiRNA are optional. 8) Reduce contamination to environment due to the fact that sharing modules and possible eliminating solid phase binding materials for binding of DNA/ccfDNA, Large RNA/mRNA/ccfRNA, and Small RNA/miRNA/ccfmiRNA are optional. 9) Safe and no toxic to users, manufacture and environment due to elimination of phenol, chloroform and other toxic organic reagents conventionally used in isolation of DNA/ccfDNA, Large RNA/mRNA/ccfRNA, and Small RNA/miRNA/ccfmiRNA; 10) Lead to a low-carbon and Green economy in preparation of DNA/ccfDNA, Large RNA/mRNA/ccfRNA, Small RNA/miRNA/ccfmiRNA, protein, lipid, carbohydrate and metabolite from specimens due to the advantages of high efficiency, high effectiveness and low demanding on natural or man-made resources possessed by the method and Kit derived from this invention for Integrated Versatile and Systems Preparation of samples.

EXAMPLES

Example 1

Solutions in Core Module for Integrated Versatile and Systems Preparation of Specimens Core Module contains two solutions, Lysis solution and decontamination solution. The lysis solutions enables a single solution to protect specimens and biomolecules, to lyse specimens, to inhibit endogenous Dnase, Rnase and proteinase, and to separate Large RNA/mRNA/ccfRNA from DNA/ccfDNA, Small RNA/miRNA/ccfmiRNA and protein. Therefore the lysis solution is abbreviated herein as PLIS solution. The PLIS solution has following major features or functions:

1. Protect specimens and biomolecules: The specimens can be protected in 1×PLIS solution at 4° C. for at least 10 days without micromorphology change of specimen and without degradation of biomolecules inside protected specimen. Biomolecules in the lysate of specimen can also be protected for later process.

2. Lyse specimen: human or animal cells and tissues, cultured cell, plant, whole blood, plasma, serum, exosome, other biofluid can be well lysed in 1×PLIS solution.

3. Inhibit endogenous degrading enzymes such as Dnase, Rnase, proteinase, lipase, and carbohydase, and thus prepare specimens at room temperature: All isolation processes can be conducted at room temperature (around 25° C.), no ice or cool room needed because 1×PLIS has superior capability of inhibition on Dnase, Rnase, proteinase, lipase, and carbohydase. The RNA can be run in regular agarose gel for DNA in TAE buffer. No need run RNA in a denaturing formaldehyde gel for RNA which is toxic to user and environment.

4. Separate Large RNA/mRNA/ccfRNA, DNA/ccfDNA, Small RNA/miRNA/ccfmiRNA, protein and other biomolecules from each other: 1×PLIS solution will effectively separate Large RNA/mRNA/ccfRNA DNA/ccfDNA, Small RNA/miRNA/ccfmiRNA, protein and other biomolecules from each other by differential centrifugation and differential precipitation without toxic phenol/chloroform extraction and without expensive solid phase binding materials such as column or beads. It is safe and cost effective for user and friendly to environment.

The PLIS solution also has following features and functions including differential solid phase binding of DNA/ccfDNA, large RNA/mRNA/ccfRNA, Small RNA/miRNA/ccfmiRNA and Carbohydrate on solid phase binding materials; preventing protein from precipitation in plasma or serum for effective isolation of ccfDNA, ccfRNA and ccfmiRNA without co-precipitation of protein when high concentration of ethanol is applied during isolation; removing inhibitors in plasma or serum from isolated ccfDNA, ccfRNA and ccfmiRNA; purification of biomolecules; and enabling isolation of DNA/ccfDNA, Large RNA/mRNA/ccfRNA, and Small RNA/miRNA/ccfmiRNA by means of automation on equipments or instruments.

Decontamination solution has the functions of decontamination of impurities and DNA from Large RNA/mRNA/ccfRNA, alteration of biomolecules, protection and purification of biomolecules by differential precipitation or differential solid phase binding to solid phase binding materials. Therefore the decontamination solution is abbreviated herein as DAP solution. The DAP solution has following major features or functions:

1. Decontaminate impurities and DNA from Large RNA/mRNA/ccfRNA: Depended on the types of specimens, there are some impurities contaminated in Large RNA/mRNA/ccfRNA after differential centrifugation in PLIS solution. Dissolving Large RNA/mRNA/ccfRNA in 1×DAP solution will separate the impurities from Large RNA/mRNA/ccfRNA. Following with further centrifugation will remove impurities from Large RNA/mRNA/ccfRNA. To remove DNA from Large RNA/mRNA/ccfRNA, adding alcohol in 1×DAP solution containing Large RNA/mRNA/ccfRNA to 30% and performing differential precipitation to recover Large RNA/mRNA/ccfRNA in precipitation and remove DNA in the supernatant.

2. Alter biomolecules: For example, DAP solution separates the impurities, such as proteins, from DNA and facilitate the alteration of DNA in completed DNA conversion for methylation analysis. The DAP solution protects the DNA in DNA conversion and enhance the performance for DNA methylation assay. DAP solution also inactivates and removes modifying reagents and enzymes from the reactions of DNA fragmentation, DNA labeling, RNA labeling and etc. for their downstream applications.

3. Protection and purification of biomolecules: DAP solution inactivates degrading enzymes such as Dnase, Rnase, proteinase, lipase, and carbohydase. Thus it protects the biomolecules. With presenting of correct types and concentration of other chemicals, such as alcohol and salt, DAP purifies the biomolecules through differential precipitation and differential solid phase binding.

Example 2

Solutions, Materials and Instruments as Plug-in Modules for Integrated Systems Specimens Preparation

TABLE 7

Solutions, Materials and Instrument as Plug-in modules

| Plug-in Product | Volume | Application |
| --- | --- | --- |
| Affinity Column | 100 | Nucleic acid binding |
| Inhibitor Eliminator Stock Solution | 20 ml | Eliminate inhibitor |
| Wash Stock Solution | 12 ml | Wash column |
| Magnetic Beads | N/A | Automation |
| Instruments | N/A | Automation |
| Lipid Extractor | 60 ml | Lipid extraction |
| 2× Carb binder | 10 ml | Carbohydrate binding |
| Carb AffiColumn | 100 | Carbohydrate binding |
| Carb Eluter | 5 ml | Carbohydrate eluting |
| Desalt Column | 100 | Metabolites Desalting |
| Release Buffer | 18 ml | FFPE Section |
| 20× Release Enhancer | 850 ul | FFPE Section |
| 20× DNA Eliminator | 850 ul | FFPE, DNA remover |
| 1000× DNA Mincer | 10 ul | DNA Fragmentation |
| 20× Mincer Buffer | 1000 ul | DNA Fragmentation |
| Conversion Reagent | 5 g | Methylation Assay |
| Conversion enhancer | 10 ml | Methylation Assay |
| 5 × MN (Mitochondria and Nuclei Isolation Solution | 22 ml | Mito and Nu DNA |
| 2× PP Remover | 20 ml | Plant |
| 20× Lysozyme | 1100 ul | Bacteria |
| S1 Solution | 14 ml | Plasmid DNA |
| S2 Solution | 14 ml | Plasmid DNA |
| S3 Solution | 19 ml | Plasmid DNA |
| 20× DNA Eliminator | 850 ul | DNA remover |
| 20× DNA labeling Mix | 220 ul | DNA Labeling |
| 20× RNA labeling Mix | 220 ul | RNA Labeling |

Example 3

Protection of Specimen and Biomolecules

1. Protect the morphology in original specimens: The specimens, such as a piece of tissue sample, can be protected in 1×PLIS solution at 4° C. for at least 10 days without micromorphology change of specimen. The specimen should be sliced into 5 mm in thickness for the optimum results. For morphology application, take out specimen from 1×PLIS solution, soak in PBS for one hour with two changes of PBS, and specimen is ready for frozen tissue sectioning or for processing of formalin fixed and paraffin embedded (FFPE) tissue sectioning.

2. Protect the biomolecules in original specimens: The specimens, such as a piece of tissue sample, can be protected in 1×PLIS solution at 4° C. for at least 10 days without degradation of biomolecules inside specimen. For isolation of biomolecules, specimen either can be used directly in the 1×PLIS solution for protecting the specimen, or can be taken out from 1×PLIS solution during protection or transferred to a fresh 1×PLIS solution. Both can be directly used for isolation of intact biomolecules, such as DNA/ccfDNA, Large RNA/mRNA/ccfRNA, SmallRNA/miRNA/ccfmiRNA, protein, lipid, carbohydrate and metabolite.

3. Protect integrity of biomolecules in the lysate of specimen for later process: The lysate of specimen, such as tissue or cell lydate, or plasma/serum lysate, in 1×PLIS can be protected at 4° C. for at least 10 days without degradation of biochemocals in the lysate of specimens. They can be directly used for isolation of intact biomolecules, such as DNA/ccfDNA, Large RNA/mRNA/ccfRNA, SmallRNA/miRNA/ccfmiRNA, protein, lipid, carbohydrate and metabolite.

Example 4

Lysis of Specimens

Animal tissue and plant tissue require some mechanical force to homogenize the tissue in 1×PLIS to lyse the cell inside the tissue. There are five major methods to homogenize the tissue:

1. Homogenizer with generator probe. This is the most powerful tools for homogenizing large piece of tissue, such as Omni TH—Tissue Homogenizer;
2. Beads method: This method can deal with specimen in small volume (0.3 ml), such as Precellys 24 Bead Mill Homogenizer;
3. Dounce tissue grinder: inexpensive alternative with manual process, provided by Sigma, VWR and Thermo;
4. Tissue Pulverizer: see Cole-Parmer; and
5. Ultrasonic processing: use with caution because it can mechanically break down DNA and RNA.

When homogenizing tissue or plant with mechanical force, follow the instruction of instrument and avoid over homogenization. Once tissue is homogenized into fine particle, it should stop. It may require some optimization on tissue homogenization to get better isolations of biomolecules.

Under homogenization cause lower yield and cross contamination of biomolecules. Over homogenization cause break down of biomolecules and cross contamination also.

Whole blood and plasma/serum can be directly lysed in 2×PLIS solution without need of mechanical force. When whole blood, cell, bacteria, serum, or plasma were lysed with 1×PLIS solution, please invert lysate back and forth until lysate was homogenized; pipetting lysate up and down with gentle in less than 5 times if lysate cannot be homogenized by inverting mix.

Cultured cell can be directly lysed in 1×PLIS solution without need of mechanical force. Wash cell with or without PBS before adding 1×PLIS solution. Spread 1×PLIS solution evenly to all cells and scrape sticky cell lysate to corner of the flask or plate. Transfer cell lysate into tubes, avoid harsh pipetting, and invert to mix cell lysate.

For specimen containing bacteria, pre-treatment with lysozyme is necessary for complete lysis of bacteria by 1×PLIS.

Amount of Specimens and Lysis solution as listed in Table 8 and Table 9:
1. Use 400 ul of 1×PLIS solution for 10-30 mg solid specimens such tissue, cells, homogenize if it is tissue sample.
2. Use 200 ul of 2×PLIS solution for 200 ul of liquid specimens such as serum/plasma, biofluids samples.
3. Use 200 ul of 1×PLIS solution to lyse the cell in 96 well plate due to the volume per well is about 350 ul. In following isolation procedure, please use half amount of ethanol for precipitation or binding of DNA/ccfDNA or Small RNA/miRNA/ccfmiRNA, for examples, in Step 6 or Step 12 of EXAMPLE 5.
4. When users provide their own lysozyme, please use 200 ul of 50 mM Tris, 10 mM EDTA, pH 8.0 containing 1 mg/ml lysozyme to resuspend bacteria pellet instead of H2O.
5. Some homogenization methods require a large volume and waste some lysate after homogenization. The volume of lysis solution can be scale up to make sure there will be 400 ul of lysate left for isolation later.

TABLE 8

Amount of Solid Specimen and 1 × PLIS lysis Solution

| Solid Specimen | Specimen amount | 1 × PLIS ul | Lysate ul for Isolation |
|---|---|---|---|
| Cultured Cell attached | T25 flask (3 × 10e6 cell) | 400 | 400 |
| Cultured Cell attached | T75 flask (1 × 10e7 cell) | 1000 | 400 |
| Cultured Cell attached | 1-4 × 10e6 cell | 400 | 400 |
| Cultured Cell attached | 96 well (4 × 10e5 cell) | 200 | 200 |
| Cultured Cell attached | 5000 cell | 200 | 200 |
| Animal Tissue | 1 mg | 400 | 400 |
| Animal Tissue | 10 mg | 400 | 400 |
| Animal Tissue | 30 mg | 1200 | 400 |
| Plant tissue | 40 mg | 400 | 400 |
| Plant tissue | 100 mg | 1000 | 400 |

TABLE 9

Amount of Liquid Specimen and 2 × PLIS lysis Solution

| Liquid Specimen | Liquid Specimen Volume (ul) | H2O (ul) | ul of 20× lysozyme | 2 × PLIS Solution Volume (ul) |
|---|---|---|---|---|
| Serum | 200 | | | 200 |
| Plasma | 200 | | | 200 |
| Biofluid | 200 | | | 200 |
| Whole blood | 50 | 150 | | 200 |
| Biofluid/Cell or parasite | 200 | | | 200 |
| Biofluid/Bacteria | 190 | | 10 | 200 |
| Culture cell in suspension | 200 | | | 200 |
| Culture cell pellet | from 200-1000 ul | 200, Mix first | | 200 |
| Bacterial in suspension | 190 | | 10 | 200 |
| Bacterial pellet | from 400 ul | 190, Mix first | 10 | 200 |
| Watery/cell or parasites | 200 | | | 200 |
| Watery/Bacteria | 190 | | 10 | 200 |
| PCR reaction | 200 | | | 200 |
| Enzymatic reaction | 200 | | | 200 |
| Sequencing reaction | 200 | | | 200 |
| Labeling reaction | 200 | | | 200 |
| Chemical modified samples | 200 | | | 200 |
| Contaminated samples | 200 | | | 200 |
| Diluted samples | 200 | | | 200 |

Example 5

Isolation of DNA/ccfDNA, Large RNA/mRNA/ccfRNA, Small RNA/miRNA/ccfmiRNA, Protein, Lipid, Carbohydrate, and Metabolites Simultaneously (from Tissue, Cultured Cell, Plant, Bacteria, Serum/Plasma, Blood, and Biofluid)

Continue from EXAMPLE 4 Lysis of Specimens: 1. Transfer 400 ul of lysate into corresponding centrifuge tube as indicated in above chart, and leave at room temperature for 2-5 min.
2. Isolate Large RNA/mRNA/ccfRNA: centrifuge the tube with lysate at 13000 RPM (16000 g RCF) in micro-centrifuge or 16000 g in a large centrifuge for 5 min at room temperature to separate Large RNA/mRNA/ccfRNA from DNA/ccfDNA and Small RNA/miRNA/ccfmiRNA.
3. Pour out supernatant (about 390 ul) in step 2 into a fresh micro-centrifuge tube for isolation of DNA/ccfDNA and Small RNA/miRNA/ccfmiRNA later, remove supernatant as much as possible to minimize the DNA/ccfDNA contamination in Large RNA/mRNA/ccfRNA.
4. Save pellet for isolation Large RNA/mRNA/ccfRNA, pellet may not be visible or see a white pellet with size as 0.1 ul to 10 ul.
5. Add 300 ul of 1×DPA solution into micro-centrifuge tube containing Large RNA/mRNA/ccfRNA pellet in step 4, vortex for 10 second to dislodge the pellet from bottom of tube and leave at room temperature, vortex periodically during following process until the pellet is completely dissolved.
6. Add 180 ul of 100% (or 95% denatured) ethanol to supernatant containing DNA/ccfDNA and Small RNA/miRNA/ccfmiRNA poured out from step 3.
7. Mix ethanol and supernatant from Step 6 thoroughly by inverting tube back and forth for 20 times and leave at room temperature for 2 min, DNA/ccfDNA will form visible precipitation if large amount DNA/ccfDNA is presented.

8. While waiting, vortex micro-centrifuge tube containing pellet for Large RNA/mRNA/ccfRNA in step 5 for 5 second to break up the pellet and leave at room temperature.
9. Isolate DNA/ccfDNA: centrifuge mixture of ethanol and supernatant in step 7 at 13000 RPM (16000 g RCF) for 5 min at room temperature to pellet DNA/ccfDNA.
10. Pour out supernatant from Step 9 into a fresh micro-centrifuge tube for isolation of Small RNA/miRNA/ccfmiRNA, remove supernatant as much as possible to minimize the Small RNA/miRNA/ccfmiRNA contamination in DNA/ccfDNA.
11. Save pellet for isolation of DNA/ccfDNA later, DNA/ccfDNA pellet may not be visible. It may be seen as a white pellet with size as 0.1 ul to 5 ul or spread evenly over the slope area of the micro-centrifuge tube at the side toward centrifuging force.
12. Add 430 ul of 100% (or 95% denatured) ethanol to supernatant containing Small RNA/miRNA/ccfmiRNA poured out from step 10.
13. Mix ethanol and supernatant from Step 12 thoroughly by inverting tube back and forth for 20 times and leave at room temperature for 2 min to precipitate Small RNA/miRNA/ccfmiRNA.
14. While waiting, vortex micro-centrifuge tube containing pellet for Large RNA/mRNA/ccfRNA in step 5 for 5 second to break up the pellet and leave at room temperature.
15. Isolate Small RNA/miRNA/ccfmiRNA: centrifuge mixture of ethanol and supernatant in step 13 at 13000 RPM (16000 g RCF) for 5 min at room temperature to pellet Small RNA/miRNA/ccfmiRNA.
16. Pour out supernatant from Step 15 into a fresh micro-centrifuge tube for isolation of protein, remove supernatant as much as possible to minimize the protein contamination in Small RNA/miRNA/ccfmiRNA.
17. Save pellet for isolation of Small RNA/miRNA/ccfmiRNA later. Small RNA/miRNA/ccfmiRNA pellet may not be visible. It may be seen as a white strip or spread evenly over the slope area of the micro-centrifuge tube at the side toward centrifuging force.
18. Isolate Protein: Take 200 ul of supernatant containing protein poured out from Step 16 and add 600 ul of 100% (or 95% denatured) ethanol to the supernatant containing protein.
19. Mix ethanol and supernatant from Step 18 thoroughly by inverting tube back and forth for 20 times and leave at room temperature for 2 min to a few hours to precipitate protein.
20. While waiting, vortex micro-centrifuge tube containing pellet for Large RNA/mRNA/ccfRNA in step 5 for 5 second to dissolve the pellet completely.
21. Centrifuge the dissolved pellet containing Large RNA/mRNA/ccfRNA from Step 20 at 13000 RPM (16000 g RCF) for 2 min at room temperature to remove insoluble contaminants from mRNA/Larger RNA/ccfRNA.
22. Pour out supernatant from Step 21 into a fresh micro-centrifuge tube for isolation of Large RNA/mRNA/ccfRNA, do not touch the pellet containing contaminants.
23. Add 135 ul of 100% (or 95% denatured) ethanol to supernatant containing Large RNA/mRNA/ccfRNA poured out from Step 22. Adding 450 ul of 100% (or 95% denatured) ethanol to supernatant if isolate ccfRNA from Plasma, Serum or biofluids.
24. Mix ethanol and supernatant from Step 23 thoroughly by inverting tube back and forth for 20 times and leave at room temperature for 2 min to precipitate Large RNA/mRNA/ccfRNA.
25. While waiting, check protein precipitation from Step 19. If protein form large amount of precipitation, it is ready to isolate protein and to go to Step 27. Otherwise, wait until the precipitation forms.
26. When protein precipitation forms, go to Steps from 27 to 34. Store at −20° C. to promote protein precipitation if it did not form precipitation at Step 25. Isolate protein later by going to Step 27 to 34 when precipitation of protein forms.
27. Isolate Large RNA/mRNA/ccfRNA and Protein: centrifuge mixture of ethanol and supernatant containing Large RNA/mRNA/ccfRNA from Step 24 and mixture containing Protein at Step 19 (when large amount of protein precipitation forms) at 13000 RPM (16000 g RCF) for 5 min at room temperature to pellet Large RNA/mRNA/ccfRNA and Protein.
28. Pour out and discard supernatant of Large RNA/mRNA/ccfRNA from Step 27. Pour out and save supernatant of Protein from Step 27 for isolation of lipids, carbohydrates and metabolites later. Save pellets of Large RNA/mRNA/ccfRNA and Protein for next step.
29. Wash pellets of DNA/ccfDNA in Step 11, Small RNA/miRNA/ccfmiRNA in Step 17, Large RNA/mRNA/ccfRNA in Step 28 and Protein in Step 28 by adding 1 ml of 75% ethanol and inverting the tube back and forth for 20 times.
30. Centrifuge the washed pellet of DNA/ccfDNA, Small RNA/miRNA/ccfmiRNA, Large RNA/mRNA/ccfRNA and Protein from Step 29 at 13000 RPM (16000 g RCF) for 1 min at room temperature.
31. Pour out and discard supernatant of all tubes from Step 30, add 0.5 ml of 75% ethanol and inverting the tube back and forth for 20 times.
32. Centrifuge the washed pellet of DNA/ccfDNA, Small RNA/miRNA/ccfmiRNA, Large RNA/mRNA/ccfRNA and Protein from Step 31 at 13000 RPM (16000 g RCF) for 1 min at room temperature.
33. Pour out and discard supernatant of all tubes from Step 32, invert tube on paper towel with lid open to drain out last bit of washing solution with slightly knocking the tube on the paper towel.
34. Stand up the tubes from Step 33 with lid open at room temperature or 37° C. for 10-30 min to evaporate residual ethanol and dry out the pellets.
35. Add 30-100 ul of Dnase and Rnase free H20 to dissolve the pellets of DNA/ccfDNA, Small RNA/miRNA/ccfmiRNA, Large RNA/mRNA/ccfRNA as indicated in Table 10. Add 10-200 ul of 1% SDS to dissolve the pellet of protein as indicated in Table 10.

TABLE 10

Biomolecules to be Isolated and volume to be reconstituted

| Specimen | DNA H20 ul | ccf DNA H20 ul | Large RNA H20 ul | ccf RNA H20 ul | Small RNA H20 ul | ccf miRNA H20 ul | Protein 1% SDS ul |
|---|---|---|---|---|---|---|---|
| Cultured Cell attached | 100 | | 100 | | 100 | | 20 |
| Cultured Cell (96 well plate) | 30 | | 30 | | 30 | | 10 |
| Animal Tissue | 100 | | 100 | | 100 | | 20 |
| Plant tissue | 50 | | 50 | | 50 | | 10 |
| Serum | | 30 | | 30 | | 30 | 200 |
| Plasma | | 30 | | 30 | | 30 | 200 |
| Biofluid | | 30 | | 30 | | 30 | 10 |
| Whole blood | 30 | | 30 | | 30 | | 50 |
| Biofluid/Cell or parasite | 30 | | 30 | | 30 | | 10 |

TABLE 10-continued

Biomolecules to be Isolated and volume to be reconstituted

| Specimen | DNA H20 ul | ccf DNA H20 ul | Large RNA H20 ul | ccf RNA H20 ul | Small RNA H20 ul | ccf miRNA H20 ul | Protein 1% SDS ul |
|---|---|---|---|---|---|---|---|
| Biofluid/Bacteria | | 30 | | 30 | | 30 | 10 |
| Culture cell in suspension | 30 | | 30 | | 30 | | 10 |
| Culture cell pellet | 30 | | 30 | | 30 | | 10 |
| Bacterial in suspension | 30 | | 30 | | 30 | | 10 |
| Bacterial pellet | 50 | | 50 | | 50 | | 10 |
| Watery/cell or parasites | 30 | | 30 | | 30 | | 10 |
| Watery/Bacteria | | 30 | | 30 | | 30 | 10 |

36. Measure the concentration of DNA/ccfDNA, Small RNA/miRNA/ccfmiRNA, Large RNA/mRNA/ccfRNA with NanoDrop or other UV spectrophotometer at 260/280 nm. 1 OD reading at 260 nm represents DNA concentration at 50 ug/ml or represents RNA concentration at 40 ug/ml. Expecting OD ratio for DNA and large RNA/mRNA: 260/280 nm, 1.8-2.0; 260/230 nm, around 2; 260/270 nm, around 1.2; 260/250 nm, around 1.1; 330 nm, no reading. The OD ratio for ccfDNA, ccfRNA, Small RNA/miRNA/ccfmiRNA, Virus DNA and virus RNA can be varied depended on the source of specimens.

37. The yields of DNA/ccfDNA, Small RNA/miRNA/ccfmiRNA, Large RNA/mRNA/ccfRNA are varied depended on the type and quality of Specimen. Following Table 11 provides a reference for the typical yield expected.

TABLE 11

Yields of Biomolecules to be expected (ng/ul)

| Specimen | DNA | ccf DNA | Large RNA | ccf RNA | Small RNA | ccf miRNA | Protein |
|---|---|---|---|---|---|---|---|
| Cultured Cell attached | 250 | | 270 | | 65 | | 2000 |
| Cultured Cell (96 well plate) | 15 | | 23 | | 8 | | 2000 |
| Liver Tissue | 90 | | 350 | | 50 | | 5000 |
| Plant tissue | 70 | | 500 | | 20 | | 2000 |
| Human Normal Serum | | 6 | | 17 | | 0.8 | 5000 |
| Human Normal Plasma | | 6 | | 17 | | 0.8 | 5000 |
| Human Whole blood | 15 | | 1 | | 6 | | 5000 |
| Bacterial pellet | 200 | | 750 | | 110 | | 2000 |

38. Agarose gel electrophoresis to check the quality and purity of isolated biomolecules. DNA, Large RNA/mRNA and Small RNA/miRNA can be run in regular agaros gel for DNA in TAE buffer as shown in Panel A of FIG. 11. Large RNA/mRNA is not degraded as confirmed in RNA gel as shown in Panel C of FIG. 11. It is not necessary to run Large RNA/mRNA and Small RNA/miRNA isolated by this invention in a denaturing RNA gel containing formaldehyde which is toxic to user and environment because Rnase has been inhibited and removed effectively by 1×PLIS solution and/or DAP solution.

39. Some Specimens have very lower yield of DNA, ccfDNA, virus DNA, Large RNA, ccfRNA, virus RNA, Small RNA, ccfmiRNA which cannot be accurately measured by NanoDrop or UV spectrophotometer.

PCR or RT-PCR can be used to determine the success of isolations. ccfDNA, ccfRNA and ccfmiRNA are ready for use or stored at −70° C. for later use. Use 4 ul of ccfDNA, ccfRNA or ccfmiRNA for each PCR or RT-PCR reaction in 25 ul. FIGS. 12, 13 and 14 shown the PCR and RT-PCR data from ccfDNA, ccfRNA and ccfmiRNA 40. The concentration and intactness of protein can be determined by SDS-PAGE (Polyacrylamide Gel Electrophoresis) as shown in Panel D of FIG. 11. Following Table 12 provides a reference for PAGE. Protein concentration may also be measure by different methods which can avoid the influence of detergent introduced when solving the protein pellet.

TABLE 12

Amount of Biomolecules to be reconstituted and Analyzed in PAGE

| Specimen | ul of 1% SDS for reconstituting Protein | ul used in PAGE | Amount of Specimen used in PAGE |
|---|---|---|---|
| Cultured Cell attached | 20 | 10 | 2 × 10e5 cell |
| Cultured Cell (96 well plate) | 10 | 10 | 4 × 10e4 cell |
| Liver Tissue | 20 | 10 | 1 mg tissue |
| Plant Leaf | 10 | 10 | 8 mg tissue |
| Human Normal Serum | 200 | 10 | 2 ul Serum |
| Human Normal Plasma | 200 | 10 | 2 ul Plasma |
| Human Normal Whole blood | 50 | 10 | 2 ul whole blood |
| Bacterial pellet | 10 | 10 | 80 ul culture |

41. Isolate Lipids: add 2.4 ml of Trimethylene bromochloride to the saved supernatant of Protein about 800 ul from Step 28 for isolation of lipids, carbohydrates and metabolites.

42. Mix Trimethylene bromochloride and supernatant from Step 41 thoroughly by inverting tube back and forth for 20 times and leave at room temperature for 1 min to separate lipids from carbohydrates and metabolites.

43. Centrifuge mixture of Trimethylene bromochloride and supernatant in step 42 at 13000 RPM (16000 g RCF) for 5 min at room temperature to separate lipids from carbohydrates and metabolites.

44. Take out aqueous phase at top about 80 ul from Step 43 into a fresh micro-centrifuge tube and save it for isolation of carbohydrates and metabolites later. Remove aqueous phase as much as possible to minimize the carbohydrates and metabolites contamination in Lipids.

45. Drying of organic phase at bottom and resuspended in 10 ul of Trimethylene bromochloride.

46. Isolate Carbohydrate: add 80 ul of 2× Carb binder to the saved aqueous phase about 80 ul from Step 44 for isolation of carbohydrates.

47. Mix 2× Carb binder and saved aqueous phase from Step 46 thoroughly by inverting tube back and forth for 20 times and transfer 160 ul of aqueous phase in 1× Carb binder to Carb AffiColumn.

48. Centrifuge the Carb AffiColumn at 13000 RPM (16000 g RCF) for 1 min at room temperature to separate carbohydrates from metabolites. Carbohydrates bind to column and metabolites stay in flow through.

49. Save flow through for isolation of metabolites later

50. Add 50 ul of Carb Eluter to Carb AffiColumn in Step 48, and centrifuge the Carb AffiColumn at 13000 RPM (16000 g RCF) for 1 min at room temperature to elute carbohydrates from Carb AffiColumn in step 48.

51. Isolate metabolites: metabolites from flow through in step 49 are ready for application. Desalt from metabolites can be applied if necessary.

52. Load 160 ul of flow through in step 49 into desalt column. Continuously elute with water or different elution buffer compatible to the metabolites.
53. Continuously collect the eluate and isolate the metabolites.

Example 6

Isolation of DNA/ccfDNA, Large RNA/mRNA/ccfRNA, Small RNA/miRNA/ccfmiRNA, Protein, Lipid, Carbohydrate, and Metabolites Simultaneously with Affinity Micro-Column (from Tissue, Cultured Cell, Plant, Bacteria, Serum/Plasma, Blood, and Biofluid)

Continue from EXAMPLE 4 Lysis of Specimens for isolation of biomolecules with affinity micro-column. 1. Transfer 300 ul of lysate into corresponding centrifuge tube as indicated in above chart, and leave at room temperature for 2-5 min.
2. Isolate Large RNA/mRNA/ccfRNA: centrifuge the tube with lysate at 13000 RPM (16000 g RCF) in micro-centrifuge or 16000 g in a large centrifuge for 5 min at room temperature.
3. Pour out supernatant (about 290 ul) in step 2 into a fresh micro-centrifuge tube for isolation of DNA/ccfDNA and Small RNA/miRNA/ccfmiRNA later, remove supernatant as much as possible to minimize the DNA/ccfDNA contamination in Large RNA/mRNA/ccfRNA.
4. Save pellet for isolation of Large RNA/mRNA/ccfRNA, pellet may not be visible or see a white pellet with size as 0.1 ul to 10 ul.
5. Add 300 ul of 1×DAP solution into micro-centrifuge tube containing Large RNA/mRNA/ccfRNA pellet in step 4, vortex for 10 second to dislodge the pellet from bottom of tube and leave at room temperature, vortex periodically during following process until the pellet is completely dissolved.
6. Add 190 ul of 100% (or 95% denatured) ethanol (40%) to supernatant containing DNA/ccfDNA and Small RNA/miRNA/ccfmiRNA poured out from step 3.
7. Mix ethanol and supernatant from Step 6 thoroughly by inverting tube back and forth for 20 times and leave at room temperature for 2 min, DNA/ccfDNA will form visible precipitation if large amount DNA/ccfDNA is presented.
8. While waiting, vortex micro-centrifuge tube containing pellet for Large RNA/mRNA/ccfRNA in step 5 for 5 second to break up the pellet and leave at room temperature.
9. Isolate DNA/ccfDNA: Transfer the mixture of ethanol and supernatant in step 7 into Affinity micro-column/collection tube and centrifuge at 13000 RPM (16000 g RCF) for 1 min at room temperature to bind DNA/ccfDNA to solid phase. Small RNA/miRNA/ccfmiRNA in flow through was collected in collection tube.
10. Take out Affinity micro-column containing DNA/ccfDNA from collection tube in Step 9 and temporarily put into a fresh micro-centrifuge tube, and add 235 ul of 100% ethanol (60%) into collection tube containing flow through for isolation of Small RNA/miRNA/ccfmiRNA.
11. Mix well and leave at room temperature for 2 min.
12. While waiting, vortex micro-centrifuge tube containing pellet for Large RNA/mRNA/ccfRNA in step 5 for 5 second to solve the pellet completely and leave at room temperature.
13. Isolate Small RNA/miRNA/ccfmiRNA: Transfer mixture of ethanol and lysate from collecting tube in step 11 to a fresh Affinity micro-column with collecting tube, centrifuge at 13000 RPM for 1 min at room temperature to bind Small RNA/miRNA/ccfmiRNA to solid phase. Protein in flow through was collected in collection tube.
14. Take out Affinity micro-column containing DNA/ccfDNA from micro-centrifuge tube in Step 10 and put it back into the empty collection tube in Step 13. Leave it aside for DNA/ccfDNA isolation later.
15. Take out Affinity micro-column containing Small RNA/miRNA/ccfmiRNA from collection tube in Step 13 and temporarily put into a fresh micro-centrifuge tube; Collect flow through containing protein from collection tube in step 13 and transfer into a fresh 1.5 ml micro-centrifuge tube. Leave it aside for protein isolation later.
16. Take out Affinity micro-column Small RNA/miRNA/ccfmiRNA from micro-centrifuge tube in Step 15 and put it back into the empty collection tube in Step 15. Leave it aside for Small RNA/miRNA/ccfmiRNA isolation later.
17. Vortex micro-centrifuge tube containing pellet for Large RNA/mRNA/ccfRNA in step 5 for 5 second to solve the pellet completely, centrifuge at 13000 RPM for 2 min at room temperature to remove insoluble materials.
18. Pour supernatant containing Large RNA/mRNA/ccfRNA in step 17 out into a fresh 1.5 ml micro-centrifuge tube.
19. Total supernatant from step 18 is about 300 ul, add 135 ul of 100% (or 95% denatured) ethanol (31%) into supernatant in step 18 for Large RNA/mRNA isolation from cell or tissue, or add 450 ul of 100% (or 95% denatured) ethanol (60%) into supernatant in step 18 for ccfRNA isolation from plasma or serum.
20. Mix well and leave at room temperature for 2 min.
21. Isolate Protein: While waiting, transfer 200 ul of protein lysate from step 15 into a fresh micro-centrifuge tube, add 600 ul of 100% (or 95% denatured) ethanol (90%) (at three volume of protein lysate) into the tube, mix well and leave at room temperature for isolation of protein later.
22. Load 430 or 750 ul lysate from step 20 on Affinity micro-column with collecting tube, centrifuge at 13000 RPM for 1 min at room temperature.
23. Optional: Collect flow through from step 22 into a fresh 1.5 ml micro-centrifuge tube for protein isolation if necessary.
24. The Affinity micro-column containing Large RNA/mRNA/ccfRNA with collecting tube is ready for further process.
25. Add 500 ul of IE (Inhibitor Eliminating) buffer into Affinity micro-column containing DNA/ccfDNA in step 14, into Affinity micro-column containing Small RNA/miRNA/ccfmiRNA in Step 16, and into Affinity micro-column containing Large RNA/mRNA/ccfRNA in Step 24.
26. Centrifuge the Affinity micro-columns with collecting tube in step 25 at 13000 RPM in a micro-centrifuge for 0.5 min at room temperature, discard flow through.
27. Add 500 ul of wash buffer into the Affinity micro-columns with collecting tube in step 26.
28. Centrifuge the Affinity micro-columns with collecting tube in step 27 at 13000 RPM in a micro-centrifuge for 0.5 min at room temperature, discard flow through.
29. Open the lid of the Affinity micro-columns in Step 28, centrifuge the Affinity micro-columns with collecting tube at 13000 RPM in a micro-centrifuge for 3 min at room temperature.
30. Mark and label the fresh, Dnase and Rnase free, 1.5 ml micro-centrifuge tubes for collecting DNA/ccfDNA, Large RNA/mRNA/ccfRNA, Small RNA/miRNA/ccfmiRNA.
31. Transfer Affinity micro-columns from step 29 to the marked fresh tubes in step 30, discard collection tubes in step 29.
32. Add 30-100 ul of DEPC (diethyl pyrocarbonate) H20 into each column, leave at room temperature for 2-10 min.

33. Centrifuge the Affinity micro-columns with collecting tube in step 32 at 13000 RPM in a micro-centrifuge for 1 min at room temperature to elute DNA/ccfDNA, Large RNA/mRNA/ccfRNA, and Small RNA/miRNA/ccfmiRNA into collecting tubes.

34. Measure the concentration of DNA/ccfDNA, Small RNA/miRNA/ccfmiRNA, Large RNA/mRNA/ccfRNA with Nano-Drop or other UV spectrophotometer at 260/280 nm. 1 OD reading at 260 nm represents DNA concentration at 50 ug/ml or represents RNA concentration at 40 ug/ml. Expecting OD ratio for DNA and Large RNA/mRNA: 260/280 nm, 1.8-2.0; 260/230 nm, around 2; 260/270 nm, around 1.2; 260/250 nm, around 1.1; 330 nm, no reading. The OD ratio for ccfDNA, ccfRNA and Small RNA/miRNA/ccfmiRNA, Virus DNA and virus RNA can be varied depended on the source of specimens.

35. The yields of DNA/ccfDNA, Small RNA/miRNA/ccfmiRNA, Large RNA/mRNA/ccfRNA are varied depended on the type and quality of BioSpecimen. See yield Table 11 as aforementioned in EXAMPLE 5.

36. Protein in Step 21 should form precipitation in 15 min at room temperature. If not, leave at room temperature for hours or store at −80° C. overnight.

37. Centrifuge the protein precipitate at 13000 RPM in a micro-centrifuge for 2 min at room temperature. Pour out supernatant in a fresh tube and save supernatant for isolation of lipids, carbohydrates and metabolites later.

38. Add 75% of ethanol 1 ml to wash the protein pellet in step 37, leave at room temperature for 1 min.

39. Centrifuge the protein precipitate in Step 38 at 13000 RPM in a micro-centrifuge for 1 min at room temperature, discard supernatant.

40. Discard supernatant in step 39; add 75% of ethanol 1 ml to wash the protein pellet in step 39, leave at room temperature for 1 min.

41. Centrifuge the protein precipitate in Step 40 at 13000 RPM in a micro-centrifuge for 1 min at room temperature, discard supernatant.

42. Invert tube on paper towel with lid open to drain out last bit of washing solution with slightly knocking the tube on the paper towel.

43. Stand up the tubes from Step 42 with lid open at room temperature or 37° C. for 10-30 min to evaporate residual ethanol and dry out the pellets.

44. Add 10-200 ul of 1% SDS to dissolve the protein pellet in Step 43.

45. If protein pellet is not soluble, vortex for 30 second, heat at 95-100° C. for 10 min, vortex 10 second three times during heating.

46. Agarose gel electrophoresis to check the quality and purity of isolated Biomolecules. DNA, Large RNA/mRNA and Small RNA/miRNA can be run in regular agarose gel for DNA in TAE buffer as shown in Panel B of FIG. 11. No need run RNA in a formaldehyde gel which is toxic to user and environment because Rnase has been inhibited effectively by 1×PLIS solution.

47. Some BioSpecimens have very lower yield of DNA, ccfDNA, virus DNA, Large RNA, ccfRNA, virus RNA, Small RNA, ccfmiRNA which cannot be accurately measured by NanoDrop or UV spectrophotometer.
PCR or RT-PCR can be used to determine the success of isolations. ccfDNA, ccfRNA and ccfmiRNA are ready for use or stored at −70° C. for later use. Use 4 ul of ccfDNA, ccfRNA or ccfmiRNA for each PCR or RT-PCR reaction in 25 ul.

48. The protein concentration and integrity can be determined by SDS-PAGE as shown in Panel D of FIG. 11. The Table 12 in EXAMPLE 5 provides a reference for PAGE.

Protein concentration may also be measured by different methods which can avoid the influence of detergent introduced when solving the protein pellet.

49. Isolate Lipids: add 2.4 ml of Trimethylene bromochloride to the saved supernatant of Protein about 800 ul from Step 37 for isolation of lipids, carbohydrates and metabolites.

50. Mix Trimethylene bromochloride and supernatant from Step 37 thoroughly by inverting tube back and forth for 20 times and leave at room temperature for 1 min to separate lipids from carbohydrates and metabolites.

51. Centrifuge mixture of Trimethylene bromochloride and supernatant in step 50 at 13000 RPM (16000 g RCF) for 5 min at room temperature to separate lipids from carbohydrates and metabolites.

52. Take out aqueous phase at top about 80 ul from Step 51 into a fresh micro-centrifuge tube and save it for isolation of carbohydrates and metabolites later. Remove aqueous phase as much as possible to minimize the carbohydrates and metabolites contamination in Lipids.

53. Drying of organic phase at bottom and resuspended in 10 ul of Lipid Extractor.

54. Isolate Carbohydrate: add 80 ul of 2× Carb binder to the saved aqueous phase about 80 ul from Step 52 for isolation of carbohydrates.

55. Mix 2× Carb binder and saved aqueous phase from Step 52 thoroughly by inverting tube back and forth for 20 times and transfer 160 ul of aqueous phase in 1× Carb binder to Carb AffiColumn.

56. Centrifuge the Carb AffiColumn at 13000 RPM (16000 g RCF) for 1 min at room temperature to separate carbohydrates from metabolites. Carbohydrates bind to column and metabolites stay in flow through.

57. Save flow through for isolation of metabolites later

58. Add 50 ul of Carb Eluter to Carb AffiColumn in Step 56, and centrifuge the Carb AffiColumn at 13000 RPM (16000 g RCF) for 1 min at room temperature to elute carbohydrates from Carb AffiColumn in step 56.

59. Isolate metabolites: metabolites from flow through in step 57 are ready for application. Desalt from metabolites can be applied if necessary.

60. Load 160 ul of flow through in step 57 into desalt column. Continuously elute with water or different elution buffer compatible to the metabolites.

61. Continuously collect the eluate and isolate the metabolites.

Example 7

Isolation of ccfDNA/ccfRNA/ccfmiRNA Mixture (from Serum/Plasma and Other Biofluid)

Continue from EXAMPLE 4 Lysis of Specimens—1. Transfer 400 ul of lysate into corresponding centrifuge tube or the volume as indicated in above chart, and leave at room temperature for 2-5 min.

2. Add 600 ul of 100% (or 95% denatured) ethanol to the lysate.

3. Mix ethanol and supernatant thoroughly by inverting tube back and forth for 20 times and leave at room temperature for 2 min. no formation of precipitation.

4. Centrifuge mixture of ethanol and supernatant at 13000 RPM (16000 g RCF) for 5 min at room temperature in microcentrifuge or 16000 g in a large centrifuge.

5. Pour out and discard supernatant and wash pellet of ccfDNA/ccfRNA/ccfmiRNA by adding 1 ml of 75% ethanol and inverting the tube back and forth for 20 times.

6. Centrifuge the washed pellet of ccfDNA/ccfRNA/ccfmiRNA at 13000 RPM (16000 g RCF) for 1 min at room temperature.
7. Pour out and discard supernatant, add 0.5 ml of 75% ethanol and inverting the tube back and forth for 20 times.
8. Centrifuge the washed pellet of ccfDNA/ccfRNA/ccfmiRNA at 13000 RPM (16000 g RCF) for 1 min at room temperature.
9. Pour out and discard supernatant, invert tube on paper towel with lid open to drain out last bit of washing solution with slightly knocking the tube on the paper towel.
10. Stand up the tubes with lid open at room temperature or 37° C. for 10-30 min to evaporate residual ethanol and dry out the pellets.
11. Add 30 ul of Dnase and Rnase free H2O to dissolve the pellets of ccfDNA/ccfRNA/ccfmiRNA.
12. Go to step 36 in EXAMPLE 5 Isolation of DNA/ccfDNA, Large RNA/mRNA/ccfRNA, Small RNA/miRNA/ccfmiRNA, Protein, Lipids, carbohydrates, and metabolite simultaneously (from cultured cell, tissue, plant, bacteria, serum/plasma, blood, and biofluid).

Example 8

Isolation of ccfDNA/ccfmiRNA Mixture with Removal of PCR Inhibitors (from Serum/Plasma and Other Biofluid)

Continue from EXAMPLE 4 Lysis of Specimens: 1. Transfer 400 ul of lysate into corresponding centrifuge tube or the volume as indicated in above chart, and leave at room temperature for 2-5 min.
2. Centrifuge the tube with lysate at 13000 RPM (16000 g RCF) in micro-centrifuge or 16000 g in a large centrifuge for 5 min at room temperature.
3. Pour Supernatant to a fresh tube and add 600 ul of 100% (or 95% denatured) ethanol to supernatant containing ccfDNA/ccfmiRNA.
4. Mix ethanol and supernatant thoroughly by inverting tube back and forth for 20 times and leave at room temperature for 2 min.
5. Centrifuge mixture of ethanol and supernatant at 13000 RPM (16000 g RCF) for 5 min at room temperature in micro-centrifuge or 16000 g in a large centrifuge.
6. Pour out and discard supernatant and wash pellet of ccfDNA/ccfmiRNA by adding 1 ml of 75% ethanol and inverting the tube back and forth for 20 times.
7. Centrifuge the washed pellet of ccfDNA/ccfmiRNA at 13000 RPM (16000 g RCF) for 1 min at room temperature.
8. Pour out and discard supernatant, add 0.5 ml of 75% ethanol and inverting the tube back and forth for 20 times.
9. Centrifuge the washed pellet of ccfDNA/ccfmiRNA at 13000 RPM (16000 g RCF) for 1 min at room temperature.
10. Pour out and discard supernatant, invert tube on paper towel with lid open to drain out last bit of washing solution with slightly knocking the tube on the paper towel.
11. Stand up the tubes with lid open at room temperature or 37° C. for 10-30 min to evaporate residual ethanol and dry out the pellets.
12. Add 30 ul of Dnase and Rnase free H2O to dissolve the pellets of ccfDNA/ccfmiRNA.
13. Go to step 36 in EXAMPLE 5 Isolation of DNA/ccfDNA, Large RNA/mRNA/ccfRNA, Small RNA/miRNA/ccfmiRNA, Protein, Lipids, carbohydrates, and metabolite Simultaneously (from cultured cell, tissue, plant, bacteria, serum/plasma, blood, and biofluid).

Example 9

Clean Up and Concentrating of DNA/ccfDNA, Large RNA/mRNA/ccfRNA or Small RNA/miRNA/ccfmiRNA (from PCR or Other Reactions, or Diluted Samples)

Continue from EXAMPLE 4 Lysis of Specimens: 1. Transfer 400 ul of lysate into corresponding centrifuge tube or the volume as indicated in above chart, and leave at room temperature for 2-5 min.
2. Add 600 ul of 100% (or 95% denatured) ethanol to the lysate.
3. Mix ethanol and supernatant thoroughly by inverting tube back and forth for 20 times and leave at room temperature for 2 min.
4. Centrifuge mixture of ethanol and supernatant at 13000 RPM (16000 g RCF) for 5 min at room temperature in micro-centrifuge or 16000 g in a large centrifuge.
5. Pour out and discard supernatant and wash pellet of DNA/ccfDNA, Large RNA/mRNA/ccfRNA or Small RNA/miRNA/ccfmiRNA by adding 1 ml of 75% ethanol and inverting the tube back and forth for 20 times.
6. Centrifuge the washed pellet of DNA/ccfDNA, Large RNA/mRNA/ccfRNA or Small RNA/miRNA/ccfmiRNA at 13000 RPM (16000 g RCF) for 1 min at room temperature.
7. Pour out and discard supernatant, add 0.5 ml of 75% ethanol and inverting the tube back and forth for 20 times.
8. Centrifuge the washed pellet of DNA/ccfDNA, Large RNA/mRNA/ccfRNA or Small RNA/miRNA/ccfmiRNA at 13000 RPM (16000 g RCF) for 1 min at room temperature.
9. Pour out and discard supernatant, invert tube on paper towel with lid open to drain out last bit of washing solution with slightly knocking the tube on the paper towel.
10. Stand up the tubes with lid open at room temperature or 37° C. for 10-30 min to evaporate residual ethanol and dry out the pellets.
11. Add 30 ul of Dnase and Rnase free H2O to dissolve the pellets of DNA/ccfDNA, Large RNA/mRNA/ccfRNA or Small RNA/miRNA/ccfmiRNA.
12. Measure the concentration of DNA/ccfDNA, Small RNA/miRNA/ccfmiRNA, Large RNA/mRNA/ccfRNA with Nano-Drop or other UV spectrophotometer at 260/280 nm. 1 OD reading at 260 nm represents DNA concentration at 50 ug/ml or represents RNA concentration at 40 ug/ml. Expecting OD ratio for DNA and large RNA/mRNA: 260/280 nm, 1.8-2.0; 260/230 nm, around 2; 260/270 nm, around 1.2; 260/250 nm, around 1.1; 330 nm, no reading. The OD ratio for ccfDNA, ccfRNA, Small RNA/miRNA/ccfmiRNA, Virus DNA and virus RNA can be varied depended on the source of specimens.
13. DNA/ccfDNA, Small RNA/miRNA/ccfmiRNA, Large RNA/mRNA/ccfRNA are ready for further application.

Example 10

Recovery of DNA/ccfDNA, Large RNA/mRNA/ccfRNA or Small RNA/miRNA/ccfmiRNA (from Agarose Gel Slices)

1. Run DNA/ccfDNA, Large RNA/mRNA/ccfRNA, or Small RNA/miRNA/ccfmiRNA in Agarose gel at 1-3%.
2. Stain gel in DNA/RNA staining dye, such as EB (Ethidium Bromide) or other dyes.

3. Weight a micro-centrifuge tube on the balance and mark the weight on tube.
4. Under UV light, ware eye and face protector, cut out gel slice containing the DNA/ccfDNA, Large RNA/mRNA/ccfRNA, or Small RNA/miRNA/ccfmiRNA of interest.
5. Transfer the gel slice into the pre-weighted tube and weight it again. The weight of gel slice is total weight of tube and gel slice subtracting the weight of tube.
6. Add the 1.5×DAP solution at three times weight of gel slice in mg into the tube containing gel slice, for example, if gel slice weight is 200 mg, add 600 ul of 1.5×DAP solution.
7. Incubate the tube in 65° C. for 10 minutes and invert mix the tube a few times during incubation.
8. Cool down the tube in room temperature and add ethanol at 2.67 times weight of gel slice in mg into the tube containing gel slice, for example, if gel slice weight is 200 mg, add 533 ul of ethanol.
9. Mix thoroughly and leave at room temperature for 2 minute.
10. Centrifuge the micro-centrifuge tube at 13000 RPM for 5 minute at room temperature.
11. Pour out and discard supernatant, wash the pellet of DNA/ccfDNA, Large RNA/mRNA/ccfRNA, or Small RNA/miRNA/ccfmiRNA by adding 1 ml of 75% ethanol and inverting the tube back and forth for 20 times.
12. Centrifuge the washed pellet of DNA/ccfDNA, Large RNA/mRNA/ccfRNA, or Small RNA/miRNA/ccfmiRNA at 13000 RPM (16000 g RCF) for 1 min at room temperature.
13. Pour out and discard supernatant, add 0.5 ml of 75% ethanol and inverting the tube back and forth for 20 times.
14. Centrifuge the washed pellet of DNA/ccfDNA, Large RNA/mRNA/ccfRNA, or Small RNA/miRNA/ccfmiRNA at 13000 RPM (16000 g RCF) for 1 min at room temperature.
15. Pour out and discard supernatant, invert tube on paper towel with lid open to drain out last bit of washing solution with slightly knocking the tube on the paper towel.
16. Stand up the tubes with lid open at room temperature or 37° C. for 10-30 min to evaporate residual ethanol and dry out the pellets.
17. Add 30 ul of Dnase and Rnase free H2O to dissolve the pellets of DNA/ccfDNA, Large RNA/mRNA/ccfRNA, or Small RNA/miRNA/ccfmiRNA.
18. Measure the concentration of DNA/ccfDNA, Large RNA/mRNA/ccfRNA, or Small RNA/miRNA/ccfmiRNA with NanoDrop or other UV spectrophotometer at 260/280 nm. 1 OD reading at 260 nm represents DNA concentration at 50 ug/ml or represents RNA concentration at 40 ug/ml.
Expecting OD ratio for DNA and large RNA/mRNA: 260/280 nm, 1.8-2.0; 260/230 nm, around 2; 260/270 nm, around 1.2; 260/250 nm, around 1.1; 330 nm, no reading. The OD ratio for ccfDNA, ccfRNA, or Small RNA/miRNA/ccfmiRNA can be varied depended on the source of specimens.
19. Run agarose gel to check the size and amount of recovered DNA/ccfDNA, Large RNA/mRNA/ccfRNA, or Small RNA/miRNA/ccfmiRNA as shown in FIG. 15. They are ready for next applications, such as subcloning, labeling or amplifications.

Example 11

Automation in Isolation of DNA/ccfDNA, Large RNA/mRNA/ccfRNA, Small RNA/miRNA/ccfmiRNA and Protein with Magnetic Beads and Automated Instrument (from Tissue, Cultured Cell, Plant, Bacteria, Serum/Plasma, Blood, and Biofluid)

This protocol requests magnetic beads and automated equipment or instrument as Plug-in modules for the automated Isolation of DNA/ccfDNA, Large RNA/mRNA/ccfRNA, SmallRNA/miRNA/ccfmiRNA. Use isolation of ccfDNA from plasma of pregnant woman as example herein. The instrument for automation is Roche MagNa Pure Compact. Apply either PLIS solution in core module or Roche MagNA Kit in Roche MagNa Pure Compact automated instrument for isolation of ccfDNA and Compare results. When using the Roche MagNA Kit, ccfDNA was isolated according to the instruction of the Roche MagNA Kit. When using PLIS solution in core module, following protocol was adopted in Roche MagNa Pure Compact automated instrument.
1. Add 200 ul or 1 ml of 2×PLIS solution in 1.5 ml tube or 5 ml tube.
2. Add 200 ul or 1 ml of plasma in the tubes.
3. Mix thoroughly by inverting the tubes back and forth for 20 times.
Or 3.1. Continue from EXAMPLES 4 Lysis of Specimens. Start with 400 ul or 2 ml of cell or tissue lysate in 1×PLIS solution in 1.5 ml tube or 5 ml tube.
4. Add 600 ul ethanol or 3 ml ethanol to the sample and mix.
5. Add appropriate amount of magnetic beads according to the instructions.
6. Incubate for 1 minute at room temperature.
7. Separation the magnetic beads and wash the beads twice with 1 ml of 75% ethanol.
8. Elute with 10 or 50 ul of H20.
9. Testing by Digital PCR with total genomic DNA marker and fetal specific genetic marker.
10. Average result from the plasma of pregnant women. Total Genomic equivalent copies: 1400-1500 GE/per ml. Fetal Genomic equivalent copies: 100-150 GE/ml. Ratio of Fetal GE to Total GE: 7-10% of Total GE.
11. Comparison of PLIS solution in core module with Roche MagNA Kit in Roche MagNa Pure Compact automated instrument for automated isolation of ccfDNA. PLIS solution in core module performs well in Roche MagNa Pure Compact automated instrument for automated isolation of ccfDNA. The result from PLIS solution in core module is similar to the result from Roche MagNA Kit as shown in Table 13. The automation in isolation of biomolecules meets the need and requirement of many clinical applications, such as molecular diagnostics, systems diagnostics, systems pathology, and etc.

TABLE 13

Comparison of PLIS solution in Core Module with Roche MagNA Kit in Automated Isolation of ccfDNA

|  | Fetal_ccfDNA (GE/mL) | Total_ccfDNA (GE/mL) | Fetal ccfDNA Percentage) |
|---|---|---|---|
| Core Module | 157 | 1439 | 10.9% |
| Roche MagNA Kit | 145 | 1356 | 10.7% |
| Core Module/Roche | 107.5% | 106.1% | 101.9% |

Example 12

Isolation of DNA, RNA, miRNA and Protein from FFPE Tissue Sections

This protocol requests FFPE Release Solution, 20× Release Enhancer, and 20×DNA Eliminator as Plug-in modules for isolation of DNA, RNA, miRNA and Protein from FFPE Tissue Sections. Turn on two water bath or heat blocks, one is set at 55° C. or 65° C., the other one is set at 86° C. before start.

Process 1: Tissue section preparation: 1. Tissue in Formalin Fixed and Paraffin Embedded (FFPE) block should be 0.5× 0.5 cm2 to 2×2 cm2.
2. Cut Formalin Fixed and Paraffin Embedded (FFPE) tissue section at 5 um thick.
3. Use one tissue section per preparation DNA, RNA/miRNA for most tissues, if the yield of DNA or RNA/miRNA was low in certain tissue, two or three tissue section can be used.
4. FFPE Tissue section can be attached on glass slide as routine tissue section from pathological lab, or FFPE Tissue section can be rolled up during sectioning and transfer rolled tissue section directly into micro-centrifuge tube with forceps.

Process 2: Isolate DNA or RNA without removing paraffin from tissue section
1. Tissue section in micro-centrifuge tube can be applied to release process without removing paraffin.
2. Use blade to scrape tissue section from glass slide and transfer tissue section into micro-centrifuge tube for release of biomolecules from tissue section without removing paraffin.
3. Go to Process 4. Lysis of Tissue section Or Process 3 (preferred): Remove Paraffin from tissue section on glass slide or in micro-centrifuge tube. A. Tissue section on glass slide, 1. Immerse tissue section on glass slide into Xylene in tissue section processing tank for 1 minutes, move the slide up and down 10 times.
2. Immerse tissue section on glass slide into 100% ethanol in tissue section processing tank for 1 minutes, move the slide up and down 10 times.
3. Immerse tissue section on glass slide into H20 in tissue section processing tank for 1 minutes, move the slide up and down 10 times.
4. Take out the slide from H2O and use blade to scrape the tissue section off from glass slide, do not let tissue section dry.
5. Transfer scraped tissue section from glass slide to a 1.5 ml micro-centrifuge tube. The tissue section is ready for protease digestion.

B: Tissue section in micro-centrifuge tube
1. Add 1 ml xylene into the micro-centrifuge tube containing tissue section, incubate at room temperature for 1 min with inverting the tubes for 20 times.
2) Centrifuge the micro-centrifuge tube containing tissue section at 13000 RPM for 2 min at room temperature, the tissue section should stick at bottom of tube, pour off the supernatant only.
3) Add 1 ml ethanol into the micro-centrifuge tube containing tissue section, and incubate at room temperature for 1 min with inverting the tubes for 20 times.
4) Centrifuge the micro-centrifuge tube containing tissue section at 13000 RPM for 2 min at room temperature, the tissue section should stick at bottom of tube, pour off the supernatant only.
5) Dry at 86° C. to evaporate ethanol, 2-3 min, tissue section from wet white become dry white. The tissue section is ready for protease digestion.

Process 4: Release of biomolecules from tissue section
1. Add 152 ul FFPE Release Solution into micro-centrifuge tube containing one tissue section.
2. Add 8 ul of 20× Release Enhancer to the micro-centrifuge tube containing the tissue section and mix completely.
3. Use lock for micro-centrifuge cap to prevent opening the tube during heat incubation later.
4. Incubate tissue section at 65° C. for 30 min if paraffin was not removed from tissue section.
5. Incubate tissue section at 55° C. for 15 min if paraffin was removed from tissue section.
6. Mix the digestion solution a few times by flick the bottom of micro-centrifuge tube during incubation at 2 min, 5 min and 15 min.
7. As general role, tissue section should start to diminish around 2 minute, it should be completely disappear at 15 minute of digestion. There may be some undigested tissue section residue left for some type of tissues.
8. Incubate tissue section with protease at 86° C. for 15 min, do not Mix the digestion solution by flick the bottom of micro-centrifuge tube if the paraffin was not removed from tissue section at beginning.
9. Cool down the micro-centrifuge tube with tissue section. Leave in ice for five minute if the paraffin was not removed from tissue section at beginning.
10. Centrifuge the micro-centrifuge tube at 13000 RPM for 2 min at room temperature.
11. Transfer clear supernatant to a fresh micro-centrifuge tube. There will be a thin layer of paraffin on top of supernatant and on side of micro-centrifuge tube if the paraffin was not removed from tissue section at beginning. Do not transfer paraffin.
12. The clear supernatant can be used as DNA or RNA from FFPE tissue section for PCR or other applications with low demand at this stage, or go to next stage for isolation and purification.

Process 5: Isolation of FFPE DNA (DNA, RNA and miRNA mixture)
1. Add 320 ul of 1.5×DAP solution to the supernatant in Process 4, Step 12, and mix completely.
2. Add 720 ul of 100% ethanol to the mixture and mix completely.
3. Centrifuge the micro-centrifuge tube at 13000 RPM for 5 min at room temperature.
4. Pour out and discard supernatant and wash pellet of FFPE DNA by adding 1 ml of 75% ethanol and inverting the tube back and forth for 20 times.
5. Centrifuge the washed pellet of FFPE DNA at 13000 RPM (16000 g RCF) for 1 min at room temperature. 6. Pour out and discard supernatant, add 0.5 ml of 75% ethanol and inverting the tube back and forth for 20 times.
7. Centrifuge the washed pellet of FFPE DNA at 13000 RPM (16000 g RCF) for 1 min at room temperature. 8. Pour out and discard supernatant, invert tube on paper towel with lid open to drain out last bit of washing solution with slightly knocking the tube on the paper towel.
9. Stand up the tubes with lid open at room temperature or 37° C. for 10-30 min to evaporate residual ethanol and dry out the pellets.
10. Add 30 ul of Dnase and Rnase free H2O to dissolve the pellets of FFPE DNA.
11. Measure the concentration of FFPE DNA with NanoDrop or other UV spectrophotometer at 260/280 nm. 1 OD reading at 260 nm represents DNA concentration at 50 ug/ml or represents RNA concentration at 40 ug/ml.
12. Expecting ratio for FFPE DNA is varied depending on yield and types of tissue section, ideally should be 260/280 nm, 1.8-2.0; 260/230 nm, around 2; 260/270 nm, around 1.2; 260/250 nm, around 1.1; 330 nm, no reading.
13. The ratio falls in outside the ideal range will not affect the performance in QPCR or QRT-PCR reaction.
14. The FFPE DNA is ready for next applications. Use 50 ng of FFPE DNA in each PCR or QPCR reaction with 25 ul of reaction volume.

Process 6: Isolation of FFPE RNA/miRNA: 1. Add 8 ul of 20×DNA Eliminator into the supernatant at Process 4, Step 12, and mix completely. 2. Incubate at room temperature for 15 minutes. 3. Add 320 ul of 1.5×DAP solution to the supernatant and mix completely.
4. Add 720 ul of 100% ethanol to the mixture and mix completely.
5. Centrifuge the micro-centrifuge tube at 13000 RPM for 5 min at room temperature.
6. Pour out and discard supernatant and wash pellet of FFPE RNA/miRNA by adding 1 ml of 75% ethanol and inverting the tube back and forth for 20 times.
7. Centrifuge the washed pellet of FFPE RNA/miRNA at 13000 RPM (16000 g RCF) for 1 min at room temperature.
8. Pour out and discard supernatant, add 0.5 ml of 75% ethanol and inverting the tube back and forth for 20 times.
9. Centrifuge the washed pellet of FFPE RNA/miRNA at 13000 RPM (16000 g RCF) for 1 min at room temperature.
10. Pour out and discard supernatant, invert tube on paper towel with lid open to drain out last bit of washing solution with slightly knocking the tube on the paper towel.
11. Stand up the tubes with lid open at room temperature or 37° C. for 10-30 min to evaporate residual ethanol and dry out the pellets.
12. Add 30 ul of Dnase and Rnase free H2O to dissolve the pellets of FFPE RNA/miRNA.
13. Measure the concentration of FFPE RNA/miRNA with NanoDrop or other UV spectrophotometer at 260/280 nm. 1 OD reading at 260 nm represents DNA concentration at 50 ug/ml or represents RNA concentration at 40 ug/ml.
14. Expecting ratio for FFPE RNA/miRNA is varied depending on yield and types of tissue section, ideally should be 260/280 nm, 1.8-2.0; 260/230 nm, around 2; 260/270 nm, around 1.2; 260/250 nm, around 1.1; 330 nm, no reading.
15. The ratio falls in outside the ideal range will not affect the performance in QPCR or QRT-PCR reaction.
16. The FFPE RNA/miRNA is ready for next applications. Use 50 ng of FFPE RNA/miRNA in each RT-PCR or QRT-PCR reaction with 25 ul of reaction volume.

Process 7: The yield of FFPE DNA and RNA/miRNA: 1. The yields of DNA and RNA/miRNA are varied depended on the type and quality of tissue section. Following Table 14 provides a reference for the typical yield expected. Estimation of tissue weight: for a tissue section area around 10 mm×10 mm at 0.005 mm thick, the estimated weight of tissue is 10×10×0.005=0.5 mg.

TABLE 14

Expected yield of FFPE DNA/RNA/miRNA:

| | DNA | RNA/miRNA |
|---|---|---|
| Normal Tissue (ug/mg tissue) | 1 ug | 1 ug |
| Tumor Tissue: (ug/mg tissue) | 2-4 ug | 3-6 ug |

2. The yield of DNA in above table did not contain RNA/miRNA. The DNA/RNA/miRNA mixture consists of DNA and RNAmiRNA at about 1:1 ratio. 3. The FFPE DNA or FFPE RNA/miRNA is ready for next applications. Use 50 ng of FFPE DNA or FFPE RNA/miRNA in each PCR, QPCR, RT-PCR or QRT-PCR reaction with 25 ul of reaction volume.

Process 8: Isolation of protein from FFPE tissue section (for both Allzol and Alliso Kit)
1. Add 160 ul of FFPE Release Solution into micro-centrifuge tube containing one tissue section with or without removal of paraffin.
2. Heat the micro-centrifuge tube with FFPE lysate at 98° C. for 15 min and heat at 86° C. for 2 hours with agitation periodically.
3. Centrifuge the micro-centrifuge tube with FFPE lysate at 13300 RPM (16300 g RCF) for 1 min at room temperature in a micro-centrifuge.
4. Transfer the supernatant into a fresh micro-centrifuge tube and extracted protein in the supernatant is ready for quantification, PAGE or Western blotting assay.

Process 9: Testing of isolated FFPE DNA, RNA and miRNA: 1. Agarose gel electrophoresis to check the quality and purity of isolated Biomolecules. As shown in FIG. 16, FFPE DNA/RNA/miRNA or RNA/miRNA can be run in regular 3% agaros gel for DNA in TAE buffer.
2. Testing on function and application of isolated DNA, RNA/miRNA from FFPE tissue section: Quantitative PCR (QPCR) for DNA or Quantitative Real Time PCR (QRT-PCR) for RNA/miRNA is the appropriate methods for testing of FFPE DNA or FFPE RNA/miRNA as shown in FIGS. 17, 18, and 19. Amounts of FFPE DNA or RNA/miRNA to use in QPCR or QRT-PCR are 50 ng of DNA or RNA/miRNA in 25 ul of reaction volume.

Example 13

Isolation of DNA, Large RNA/mRNA, Small RNA/miRNA, Protein, Lipid, Carbohydrate, and Metabolite Simultaneously from Plant Tissue Rich in Polysaccharide and Polyphenols This protocol requests 2×PP Remover as Plug-in module for removal of polysaccharide and polyphenols and isolation of DNA, Large RNA/mRNA, Small RNA/miRNA, Protein, carbohydrate, lipid and metabolite from plant tissue rich in polysaccharide and polyphenols.
1. Prepare lysis solution of 1×PLIS Solution and 1×PP Remover by mixing 2×PLIS solution and 2×PP Remover thoroughly at 1:1 ratio. Use 400 ul of final lysis solution for each isolation.
2. Transfer 400 ul of lysis solution of 1×PLIS Solution and 1×PP Remover to the container for homogenization. Beads method, Dounce tissue grinder or motor-probe can be used for homogenize the plant tissue. Some homogenization methods require a large volume and waste some lysate. The volume of lysis solution can be scale up to make sure there will be 400 ul of lysate left for isolation later.
3. Mince 40 mg plant tissue into small pieces around 1 mm×1 mm and transfer into container with lysis solution. Scale up tissue amount if lysis solution is scaled up.
4. Homogenize the plant tissue according to the instruction of instrument or experiences. Once tissue is homogenized into fine particle, it should stop. Under homogenization cause lower yield and cross contamination of biomolecules. Over homogenization cause break down of biochemocals and cross contamination also. It may require some optimization on tissue homogenization to get better isolations of biomolecules.
5. Go to step 1 in EXAMPLE 5 Isolation of DNA/ccfDNA, Large RNA/mRNA/ccfRNA, Small RNA/miRNA/ccfmiRNA, Protein, Lipids, carbohydrates, and metabolite Simultaneously (from tissue, cultured cell, plant, bacteria, serum/plasma, blood, and biofluid)

Example 14

Isolation of DNA, Large RNA/mRNA, Small RNA/miRNA, Protein, Lipid, Carbohydrate, and Metabolite Simultaneously from Bacteria This protocol requests 20× Lysozyme as Plug-in module for lysis of bacteria and isolation of DNA, Large RNA/mRNA, Small RNA/miRNA Protein, carbohydrate, lipid and metabolite from bacteria.

1. Transfer 0.4 ml over night bacteria culture into 1.5 ml micro-centrifuge tube (Eppendorf tube).
2. Centrifuge micro-centrifuge tube containing bacteria at 6000 RPM (3300 g RCF) for 5 minute at room temperature in a micro-centrifuge.
3. Pour out and discard supernatant, add 190 ul purified water to bacteria pellet, vortex to resuspend bacteria pellet.
4. Add 10 ul of 20× lysozyme to resuspend bacteria and mix thoroughly by inverting tube back and forth for 20 times. Incubate at room temperature for 15-30 min.
5. Add 200 ul of 2×PLIS solution to the bacteria suspension and mix thoroughly by inverting tube back and forth for 20 times till the lysate become clear.
6. Go to step 1 in EXAMPLE 5 Isolation of DNA/ccfDNA, Large RNA/mRNA/ccfRNA, Small RNA/miRNA/ccfmiRNA, Protein, Lipids, carbohydrates, and metabolite Simultaneously (from tissue, cultured cell, plant, bacteria, serum/plasma, blood, and biofluid)

Example 15

Isolation of Plasmid DNA from Bacteria

This protocol requests S1, S2 and S3 solution as Plug-in modules for lysis of bacteria and isolation of plasmid DNA from bacteria.
1. Transfer 1 ml over night bacteria culture into 1.5 ml micro-centrifuge tube (Eppendorf tube).
2. Centrifuge micro-centrifuge tube containing bacteria at 6000 RPM (3300 g RCF) for 5 minute at room temperature in a micro-centrifuge.
3. Pour out and discard supernatant, add 125 ul S1 Solution to bacteria pellet, vortex to resuspend bacteria pellet.
4. Add 125 ul of S2 Solution to resuspended bacteria and mix thoroughly by inverting tube back and forth for 20 times till bacteria suspension become clear. No vortex.
5. Add 175 ul of S3 Solution to the clear bacteria suspension and mix thoroughly by inverting tube back and forth for 20 times till white precipitation forms.
6. Centrifuge precipitated bacteria suspension at 13300 RPM (16300 g RCF) for 5 minute at room temperature in a micro-centrifuge.
7. Pour out supernatant into a fresh 1.5 ml micro-centrifuge tube (Eppendorf tube).
8. Add 850 ul of 100% ethanol, mix thoroughly by inverting tube back and forth for 20 times or vortex for 5 second, and incubate at room temperature for 2 minutes.
9. Centrifuge the mixture of ethanol and supernatant at 13300 RPM (16300 g RCF) for 5 minute at room temperature in a micro-centrifuge.
10. Pour out and discard supernatant, add 1 ml of 75% ethanol to the pellet of plasmid DNA, wash the pellet by inverting tube back and forth for 20 times.
11. Centrifuge the washed pellet of plasmid DNA at 13300 RPM (16300 g RCF) for 1 minute at room temperature in a micro-centrifuge.
12. Pour out and discard supernatant, invert tube on paper towel with lid open to drain out last bit of washing solution with slightly knocking the tube on the paper towel. Make sure the pellet of plasmid DNA remains at bottom of the tube.
13. Stand up the tubes with lid open at room temperature or 37° C. for 10-30 min to evaporate residual ethanol and dry out the pellets.
14. Add 50 ul of Dnase free H2O to dissolve the pellets of Plasmid DNA.
15. Measure the concentration of plasmid DNA with Nano-Drop or other UV spectrophotometer at 260/280 nm. 1 OD reading at 260 nm represents DNA concentration at 50 ug/ml.
16. Expecting OD ratio for plasmid DNA: 260/280 nm, 1.8-2.0; 260/230 nm, around 2; 260/270 nm, around 1.2; 260/250 nm, around 1.1; 330 nm, no reading. The OD ratio for plasmid DNA can be varied depended on the source of bacteria.
17. The yield of plasmid DNA is about 5 ug/ml culture, but it varies depended on the type and quality of bacteria.
18. The size of plasmid DNA with or without digestion of restriction enzyme can be verified by agarose gel electrophoresis as shown in FIG. 20.

Example 16

Isolation of Mitochondria DNA and Nucleic DNA from Cells and Tissues

This protocol requests 5×MN (Mitochondria and Nuclei) Isolation Solution as Plug-in module for separation of Mitochondria and Nuclei, and isolation of DNA from Mitochondria and Nuclei in cells and tissues.
Process 1: Isolating Intact Mitochondria and Nuclei from tissue or cell
1. Weigh 20 mg (10-30 mg) tissue and wash it with 1 ml ice-cold PBS if a lot of blood coves the tissue. Mince the tissues to smaller pieces. Scrap attached cell from supporting surface or centrifuge the suspended cell. Transfer minced tissue or cells to container for homogenization.
2. Add 1 ml of 1×MN Isolation Solution and homogenize tissue using Dounce manual tissue homogenizer or electrical tissue disruptor at moderate speed (e.g. speed 4) for 20 sec.
3. Let it stand on ice for 5 sec. If visible tissue piece still exist in tissue lysate, repeat homogenization is necessary, which is depended on tissue type and homogenizer used. Do not over homogenize the tissue.
4. Transfer the homogenate to 1.5 ml micro-centrifuge tube (Eppendorf) and centrifuge the sample at 600 g (2700 RPM in micro-centrifuge) for 10 min at 4° C. Keep the pellet on ice for isolation of nuclei DNA later.
5. Transfer the supernatant into a fresh micro-centrifuge tube (Eppendorf), and centrifuge the supernatant at 12,000 g for 15 min at 4° C. Collect the pellet containing Mitochondria and discard supernatant.
6. Resuspend the Mitochondria pellet in 0.5 ml 1×MN Isolation Buffer and centrifuge at 12,000 g for 15 min at 4° C. Collect the pellet containing Mitochondria and discard supernatant.
Process 2: Isolating DNA from Mitochondria and Nuclei by Allzol Kit: 1. Add 100 ul H20 to Mitochondria pellet in Process 1, Step 6 and Nuclei pellet in Process 1, Step 4, mix thoroughly by vortex.
2. Add 100 ul of 2×PLIS solution, or 200 ul of 1.5×DAP solution to lyse the Mitochondria or Nuclei.
3. Add 90 ul of ethanol to the lysate with 2×PLIS solution or add 130 ul of ethanol to the lysate with 1.5×DAP solution, mix thoroughly by inverting the tube back and forth for 20 times, incubate at room temperature for 2 minutes.
4. Centrifuge the mixture containing Mitochondria DNA or Nuclei DNA at 13000 RPM for 5 min at room temperature to pellet Mitochondria DNA or Nuclei DNA.
5. Pour out and discard supernatant and save pellets of Mitochondria DNA or Nuclei DNA.
6. Wash pellet of Mitochondria DNA or Nuclei DNA by adding 1 ml of 75% ethanol and inverting the tube back and forth for 20 times.

7. Centrifuge the washed pellet of Mitochondria DNA or Nuclei DNA at 13000 RPM (16000 g RCF) for 1 min at room temperature.
8. Pour out and discard supernatant, add 0.5 ml of 75% ethanol and inverting the tube back and forth for 20 times.
9. Centrifuge the washed pellet of Mitochondria DNA or Nuclei DNA at 13000 RPM (16000 g RCF) for 1 min at room temperature.
10. Pour out and discard supernatant, invert tube on paper towel with lid open to drain out last bit of washing solution with slightly knocking the tube on the paper towel.
11. Stand up the tubes with lid open at room temperature or 37° C. for 10-30 min to evaporate residual ethanol and dry out the pellets.
12. Add 30 ul of Dnase free H20 or TE buffer to dissolve the pellets of Mitochondria DNA or Nuclei DNA.
13. Measure the concentration of Mitochondria DNA or Nuclei DNA with NanoDrop or other UV spectrophotometer at 260/280 nm. 1 OD reading at 260 nm represents DNA concentration at 50 ug/ml.
14. Expecting OD ratios for DNA are: 260/280 nm, 1.8-2.0; 260/230 nm, around 2; 260/270 nm, around 1.2; 260/250 nm, around 1.1; 330 nm, no reading. The ratios for Mitochondria DNA and Nuclei DNA can be varied depended on the source of specimens.
15. The yields of Mitochondria DNA and Nucleic DNA are varied depended on the type and quality of specimen, and separation of Mitochondria from Nuclei. Reference yield of Mitochondria DNA is about 0.4 ug/mg tissue and yield of Nuclei DNA is about 0.8 ug/mg tissue. This procedure may be up/down scaled if necessary.
16. The intactness of Mitochondria DNA or Nuclei DNA can be verified by Agarose Gel electrophoresis as shown in FIG. 21. The effective of separation and isolation of Mitochondria DNA and Nuclei DNA can be determined by QPCR with Mitochondria DNA specific primers such as Cyto B gene as shown in FIG. 22.

Example 17

Removal of DNA from Large RNA/mRNA and Small RNA/miRNA

This protocol requests 20×DNA Eliminator as Plug-in module for elimination of DNA contaminated in Large RNA/mRNA and Small RNA/miRNA and isolation of Large RNA/mRNA and Small RNA/miRNA without DNA contamination. 1. Large RNA/mRNA or Small RNA/miRNA specimen should be in H20, TE or appropriate buffer preventing Large RNA/mRNA or Small RNA/miRNA from degradation.
2. Add 20×DNA Eliminator at 1:19 ratio into the Large RNA/mRNA or Small RNA/miRNA samples contaminated with DNA, for example, add 5 ul of 20×DNA Eliminator into 95-100 ul of Large RNA/mRNA or Small RNA/miRNA samples in a centrifuge tube.
3. Incubate at room temperature for 15 minutes.
4. Add 1.5×DAP solution at 2 volume of the Large RNA/mRNA or Small RNA/miRNA samples to the Large RNA/mRNA or Small RNA/miRNA samples after elimination of DNA, and mix thoroughly, for example, add 200 ul of 1.5× DAP solution.
5. Add 100% ethanol at 4.5 volumes of Large RNA/mRNA or Small RNA/miRNA samples to the Large RNA/mRNA or Small RNA/miRNA sample with 1.5×DAP solution, mix thoroughly and leave at room temperature for 2 minute. For example, add 450 ul of ethanol.

6. Centrifuge the micro-centrifuge tube at 13000 RPM for 5 min at room temperature.
7. Pour out and discard supernatant, and wash pellet of Large RNA/mRNA or Small RNA/miRNA by adding 1 ml of 75% ethanol and inverting the tube back and forth for 20 times.
8. Centrifuge the washed pellet of Large RNA/mRNA or Small RNA/miRNA at 13000 RPM (16000 g RCF) for 1 min at room temperature.
9. Pour out and discard supernatant, add 0.5 ml of 75% ethanol and inverting the tube back and forth for 20 times.
10. Centrifuge the washed pellet of Large RNA/mRNA or Small RNA/miRNA at 13000 RPM (16000 g RCF) for 1 min at room temperature.
11. Pour out and discard supernatant, invert tube on paper towel with lid open to drain out last bit of washing solution with slightly knocking the tube on the paper towel. Make sure the Large RNA/mRNA or Small RNA/miRNA pellet stay at bottom of the tube.
12. Stand up the tubes with lid open at room temperature or 37° C. for 10-30 min to evaporate residue ethanol and dry out the pellets.
13. Add 30 ul of Dnase and Rnase free H2O to dissolve the pellets of Large RNA/mRNA or Small RNA/miRNA.
14. Measure the concentration of Large RNA/mRNA or Small RNA/miRNA with NanoDrop or other UV spectrophotometer at 260/280 nm. 1 OD reading at 260 nm represents RNA concentration at 40 ug/ml.
Expecting OD ratio for Large RNA/mRNA or Small RNA/miRNA is varied depending on amount and types of Large RNA/mRNA or Small RNA/miRNA samples, ideally should be 260/280 nm, 1.8-2.0; 260/230 nm, around 2; 260/270 nm, around 1.2; 260/250 nm, around 1.1; 330 nm, no reading.
15. Effectiveness of DNA removal is verified either by Agarose gel electrophoresis as shown in FIG. 23 or in QPCR and QRT-PCR as shown in FIG. 24.

Example 18

DNA Fragmentation

This protocol requests 1000×DNA Mincer and 20× Mincer Buffer as Plug-in modules for DNA fragmentation and purification of fragmented DNA.
Process 1: Titration of DNA Mincer for DNA Samples: 1. Dilution of 1000×DNA Mincer: Add 1 ul of 1000×DNA Mincer into 25, 50 and 100 ul of 20× Mincer Buffer respectively to make 20× Mincer Solution with three different concentrations of Mincer.
2. Prepare 3 tubes containing 19 ul DNA samples at the same concentration between 20-200 ng/ul. DNA specimen should be in H20, TE or appropriate buffer preventing DNA from degradation.
3. Add 1 ul 20× Mincer solution of three concentrations to each DNA sample respectively.
4. Mix thoroughly and incubate at room temperature for 15 min.
5. Run 3% agarose gel to determine appropriate titer for DNA Mincer.
Process 2: Fragmentation of DNA by DNA Mincer: 1. DNA specimen should be in H20, TE or appropriate buffer preventing DNA from degradation. Bring concentration of DNA to the same concentration as tested in Titration test above. (20-200 ng/ul).
2. Add validated 20× Mincer solution at 1:19 ratio into the DNA samples, for example, add 2 ul of 20× Mincer Solution into 38 ul of DNA samples.

3. Mix thoroughly and incubate at room temperature for 15 minutes.
4. Add 1.5×DAP solution at 2 volume of the DNA samples with Mincer Solution to the DNA samples after mincing of DNA, and mix thoroughly, for example, add 80 ul of 1.5× DAP solution.
5. Add 100% ethanol at 4.5 volume of DNA samples with Mincer Solution to the DNA sample with 1.5×DAP solution, mix thoroughly and leave at room temperature for 2 minute. For example, add 180 ul of ethanol.
6. Centrifuge the micro-centrifuge tube at 13000 RPM for 5 min at room temperature.
7. Pour out and discard supernatant, and wash pellet of DNA by adding 1 ml of 75% ethanol and inverting the tube back and forth for 20 times.
8. Centrifuge the washed pellet of DNA at 13000 RPM (16000 g RCF) for 1 min at room temperature.
9. Pour out and discard supernatant, add 0.5 ml of 75% ethanol and inverting the tube back and forth for 20 times.
10. Centrifuge the washed pellet of DNA at 13000 RPM (16000 g RCF) for 1 min at room temperature.
11. Pour out and discard supernatant, invert tube on paper towel with lid open to drain out last bit of washing solution with slightly knocking the tube on the paper towel. Make sure the DNA pellet stay at bottom of the tube.
12. Stand up the tubes with lid open at room temperature or 37° C. for 10-30 min to evaporate residue ethanol and dry out the pellets.
13. Add 30 ul of Dnase and Rnase free H2O to dissolve the pellets of DNA.
14. Measure the concentration of DNA with NanoDrop or other UV spectrophotometer at 260/280 nm. 1 OD reading at 260 nm represents DNA concentration at 50 ug/ml.
Expecting OD ratio for DNA is varied depending on amount and types of DNA samples, ideally should be 260/280 nm, 1.8-2.0; 260/230 nm, around 2; 260/270 nm, around 1.2; 260/250 nm, around 1.1; 330 nm, no reading.
15. Effectiveness of DNA fragmentation is verified by Agarose gel electrophoresis as shown in FIG. 25.

Example 19

DNA Methylation Analysis

This protocol requests conversion reagents and Enhancer as Plug-in modules for DNA conversion and purification of converted DNA, which is essential step in DNA methylation analysis.
Process 1: Conversion of DNA: 1. Preparation of Conversion reagent: weight out 0.4 g conversion reagent powder, add 725 ul of Enhancer and 55 ul of 1.5×DAP solution. Mix the reagent thoroughly; it may take up to 20 min to dissolve the reagent. Use 100-200 ul of dissolved reagent for each preparation of converted DNA
2. Prepare 60% Ethanol, 600-1200 ul for each preparation of converted DNA.
3. Prepare 75% Ethanol, 3 ml for each preparation of converted DNA.
4. Prepare diluted Enhancer Solution: add 13 ul of enhancer to 99 ul of H2O in micro-centrifuge tube and mix thoroughly. 100 ul for each preparation of converted DNA.
5. Add 90 ul of conversion reagent into a PCR tube and add DNA samples 100-400 ng at 10-30 ul, mix thoroughly by inverting tube for 20 times. DNA sample should be in H20 or TE. DNA samples also can be plasma, serum or lysate of FFPE tissue section.
6. Heat PCR tube in PCR instrument at 98° C. for 10 min, then heat at 65° C. for 2.5 hours to convert DNA.
7. Transfer the converted DNA into micro-centrifuge tube after completion of conversion of DNA.
8. Add 60% ethanol at 6 volume of converted DNA, for examples, 600 ul of 60% ethanol to 100 ul of DNA in conversion reagent, or 1200 ul of 60% ethanol to 200 ul of conversion reagent containing DNA. Mix thoroughly by inverting the tube back and forth for 20 times, and incubate at room temperature for 2 minutes.
Process 2: Isolation of converted DNA: 1. Centrifuge the micro-centrifuge tube containing converted DNA in Step 8, Process 1 at 13000 RPM for 5 min at room temperature, discard supernatant and save DNA pellet.
2. Add 1 ml of 75% ethanol the DNA pellet, wash the DNA pellet by invert tube back and forth for 20 times, incubate at room temperature for 2 minutes.
3. Centrifuge the micro-centrifuge tube containing DNA pellet at 13000 RPM for 1 min at room temperature, discard supernatant and save DNA pellet.
4. Add 100 ul of diluted Enhancer solution to dissolve DNA pellet, incubate at room temperature for 20 minutes.
5. Add 200 ul of 1.5×DAP solution into dissolved DNA.
6. Add 600 ul (450 ul) of ethanol into dissolved DNA, mix thoroughly by inverting tube back and forth for 20 times, and leave at room temperature for 2 minutes.
7. Centrifuge the micro-centrifuge tube containing dissolved DNA at 13000 RPM for 5 min at room temperature, discard supernatant and save DNA pellet.
8. Add 1 ml of 75% ethanol the DNA pellet, wash the DNA pellet by invert tube back and forth for 20 times, incubate at room temperature for 1 minutes.
9. Centrifuge the micro-centrifuge tube containing DNA at 13000 RPM for 1 min at room temperature, discard supernatant and save DNA pellet.
10. Add 1 ml of 75% ethanol the DNA pellet, wash the DNA pellet by invert tube back and forth for 20 times, incubate at room temperature for 1 minutes.
11. Centrifuge the micro-centrifuge tube containing DNA at 13000 RPM for 1 min at room temperature, discard supernatant and save DNA pellet.
12. Invert tube on paper towel with lid open to drain out last bit of washing solution with slightly knocking the tube on the paper towel. Make sure keep the DNA pellet at bottom of tube.
13. Stand up the tubes with lid open at room temperature or 37° C. for 10-30 min to evaporate residual ethanol and dry out the DNA pellets.
14. Add 30 ul of Dnase and Rnase free H2O to dissolve the pellets of converted DNA.
15. Measure the concentration of converted DNA with NanoDrop or other UV spectrophotometer at 260/280 nm. 1 OD reading at 260 nm represents DNA concentration at 50 ug/ml.
16. Expecting OD ratio for converted DNA: 260/280 nm, 1.8-2.0; 260/230 nm, around 2; 260/270 nm, around 1.2; 260/250 nm, around 1.1; 330 nm, no reading. The OD ratio for converted DNA can be varied depended on the source of specimens.
17. The yields of converted DNA is about 50-90% of input DNA for conversion depended on the source of input DNA.
18. The yield of converted DNA can also be checked in 3% agarose gel.
19. Efficiency and effective of DNA conversion and DNA methylation can be verified and analyzed by Quantitative PCR or QPCR with primers for converted DNA and unconverted DNA as shown in FIGS. 26 and 27.

Example 20

DNA Labeling

This protocol requests 20×DNA labeling Mix as Plug-in module for labeling DNA
1. DNA sample should be in H20, TE or appropriate buffer preventing DNA from degradation.
2. Add 20×DNA Labeling Mix at 1:19 ratio into the DNA samples, for example, add 2 ul of 20×DNA labeling into 38 ul of DNA samples.
3. Incubate at 25° C. or room temperature for 15 minutes.
4. Add 1.5×DAP solution at 2 volume of the DNA samples to the DNA samples, and mix thoroughly, for example, add 80 ul of 1.5×DAP solution.
5. Add 100% ethanol at 4.5 volume of DNA samples to DNA sample with 1.5×DAP solution, mix thoroughly and leave at room temperature for 2 minute. For example, add 180 ul of ethanol.
6. Centrifuge the micro-centrifuge tube at 13000 RPM for 5 min at room temperature.
7. Pour out and discard supernatant, and wash pellet of DNA by adding 1 ml of 75% ethanol and inverting the tube back and forth for 20 times.
8. Centrifuge the washed pellet of DNA at 13000 RPM (16000 g RCF) for 1 min at room temperature.
9. Pour out and discard supernatant, add 0.5 ml of 75% ethanol and inverting the tube back and forth for 20 times.
10. Centrifuge the washed pellet of DNA at 13000 RPM (16000 g RCF) for 1 min at room temperature.
11. Pour out and discard supernatant, invert tube on paper towel with lid open to drain out last bit of washing solution with slightly knocking the tube on the paper towel. Make sure the DNA pellet stay at bottom of the tube.
12. Stand up the tubes with lid open at room temperature or 37° C. for 10-30 min to evaporate residue ethanol and dry out the pellets.
13. Add 30 ul of Dnase and Rnase free H2O to dissolve the pellets of DNA.
14. Measure the concentration of DNA with NanoDrop or other UV spectrophotometer at 260/280 nm. 1 OD reading at 260 nm represents DNA concentration at 50 ug/ml.
Expecting OD ratio for DNA is varied depending on amount and types of DNA samples, ideally should be 260/280 nm, 1.8-2.0; 260/230 nm, around 2; 260/270 nm, around 1.2; 260/250 nm, around 1.1; 330 nm, no reading.

Example 21

RNA Labeling

This protocol requests 20×RNA labeling Mix as Plug-in module for labeling RNA
1. RNA sample should be in H20, TE or appropriate buffer preventing RNA from degradation.
2. Add 20×RNA Labeling Mix at 1:19 ratio into the RNA samples, for example, add 2 ul of 20×RNA labeling into 38 ul of RNA samples.
3. Incubate at 40° C. for 60 minutes.
4. Add 1.5×DAP solution at 2 volume of the RNA samples to the RNA samples, and mix thoroughly, for example, add 80 ul of 1.5×DAP solution.
5. Add 100% ethanol at 4.5 volume of RNA samples to RNA sample with 1.5×DAP solution, mix thoroughly and leave at room temperature for 2 minute. For example, add 180 ul of ethanol.
6. Centrifuge the micro-centrifuge tube at 13000 RPM for 5 min at room temperature.
7. Pour out and discard supernatant, and wash pellet of RNA by adding 1 ml of 75% ethanol and inverting the tube back and forth for 20 times.
8. Centrifuge the washed pellet of RNA at 13000 RPM (16000 g RCF) for 1 min at room temperature.
9. Pour out and discard supernatant, add 0.5 ml of 75% ethanol and inverting the tube back and forth for 20 times.
10. Centrifuge the washed pellet of RNA at 13000 RPM (16000 g RCF) for 1 min at room temperature.
11. Pour out and discard supernatant, invert tube on paper towel with lid open to drain out last bit of washing solution with slightly knocking the tube on the paper towel. Make sure the RNA pellet stay at bottom of the tube.
12. Stand up the tubes with lid open at room temperature or 37° C. for 10-30 min to evaporate residue ethanol and dry out the pellets.
13. Add 30 ul of Dnase and Rnase free H2O to dissolve the pellets of RNA.
14. Measure the concentration of RNA with NanoDrop or other UV spectrophotometer at 260/280 nm. 1 OD reading at 260 nm represents RNA concentration at 40 ug/ml.
Expecting OD ratio for RNA is varied depending on amount and types of RNA samples, ideally should be 260/280 nm, 1.8-2.0; 260/230 nm, around 2; 260/270 nm, around 1.2; 260/250 nm, around 1.1; 330 nm, no reading.

Example 22

Quality Comparison with Market Leaders

Quality of the biomolecules isolated by this invention and by other two market leaders is compared. Method of market leader I is based on phenol and chloroform extraction and precipitation, which served as control for the method in core module with differential precipitation method (Allzol Kit) in this invention herein. Method of market leader Q is based on affinity column, which served as control for the method by differential solid phase binding method (Alliso Kit) with affinity column as Plug-in module in this invention herein. As shown in FIG. 28, Panel A, the yield of DNA isolated by this invention from liver tissue is higher than the yield of DNA isolated by market leaders Q and I. The quality of RNA isolated by this invention from liver tissue is better than the RNA isolated by market leaders Q and I as shown in Panel B.

The stability of RNA isolated from liver tissue by this invention is better than the RNA isolated from liver tissue by market leaders Q and I. As shown in FIG. 29, Panel B, the RNA isolated by this invention can be electrophoresed in 1% agarose gel for DNA without degradation but the RNA isolated by market leaders were degraded during electrophoresis in 1% agarose gel for DNA due to less purity of RNA isolated by market leaders I and Q as show in Panel A. The Allzol Kit and Alliso Kit can inhibit Rnase and decontaminate Rnase during RNA isolation. Therefore, the purity of RNA isolated by Allzol Kit and Alliso Kit is higher and Rnase free. The RNA isolated by Allzol Kit and Alliso Kits can keep intact during DNA gel electrophoresis without degradation. All RNA isolated by market leaders' products and isolated by this invention is not degraded when electrophoresed in 1% agarose gel for RNA since the gel contains formaldehyde to inhibit the Rnase activity. The RNA isolated by market leaders contains leftover endogenous Rnase in trace amount, while RNA isolated by Allzol Kit and Allizo Kit is Rnase free with higher purity.

The invention has been described using exemplary preferred embodiments. However, for those skilled in this field, the preferred embodiments can be easily adapted and modified to suit additional applications without departing from the spirit and scope of this invention. Thus, it is to be understood that the scope of the invention is not limited to the disclosed embodiments. On the contrary, it is intended to cover various modifications and similar arrangements based upon the same operating principle. The scope of the claims, therefore, should be accorded the broadest interpretations so as to encompass all such modifications and similar arrangements.

What is claimed is:

1. A kit, comprising: a core module consisting of a decontamination solution and a lysis solution selected from lysis solution 1, lysis solution 2, lysis solution 3 and lysis solution 4; wherein the decontamination solution consists of sodium iodide, ammonium acetate, sodium acetate, sodium citrate, sodium chloride, ethylenediaminetetraacetic acid disodium salt dehydrate (EDTA) and tris(2-carboxyethyl)phosphine hydrochloride (TCEP); wherein the lysis solution inhibits endogenous degrading enzymes and extracts a component of a biological sample without phenol/chloroform; wherein the component of the biological sample is a DNA/ccfDNA, Large RNA/mRNA/ccfRNA, Small RNA/miRNA/ccfmiRNA, protein, lipid, carbohydrate, and metabolite.

2. The kit of claim 1, wherein the biological sample is a solid specimen, liquid specimen, clinical specimen, chemical or enzymatic specimen or a gel slice specimen containing biomolecules.

3. The kit of claim 1, further comprising;
a plug-in module, wherein the plug-in module is a solid phase binding material for binding and purification of nucleic acids or carbohydrate.

4. The kit of claim 1, further comprising;
one or more plug-in modules for extracting or isolating a component from the biological sample without using toxic phenol/chloroform, wherein the one or more plug-in modules is selected from the group consisting of an affinity column, magnetic beads and Concanavalin A column.

5. The kit of claim 3, wherein the plug-in module is an affinity column or magnetic beads for nucleic acid binding and purification or a Concanavalin A (Con-A) column for binding carbohydrate.

6. The kit of claim 1, further comprising a trimethylene bromochloride solution for lipid extraction.

7. A kit for extracting a component from a biological sample, comprising:
a core module having an Alliso configuration, a solid phase affinity column for binding nucleic acid or a carbohydrate, and a decontamination solution; wherein the Alliso configuration consists of a lysis solution selected from lysis solution 1, lysis solution 2, lysis solution 3 or lysis solution 4, wherein the decontamination solution consists of sodium iodide, ammonium acetate, sodium acetate, sodium citrate, sodium chloride, ethylenediaminetetraacetic acid disodium salt dehydrate (EDTA) and tris(2-carboxyethyl)phosphine hydrochloride (TCEP).

8. The kit of claim 7, wherein the extracted component of the biological sample is a DNA/ccfDNA, Large RNA/mRNA/ccfRNA, Small RNA/miRNA/ccfmiRNA, protein, lipid, carbohydrate or metabolite.

9. The kit of claim 7, wherein the solid phase affinity column is an affinity column or magnetic beads for nucleic acid binding and purification, or a Con-A column for binding of a carbohydrate.

10. The kit of claim 7, further comprising:
an additional core module, the core module having an Allzol configuration; wherein the Allzol configuration consists of a lysis solution selected from lysis solution 1, lysis solution 2, lysis solution 3 or lysis solution 4 and a decontamination solution consisting of sodium iodide, ammonium acetate, sodium acetate, sodium citrate, sodium chloride, ethylenediaminetetraacetic acid disodium salt dehydrate (EDTA) and tris(2-carboxyethyl) phosphine hydrochloride (TCEP).

11. A kit, comprising:
a lysis solution selected from lysis solution 1, lysis solution 2, lysis solution 3 or lysis solution 4 and a decontamination solution consisting of sodium iodide, ammonium acetate, sodium acetate, sodium citrate, sodium chloride, ethylenediaminetetraacetic acid disodium salt dehydrate (EDTA) and tris(2-carboxyethyl)phosphine hydrochloride (TCEP) and a plug-in module;
wherein the lysis solution and decontamination solution degrades/inhibits endogenous enzymes.

12. The kit of claim 11, wherein the plug-in module is a solid phase binding material for nucleic acid binding and purification.

13. The kit of claim 11, further comprising a trimethylene bromochloride solution for extracting a lipid.

14. The kit of claim 11, further comprising one or more plug-in modules, wherein the one or more plug-in modules are selected from a tissue homogenizer, liquid handler, magnetic separator, vacuum, incubator, centrifuge, chromatographic instrument, electrophoresis apparatus, fraction collectors, dryer or a combination thereof.

15. The kit of claim 11, further comprising a plug-in module, wherein the plug-in module extracts and removes polysaccharide and polyphenol of a biological sample, wherein the biological sample is a plant tissue that is rich in polysaccharide and polyphenol.

* * * * *